US012599728B2

(12) United States Patent (10) Patent No.: US 12,599,728 B2

Von Schuckmann (45) Date of Patent: Apr. 14, 2026

(54) DEVICE FOR INHALING POWDER-TYPE SUBSTANCES, SUBSTANCE CONTAINER FOR A DEVICE OF THIS TYPE AND METHOD FOR FILLING A DEVICE OF THIS TYPE

(71) Applicant: Alfred Von Schuckmann, Kevelaer (DE)

(72) Inventor: Alfred Von Schuckmann, Kevelaer (DE)

( * ) Notice: Subject to any disclaimer, the term of this patent is extended or adjusted under 35 U.S.C. 154(b) by 1310 days.

(21) Appl. No.: 17/422,514

(22) PCT Filed: Jan. 14, 2020

(86) PCT No.: PCT/EP2020/050808

§ 371 (c)(1),
(2) Date: Jul. 13, 2021

(87) PCT Pub. No.: WO2020/148276

PCT Pub. Date: Jul. 23, 2020

(65) Prior Publication Data

US 2022/0126035 A1 Apr. 28, 2022

(30) Foreign Application Priority Data

Jan. 14, 2019 (DE) ..................... 10 2019 100 832.8
Jan. 13, 2020 (DE) ..................... 10 2020 100 550.4

(51) Int. Cl.
*A61M 15/00* (2006.01)

(52) U.S. Cl.
CPC .... *A61M 15/0028* (2013.01); *A61M 15/0025* (2014.02); *A61M 15/0035* (2014.02);
(Continued)

(58) Field of Classification Search
CPC .............. A61M 15/00; A61M 15/0001; A61M 15/0003; A61M 15/0028; A61M 15/003;
(Continued)

(56) References Cited

U.S. PATENT DOCUMENTS 3,558,003 A * 1/1971 Jones ................. B65D 83/0409
221/279
4,206,758 A * 6/1980 Hallworth ......... A61M 15/0028
128/203.23
(Continued)

FOREIGN PATENT DOCUMENTS

EP 0 211 595 A2 2/1987
EP 1 992 376 A1 11/2008
(Continued)

OTHER PUBLICATIONS

International Search Report of PCT/EP2020/050814, mailed Apr. 21, 2020.
(Continued)

*Primary Examiner* — Colin W Stuart
(74) *Attorney, Agent, or Firm* — Collard & Roe, P.C.

(57) ABSTRACT

A device for inhaling powder-type substances includes a plurality of substance containers that can be moved successively into an emptying position, wherein the substance containers—which are not connected to one another—are accommodated in direct contact with one another in a guide unit attached to the device and can be moved by contact pressure propagating among the substance containers. The guide unit has a drive wheel with accommodating forms separated by drive teeth. The substance container in the emptying position is located in an accommodating form of the drive wheel. A substance container for a device for inhaling powder-type substances has two sub-regions, each separately having an amount of the substance, and both sub-regions have an openable, pierceable cover. A method
(Continued)

for filling a device for inhaling powder-type substances uses a plurality of substance containers that can be moved successively into an emptying position.

14 Claims, 39 Drawing Sheets

(52) U.S. Cl.
CPC .... *A61M 15/0041* (2014.02); *A61M 15/0075* (2014.02); *A61M 2202/064* (2013.01); *A61M 2206/16* (2013.01)

(58) Field of Classification Search
CPC .......... A61M 15/0031; A61M 15/0043; A61M 15/0041; A61M 15/0045; A61M 15/0046; A61M 15/0061; A61M 15/0063; A61M 15/0025; A61M 15/0026; A61M 15/0075; A61M 2202/064
See application file for complete search history.

(56) References Cited

U.S. PATENT DOCUMENTS

| | | | |
|---|---|---|---|
| 5,048,514 A * | 9/1991 | Ramella ............ | A61M 15/0033 128/203.15 |
| 7,571,724 B2 | 8/2009 | Braithwaite | |
| 8,511,304 B2 | 8/2013 | Anderson et al. | |
| 2002/0092520 A1 * | 7/2002 | Casper .............. | A61M 15/0081 128/200.22 |
| 2003/0163099 A1 * | 8/2003 | Wermeling ......... | A61M 15/008 604/258 |
| 2007/0131225 A1 | 6/2007 | Rand | |
| 2007/0215149 A1 * | 9/2007 | King ................... | A61M 15/001 128/200.24 |
| 2009/0194105 A1 * | 8/2009 | Besseler ........... | A61M 15/0028 128/203.15 |
| 2010/0078021 A1 | 4/2010 | Thoe et al. | |
| 2010/0294278 A1 | 11/2010 | Mosier et al. | |
| 2012/0037718 A1 * | 2/2012 | Dunne ................. | A61M 11/001 239/1 |
| 2012/0145150 A1 * | 6/2012 | Donovan ........... | A61M 15/001 128/203.15 |
| 2016/0121057 A1 * | 5/2016 | Dyche ................ | B05B 11/1001 128/200.23 |
| 2018/0214645 A1 | 8/2018 | Reevell | |
| 2018/0344951 A1 * | 12/2018 | Shahaf ............. | A61M 15/0065 |

FOREIGN PATENT DOCUMENTS

| | | |
|---|---|---|
| EP | 3 111 978 A1 | 1/2017 |
| WO | 02/053216 A1 | 7/2002 |
| WO | 2003/061743 A1 | 7/2003 |
| WO | 2004/045688 A1 | 6/2004 |
| WO | 2005/049121 A1 | 6/2005 |
| WO | 2018/195086 A1 | 10/2018 |

OTHER PUBLICATIONS

International Search Report of PCT/EP2020/050808, mailed Apr. 20, 2020.

* cited by examiner

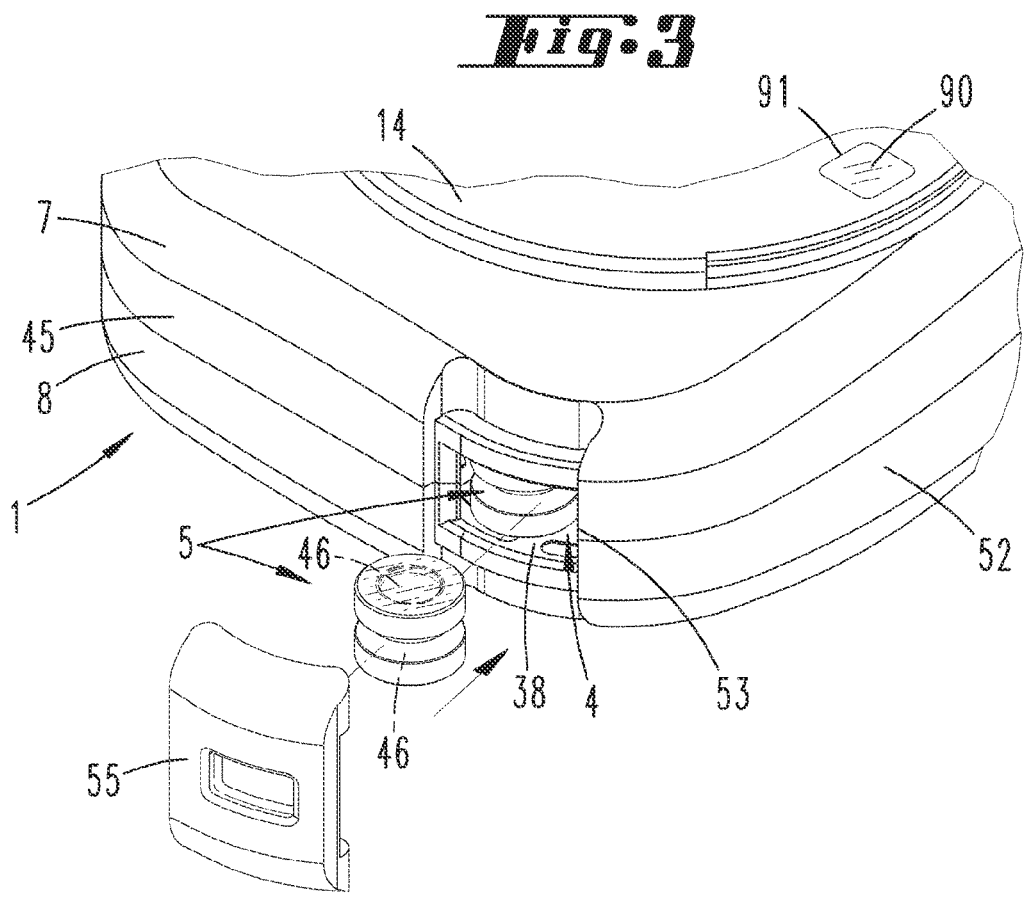
*Fig. 3*
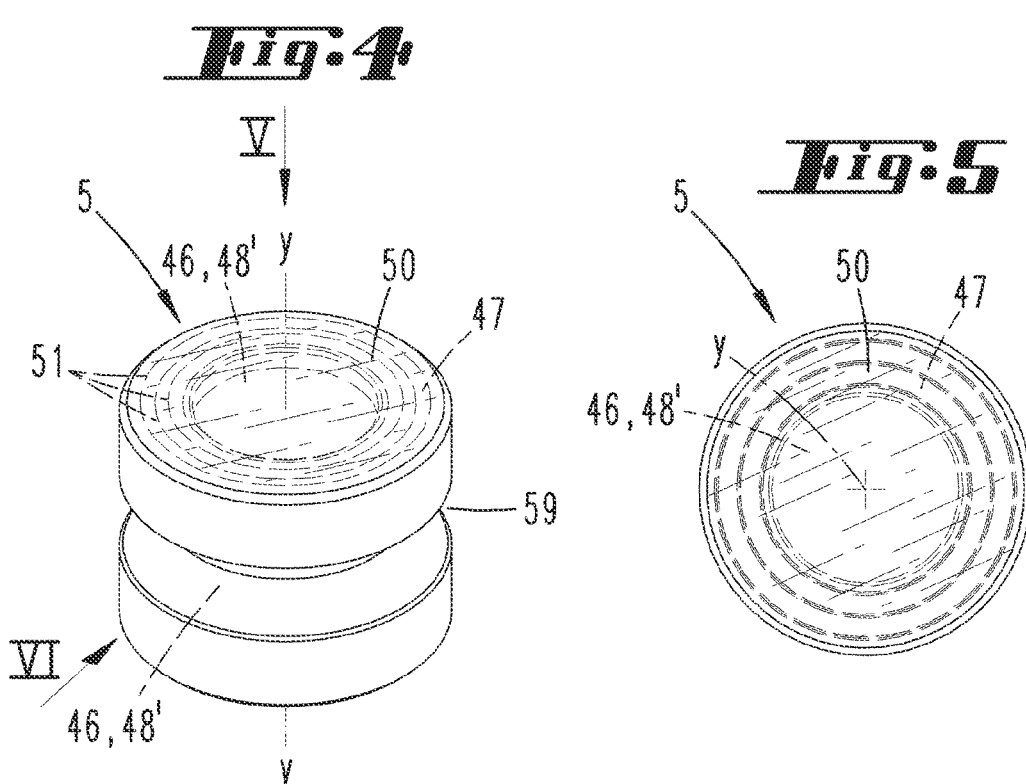
*Fig. 4*
*Fig. 5*

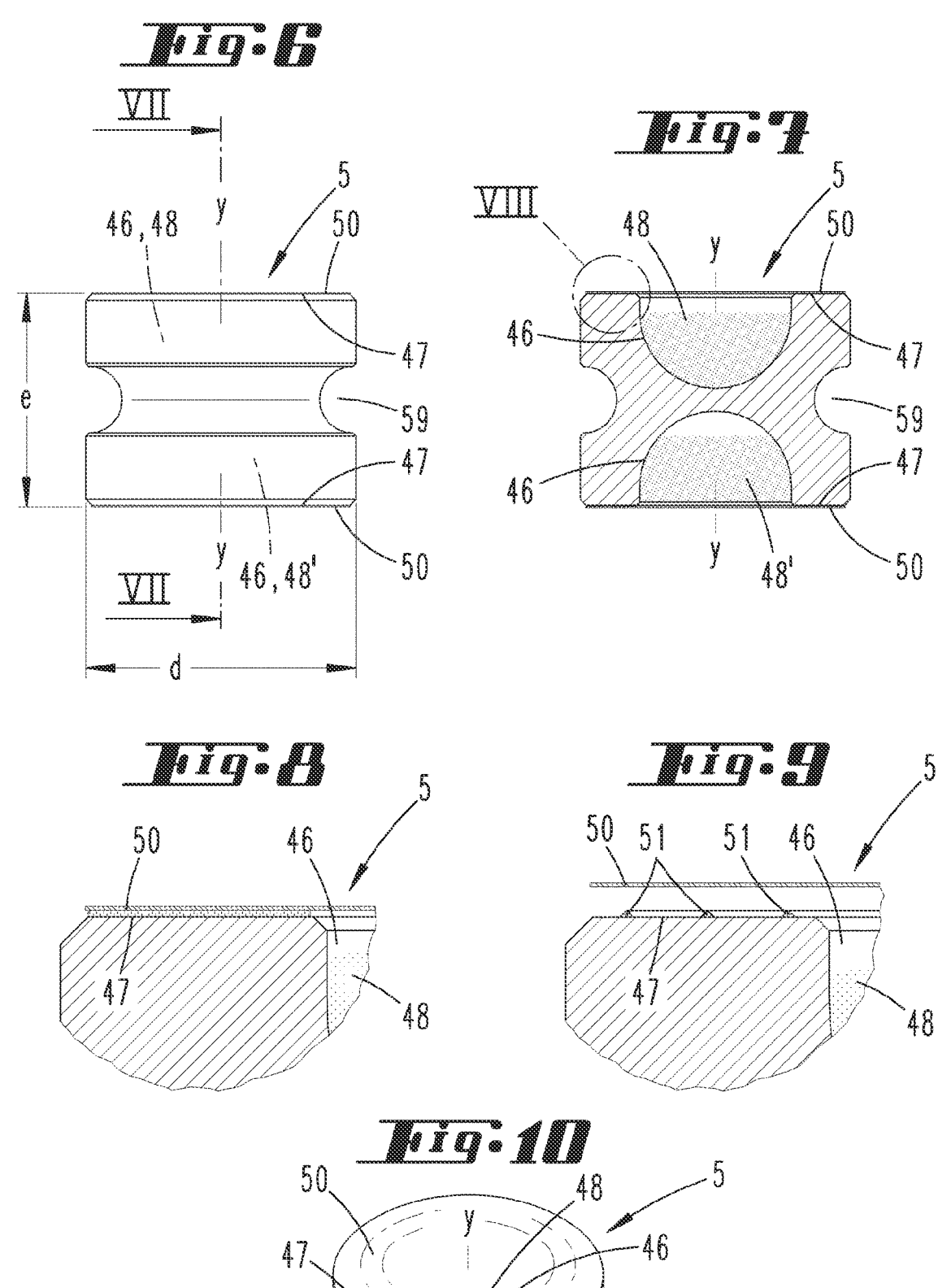

*Fig·13*

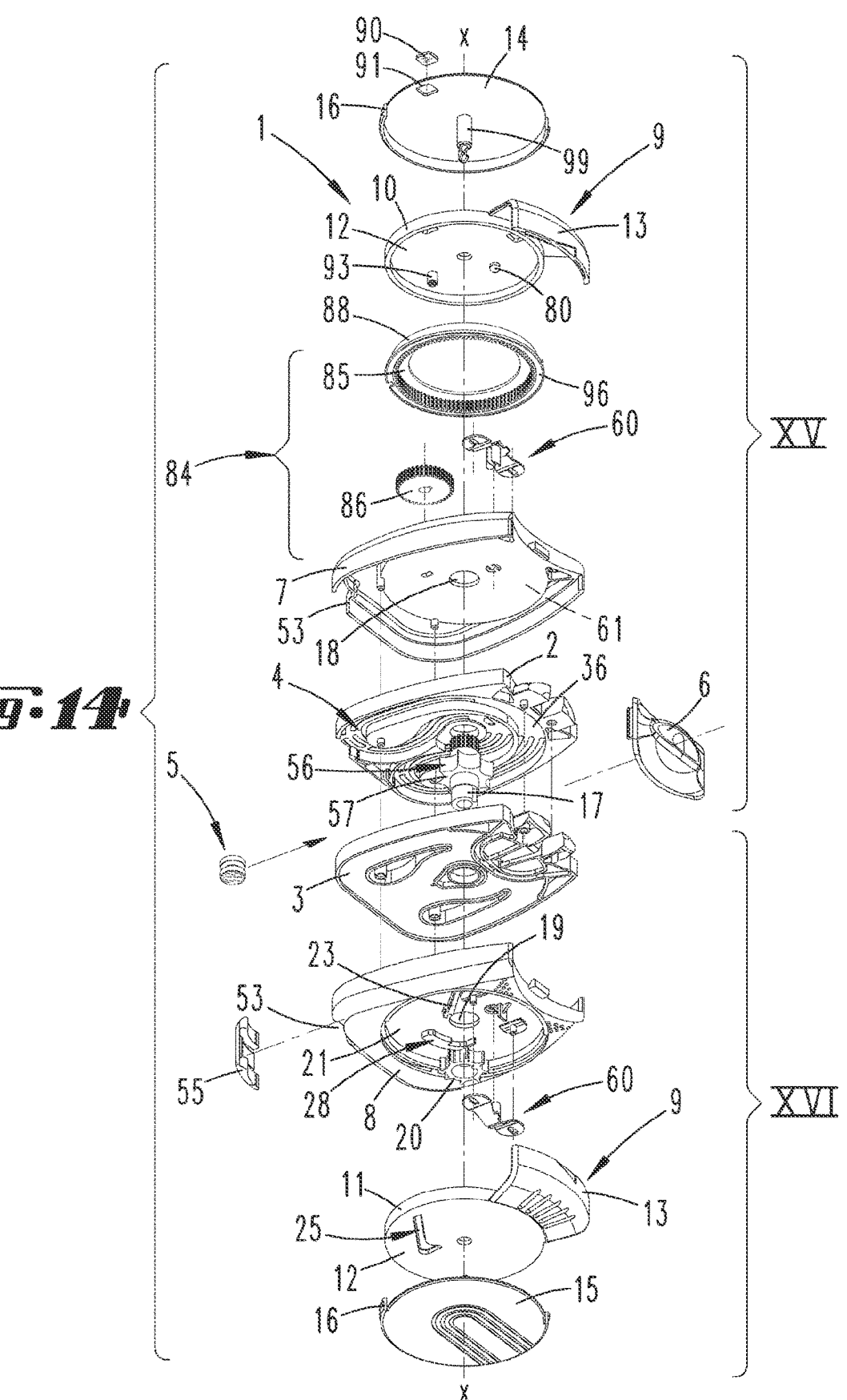
_Fig. 14_

*Fig:17*
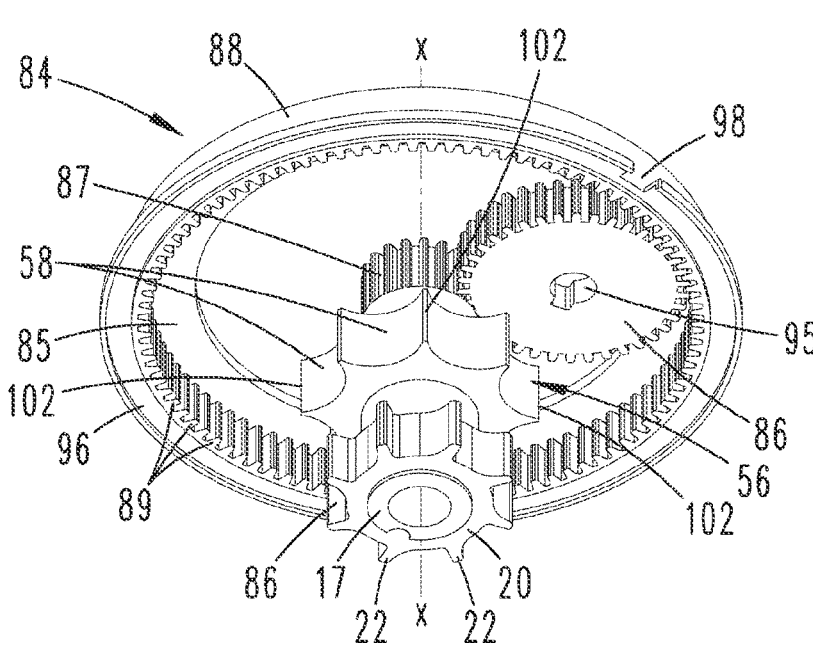
*Fig:18*
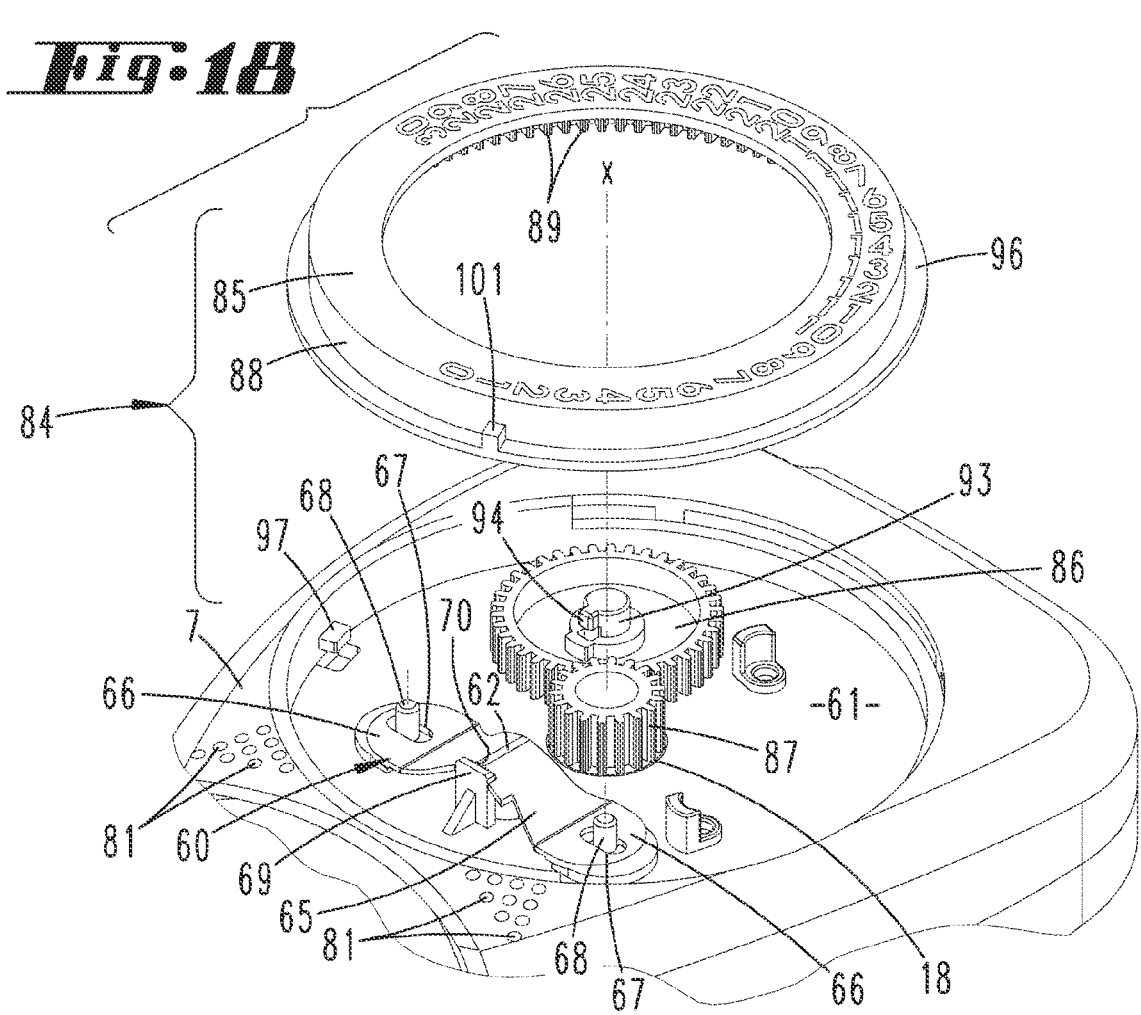

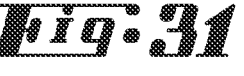
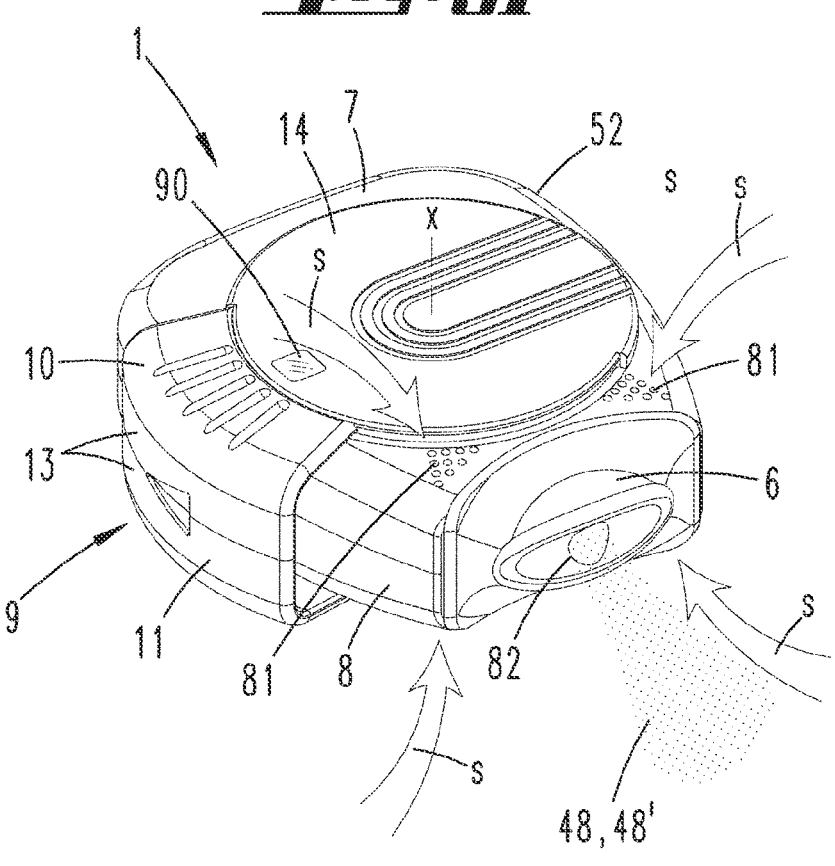
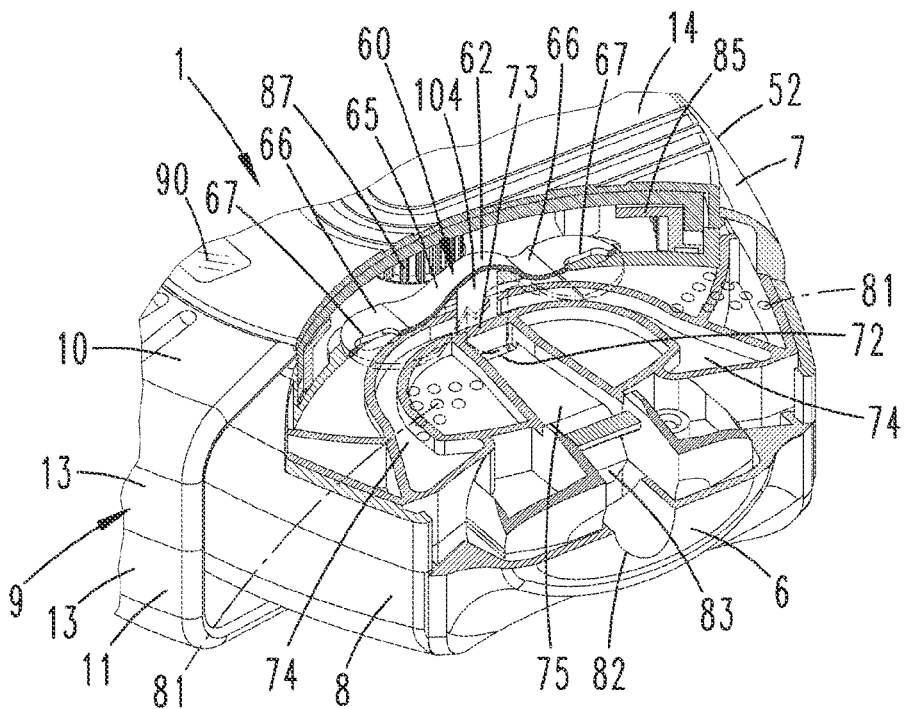

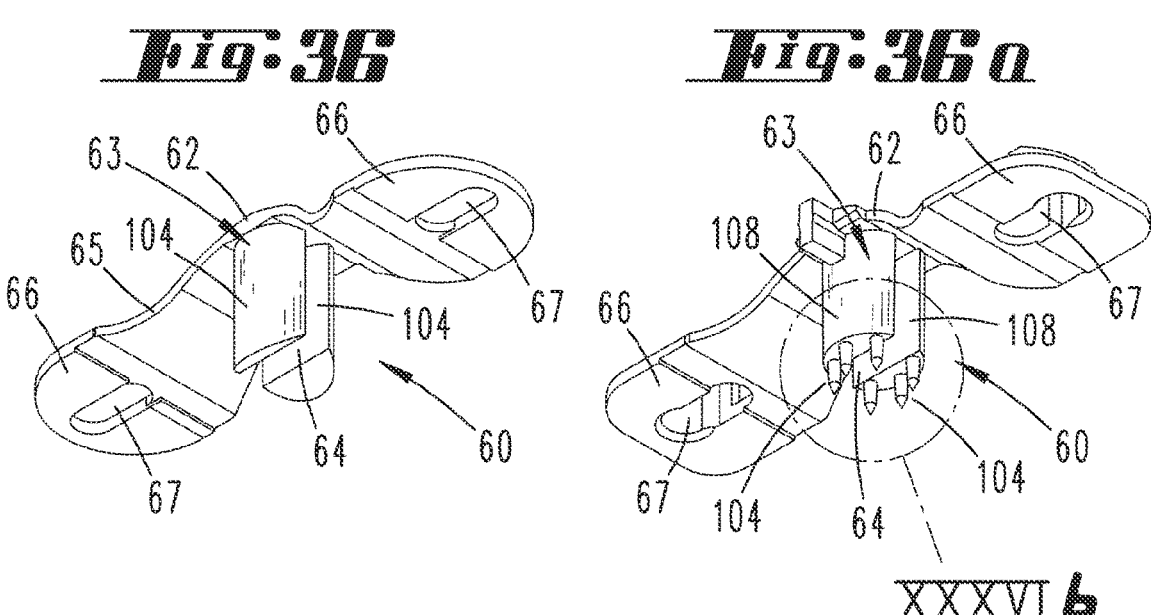
Fig. 36
Fig. 36a
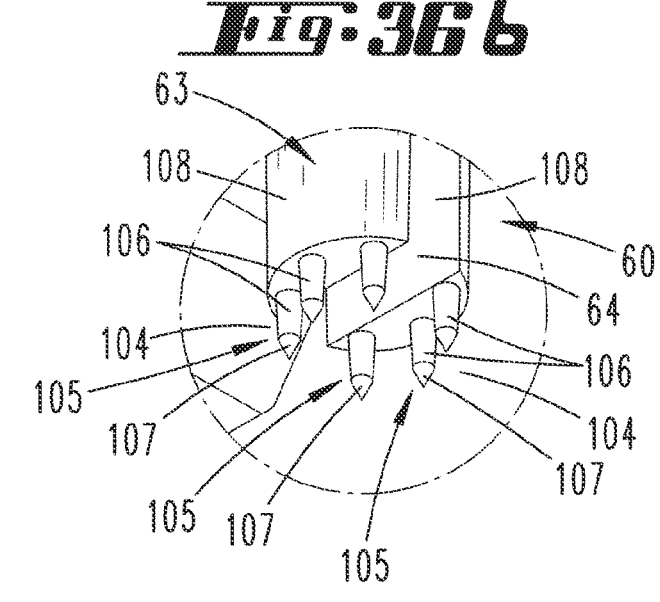
Fig. 36b
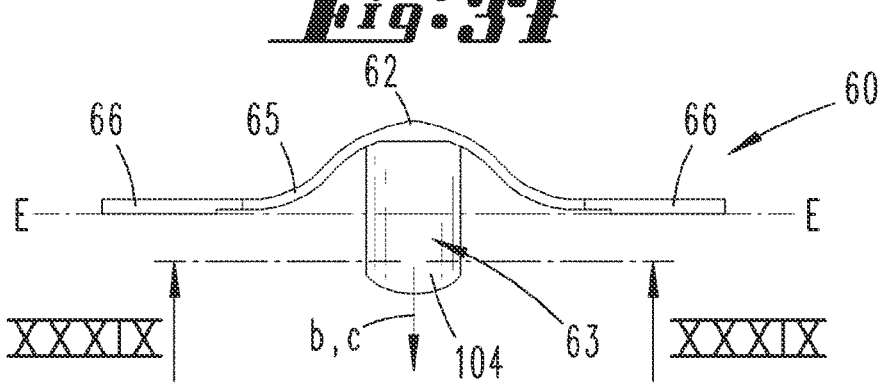
Fig. 37

DEVICE FOR INHALING POWDER-TYPE SUBSTANCES, SUBSTANCE CONTAINER FOR A DEVICE OF THIS TYPE AND METHOD FOR FILLING A DEVICE OF THIS TYPE

CROSS REFERENCE TO RELATED APPLICATIONS

This application is the National Stage of PCT/EP2020/050808 filed on Jan. 14, 2020, which claims priority under 35 U.S.C. § 119 of German Application No. 10 2019 100 832.8 filed on Jan. 14, 2019 and German Application No. 10 2020 100 550.4 filed on Jan. 13, 2020, the disclosures of which are incorporated by reference. The international application under PCT article 21(2) was not published in English.

FIELD OF TECHNOLOGY

The invention initially relates to a device for inhaling powder-type substances, comprising a plurality of substance containers that can be moved successively into an emptying position, wherein the substance containers, which are not connected to one another, are accommodated for direct contact with one another in a guide mechanism attached to the device, and can be moved by contact pressure propagating among the substance containers, wherein the guide mechanism further has a drive wheel comprising accommodating moldings separated by drive teeth.

The invention further relates to a substance container for a device for inhaling powder-type substances.

In addition, the invention relates to a method for filling a device for inhaling powder-type substances with a plurality of substance containers that can be moved successively into an emptying position.

PRIOR ART

Devices of the discussed type serve for the inhalation, in particular for the inhalation of powder-type substances. The substance to be inhaled is provided in substance containers in portions, for dispensing via an air flow, which is built up in the course of an inhalation by the user. The substance container, which is moved into a dispensing-ready position for this purpose, is preferably opened prior to the build-up of the air flow by means of an insertion mechanism. The substance stored in the container in portions is dispelled via the opening resulting thereby and is transported to the mouthpiece via the discharge channel.

Devices are further known, in the case of which a plurality of substance containers are provided in the device arranged one behind the other in a displacement direction of the substance containers. The substance containers can be connected to one another thereby, for example as a result of the design of the substance containers in the manner of a blister pack or of a blister strip.

The substance containers are displaced successively into the emptying position with each actuation of the device.

A device of the discussed type is further known, for example from WO 2005/049 121 A1 (US 2007/0 131 225 A1), in which a plurality of substance containers are accommodated that are moved successively into an emptying position for emptying purposes.

WO 2003/061 743 A1 (U.S. Pat. No. 8,511,304 B2) discloses a device, in which the substance containers are provided in the device so as to be connected to one another in a chain-like manner in the manner of a strip blister, wherein the substance containers are formed in such a way that they store two optionally, and preferably, different substances in specified dosages. These two substances of a substance container are accommodated in sub-regions of the substance container, which are separated from one another until being emptied.

A device for inhaling powder-type substances is known from US 2007/131225 A1, in the case of which the substance containers are moved in a continuous line by means of drive wheels. A substance container is in an emptying position, which is not described in more detail, outside of each of the drive wheels.

With regard to an individual substance container, this substance container is of uniform design with a uniform filling chamber. With regard to a filling of the device with substance containers, this filling is possible only when the cover is removed, thus perpendicular to a displacement direction of the substance containers in the device during conventional operation of the device.

A corresponding device for inhaling powder-type substances is known in the same way from WO 02/053216 A1. However, the substances are located in a cartridge comprising individual chambers. A device for inhaling powder-type substances is likewise known from US 2010/294278 A1. The substances are located in individual blister packs, which, in turn, are accommodated in a blister rotary part. For emptying purposes, a blister pack is initially guided out of the rotary part and is then pierced open. A device for inhaling powder-type substance is likewise known from EP 2 115 595 A2 EP 211 595 A2, in the case of which individual blister packs are accommodated in a cartridge in the same way. The cartridge is moved by means of a carriage-shaped drive part. In an emptying position of a blister pack, the blister pack is located in the cartridge.

SUMMARY OF THE INVENTION

Based on the above-described prior art, the invention has the object of further improving a device of the discussed type in an advantageous manner. In addition, it has the object of specifying a new and advantageous substance container for such a device, and to improve a method for filling such a device comprising substance containers of this type.

This object is initially solved in the case of a device, which focusses on that the substance container in the emptying position is located in an accommodating molding of the drive wheel.

As a result of the preferably provided loose arrangement of a plurality of substance containers in the device, substance containers comprising, for example, different substances and/or different dosages, can be capable of being arranged in the device in a possible design. For example, the dosage of substance containers that are arranged directly one behind the other can thus further rise successively, for example to a medically necessary level, and can optionally sink again successively with the last substance containers in the inhalation sequence.

An individual equipping of the device is made possible by means of the separate arrangement of the substance containers.

Even if the substance containers are not connected to one another, they can optionally move in a chain-like manner in the device or in the guide mechanism of the device, respectively, in particular as a result of the contact of two respective immediately consecutive substance containers with one another in the displacement direction. As a result of the contact with one another, a movement of a substance container triggered in particular from the outside by the user, for example into an emptying position, leads to a contact pressure propagating over the substance containers. A substance container, which is set directly in motion, optionally actively from the outside, preferably via the drive wheel, can quasi push the entire further row of substance containers in front of it.

Due to the captured position of the substance container in the accommodation molding of the drive wheel, a specified emptying position, which can thus in each be assumed in a defined manner in the course of a plurality of inhalations, of the substance container can thus be reached. The assumption of the emptying position is thereby preferably independent of the containers, which move up in the transport direction and which thus otherwise apply a contact pressure for displacing the substance container in the guide mechanism. On the contrary, the substance container that is brought into the emptying position can be—temporarily—decoupled from the direct contact pressure propagating chain in order to assume this position in a defined manner.

With regard to a substance container, the object is solved in that the substance container has two sub-regions, which each separately have an amount of substance, and that both sub-regions have an openable pierceable cover.

As a result of this design, a new and advantageous substance container is created. The latter makes it possible to accommodate two portions of a powder-type substance in the same substance container. The portions can be different with regard to their composition.

Such a substance container, the sub-regions of which can also preferably be opened simultaneously for inhalation, lends itself in particular in the case of different pharmaceutical substances, which are suitable for inhalation, but which are to be mixed only directly in the course of the inhalation in order to improve the effect. Each of the different substances is accommodated in a separate cavity of the substance container as portion. In an advantageous manner, both sub-regions can each have an openable cover. Such an opening can take place in the device by means of an insertion mechanism.

In the case of a corresponding formation of the device, such a substance container also makes it possible to optionally open only the one or the other sub-region in the course of an inhalation process, and to evacuate it in the course of the inhalation with the arriving air flow, or, as a further alternative both sub-regions.

With regard to the method for filling a the device, tin a first method step, the substance containers are introduced into a storage chamber of the device through a separate housing opening when the device is already essentially assembled, that a guide mechanism for the substance containers in the form of a guideway is formed in the device, and that the substance containers in the guideway are inserted in a transport direction, which is also given during conventional use of the device, and that, in a second method step, the separate housing opening is closed by means of a the closure part, which can no longer be removed without destruction.

It is made possible by means of the proposed method to separate production and assembly of the device on the one hand, as well as filling of the device on the other hand in a spatial and/or temporal manner. With the exception of the closure part, the device can nonetheless be assembled in a complete and operable manner. The substance containers can thereby be successively inserted into a possible guide mechanism within the device, for example by means of a slider, on which or in which the substance containers can be provided so as to be arranged one behind the other in a possible design.

In the case of the device for inhaling powder-type substances, comprising a substance container accommodated in the device, and an insertion mechanism, wherein the insertion mechanism is formed for opening the substance container, the substance container can have two sub-regions, and a partial amount of the substance of the substance container can be contained in each sub-region. The sub-regions are furthermore separate from one another, each sub-region has a pierceable cover that can be opened by means of the insertion mechanism, and the partial amount of each of the sub-regions can only be emptied through the punctured cover assigned to this sub-region.

According to a possible design, the substance containers can form a continuous row in the guide mechanism of the device. Even though the substance containers are preferably not connected to one another, a continuous chain-like arrangement of the substance containers results in the device in the case of such a design. The guide mechanism can in particular be formed only with a width, which is specified transversely to a direction of movement of the substance containers in the guide mechanism, so that only an arrangement one behind the other—based on the direction of movement—of the substance containers in the guide mechanism is possible. The substance containers are thus preferably accommodated in one row one behind the other in the device and are preferably moved in one row one behind the other in the device.

According to the proposed method, the last substance container to be inserted can quasi close the above-described continuous chain of the substance containers during the equipping of the device with the individual substance containers. The last substance container can ultimately ensure that in response to a movement of the substance container chain, the contact pressure propagates over all substance containers. This contact pressure can optionally be present in the direction of a usual displacement direction of the substance containers as well as in a direction opposite thereto.

A drive element can be provided, via which a or selected substance containers can be acted on to move the substance containers. The drive element can act directly or also indirectly on the one or the several selected substance containers, so that they are actively moved, while the further substance containers in the guide mechanism move via the propagating contact pressure below the substance containers.

The drive element can thereby be formed as above-described drive wheel, comprising radially open accommodating moldings, for acting on a respective substance container. The drive wheel can be formed in the form of a star wheel, having the above-described accommodating moldings.

In preferred design, only one (numeral) drive element, in particular drive wheel, is provided in the device, which more preferably acts directly at least on the substance container, which is to be moved into the emptying position. In addition, the drive wheel can optionally also act on one or two, optionally three or four or more, substance containers upstream of and/or downstream from the substance container, which is in the emptying position (based on the displacement direction of the containers).

A substance container can be caught completely or also only partially in an accommodating molding. The wall of the drive wheel defining the accommodating molding can thus circumferentially encompass the caught substance container over a section, which makes it possible to guide the substance container and to guide it within the guide mechanism. In a layout, in which the geometric axis of rotation of the drive wheel preferably presents itself as point, the accommodating molding can thus have an outer edge course in the shape of the segment of a circle, for interaction with a, for example, circular cylindrical section of the substance container.

The drive element, in particular the drive wheel, can be moved in a preferably specified transport direction by means of a drive part that can be moved by the user. A displacement of the drive element opposite the transport direction is preferably prevented. The user deliberately moves the drive part, in particular to displace the substance container in the direction of the emptying position. In a further design, an insertion mechanism can also be displaced in such a way via the drive part that the cover of the substance container can be punctured to open the substance container.

The drive element can thereby be arranged coaxially and rotationally connected to an actuating wheel. It can further be provided in this context that the drive element and the actuating wheel are arranged in a rotationally fixed manner on a drive shaft. According to a possible design, the geometric axis of rotation of such a drive shaft can be aligned essentially perpendicularly to the direction of movement of the substance containers in the guide mechanism. The guide mechanism can thereby further be arranged so as to surround the drive shaft in a web-like manner.

The actuating wheel can be acted on directly or indirectly via the drive shaft by means of the drive part. The user can thus act on the drive element and the actuating wheel simultaneously and preferably to the same extent via the drive part.

To prevent a reverse rotation, that is, in particular a rotation opposite the specified direction of movement of the substance containers in the guide mechanism, the actuating wheel can interact with a non-return device. The actuating wheel can thus interact, for example, in a ratchet-like manner with a spring-mounted blocking part, which can be run over only in a direction of rotation.

In a manner, which is advantageous with regard to the handling, the drive part can be connected to a closure cap, so that a movement of the drive element takes place in the transport direction in response to movement of the closure cap on a pivoting path into an open position. A displacement of the substance containers over the drive element simultaneously results therefrom in an advantageous manner with a preparation of the device for the inhalation as a result of the pivoting of the closure cap into an open position, which preferably releases a mouthpiece of the device, whereby a substance container is moved into the emptying position in a preferred design. An additional handling is preferably not required thereby. On the contrary, the device is preferably prepared for the inhalation with regard to the positioning of the substance container by pivoting the closure cap into the open position.

The need may exist to stress the actuating wheel only over a portion of the pivoting path via the drive part in response to the movement of the closure cap from the closed position into the open position. This in particular with regard to a path, which is only partially given thereby and which the substance containers are to cover, but wherein an optionally longer path is required for actuating the insertion mechanism. For this purpose, the drive part can engage with the actuating wheel only over a preferably first portion of the pivoting path, and can optionally be disengaged from the actuating wheel over the further portion of the pivoting path.

For this purpose, a slotted guide can be provided, via which the drive part is controlled into the engaged position with the actuating wheel or out of this engaged position in the course of the pivoting movement of the closure cap.

It can thus be preferred in this regard that the drive part is engaged with the drive shaft, which also drives the drive element, and actuating wheel with the help of the slotted guide over a first portion of the displacement path, and is disengaged over a second partial path of the cap movement.

In response to a return movement of the closure cap into the closed position, the drive part can be controlled, in turn, so as to be completely disengaged from the actuating wheel or from the drive shaft, respectively, over the entire pivoting path, which is now passed through in reverse, thus the way back, by means of the slotted guide.

The drive part can thus further be formed so as to be capable of rebounding. The drive part is optionally deflected against the resulting restoring force of the spring via the slotted guide, or is also pushed into a resulting slotted guide section by using the resilient restoring force.

The resilience can be present as a result of the resilient formation of a section of the drive part.

In the closed position of the closure cap, the drive part can be in an initial position, in which the drive part is preferably seated in the slotted guide with little or no spring deflection. In the unused position of the device, which can correspond to a preferred storage position of the device, the spring of the drive part is therefore preferably not or not significantly stressed with regard to its spring force. Due to this preferred design, the resilience of the drive part, which is optionally necessary for the function of the device, does not or does not significantly weaken even in the case of the formation of the drive part with the section, which is capable of rebounding, as plastic part, so that this function is reliable even after a longer non-use of the device.

The guide mechanism for the substance containers can also have a guideway, which communicates with a closable insertion opening for substance containers in the housing. The guideway specifies a directed guidance of the substance containers. The substance containers can thereby be guided on both sides in the guideway in relation to the direction of displacement.

The closable insertion opening, which, in a corresponding open position, allows the guideway to be accessible from the outside, can be provided on the housing side. Substance containers can be inserted into the guideway via the insertion opening, for example, and preferably, for completely equipping the device with a preferably specified number of substance containers.

For example, 15 to 60 such substance containers can be capable of being arranged in the guideway in the device, further for example 20 to 40, further in particular approximately 30 substance containers.

The insertion opening can be capable of being closed by means of a closure part, which can only be removed in a destructive manner. After filling the device with the specified number of substance containers, the closure part is inserted into the insertion opening in such a way that the substance containers are secured against falling out of the guideway and out of the device as a whole. On the outer side, facing the user, the closure part can optically represent a portion of the device housing.

A removal of the closure part after insertion into the insertion opening is preferably only possible by means of a complete or partial destruction of the closure part, wherein even an only partial destruction of the closure part prevents in particular a proper reinsertion of the closure part into the insertion opening.

A corresponding fixation of the closure part can be attained by means of locking rear grip sections in interaction with surrounding housing regions. With regard to this, an adhesion of welding with surrounding housing edge regions can also be provided.

The closure part can, and further preferably, also form a portion of the guideway on the inner side. The guideway facing the closure part can thus form a portion of the guideway wall, optionally, if provided on the guideway side, a section of further guide means, such as, for example, guide webs or the like.

Assigned to an insertion mechanism for a substance container, the guideway can additionally have longitudinal grooves, in which substance, which may have escaped in the insertion mechanism, can collect. For example in the case of an inhalation, which has not been performed, after piercing open the substance container located in the insertion mechanism, the substance can optionally trickle out into the guideway. The substance is preferably collected in the longitudinal grooves of the guideway, so that the displaceability of the substance containers on the guideway is not negatively impacted.

For this purpose, the base and/or the ceiling of the guideway can therefore have groove-like depressions with respect to the contact or sliding surface, respectively, for the substance containers.

The longitudinal grooves can thereby extend over the entire course of the guideway, wherein several longitudinal grooves can optionally be provided in so as to be arranged next to one another. Theses several longitudinal grooves can also be connected to one another via transverse grooves, which run [essentially] transversely to the longitudinal extension of the guideway, in order to thus attain a favorable distribution of substance, which may have trickled out, in the grooves.

Via the guide grooves, substance particles can furthermore also be systematically transferred into a region, in which a collection chamber is formed, which is preferably formed separately from the guideway. The substance transported in the longitudinal grooves can optionally be collected in this collection chamber. It can thus be attained that the substance is ultimately optionally brought completely out of the region of the guideway.

The substance container can be formed essentially cylindrical, more preferably circular cylindrically.

In the case of such a design, the two sub-regions of the substance container can in each case be provided on the end side, in relation to a longitudinal axis of extension of the cylindrical substance container, so that they can be arranged opposite one another, viewed in the direction of extension of the axis.

The sub-regions of the substance container can be separated from one another via a base, which extends essentially in a transverse plane to the longitudinal axis.

To attain a favorable evacuation of the sub-regions (cavities) by means of the air flow, the sub-regions can in each case be formed in the manner of a half shell, so that preferably no dead zones appear in terms flow. For this purpose, the sub-regions can have a bottom area, which is formed to be curved continuously. This continuous curvature is preferably also present in the same way in all possible cross sections, which are present in the direction of the longitudinal axis.

It turns out to be advantageous in this context when the substance container, based on a cylinder longitudinal axis, has an outer circumferential groove, which is aligned transversely to the cylinder axis, approximately in the center. Approximately identical wall thicknesses of the container even in the central region, which has the base separating the sub-regions from one another, result as a result of the formation of such a groove, in particular in connection with the design of the sub-regions in the shape of a half shell and in relation to a longitudinal section through the substance container, in which longitudinal section the longitudinal axis presents itself as line. Without the provided groove, incidence phenomena can optionally emerge, in particular in the case of substance containers, which are produced as plastic injection-molded parts, in the case of a locally high (excessive) wall thickness, as they would appear in the central region. In addition, this results in material and weight savings.

The substance container thus preferably further consists of a hard plastic, such as, for example, polypropylene or also polyethylene.

The groove on the wall outer side, which extends in the circumferential direction, which is optionally provided at the substance container, can additionally further also be used to guide the substance container in the guideway, for example as a result of an engagement of a guide web with the groove, on one or both sides of the substance container in relation to a layout, in which the longitudinal axis presents itself as dot.

The cover, which covers the respective sub-region of the substance container and which can be punctured, can, and also preferably, consists of a foil, for example an aluminum foil. The foil can thereby be welded to a front edge of the substance container or to an edge surrounding the sub-region, respectively. In particular ultrasonic welding is preferably used thereby.

Prior to the welding of the foil, the corresponding front edge of the substance container can thereby have individual webs, for example webs aligned radially in relation to the longitudinal axis, which melt in the course of the welding process and which connect to the foil by equalization over the entire front wall.

It goes without saying that the portioned substance, which is to be stored in the cavity, is introduced prior to welding the foil in order to cover the cavity.

The substance containers are inserted into the guide web via the insertion opening in a direction of movement, which is also at hand in response to the common use of the device, so that an optionally provided non-return device does not prevent the insertion.

BRIEF DESCRIPTION OF THE DRAWINGS

The invention is described below on the basis of the enclosed drawing, which, however, only represents exemplary embodiments. A part, which is described only based on one of the exemplary embodiments and which is not replaced by a different part in the case of a further exemplary embodiment due to the special feature emphasized there, is thus also described for this further exemplary embodiment as at least possible part, which is present. In the drawing:

FIG. 3 shows the enlargement of the region III prior to closing a housing-side insertion opening by means of a closure part;

FIG. 4 shows a substance container for the device in perspective individual illustration;

FIG. 5 shows the top view according to arrow V in FIG. 4;

FIG. 6 shows the view according to arrow VI in FIG. 4 against the substance container;

FIG. 7 shows the section according to line VII-VII in FIG. 6;

FIG. 8 shows the enlargement of the region VIII in FIG. 7, when the cover is fixed to the substance container;

FIG. 9 shows a detailed sectional illustration essentially corresponding to FIG. 8, but relating to a situation prior to fixing the cover to the substance container;

FIG. 10 shows a perspective detailed illustration of the substance container, partially cut, relating to the situation according to FIG. 9;

FIG. 14 shows the device in a further exploded perspective illustration;

FIG. 17 shows the arrangement of a drive pinion, of a drive element, and of an actuating wheel arranged in a rotationally fixed manner on a drive shaft, further of a transfer gear and of a counting wheel, in perspective illustration;

FIG. 18 shows the counting wheel and the transfer gear as well as the housing section accommodating the counting wheel and the transfer gear, in perspective exploded illustration;

FIG. 23*a* shows an illustration corresponding to FIG. 23, but relating to an alternative embodiment;

FIG. 27 shows the section according to the line XXVII-XXVII in FIG. 26;

FIG. 28 shows the section according to the line XXVIII-XXVIII in FIG. 26;

FIG. 31 shows the device in perspective illustration, relating to the closure cap open position and thus the inhalation-ready position;

FIG. 32 shows an illustration essentially corresponding to FIG. 31, but partially broken open;

FIG. 36 shows the insertion mechanism in a perspective individual illustration;

FIG. 36*a* shows the insertion direction in a second embodiment;

FIG. 36*b* shows the enlargement of the region XXXVIb in FIG. 36*a;*

FIG. 37 shows the insertion mechanism in a side view;

Figure 46:
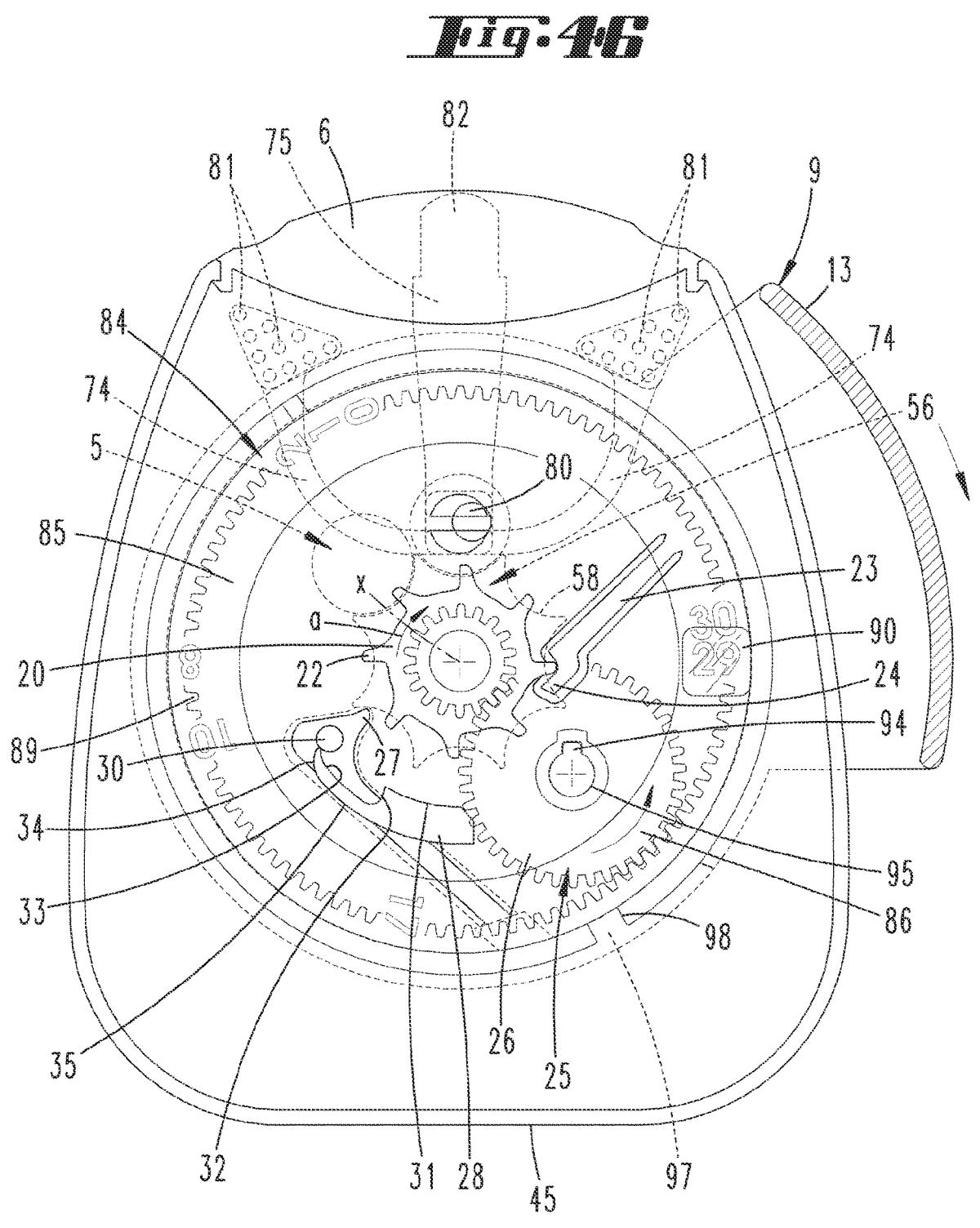

FIG. 46 shows a further follow-up illustration in the course of the pivoting of the closure cap into the open position, relating to the application situation of the insertion means;

DESCRIPTION OF THE EMBODIMENTS

Figure 1:
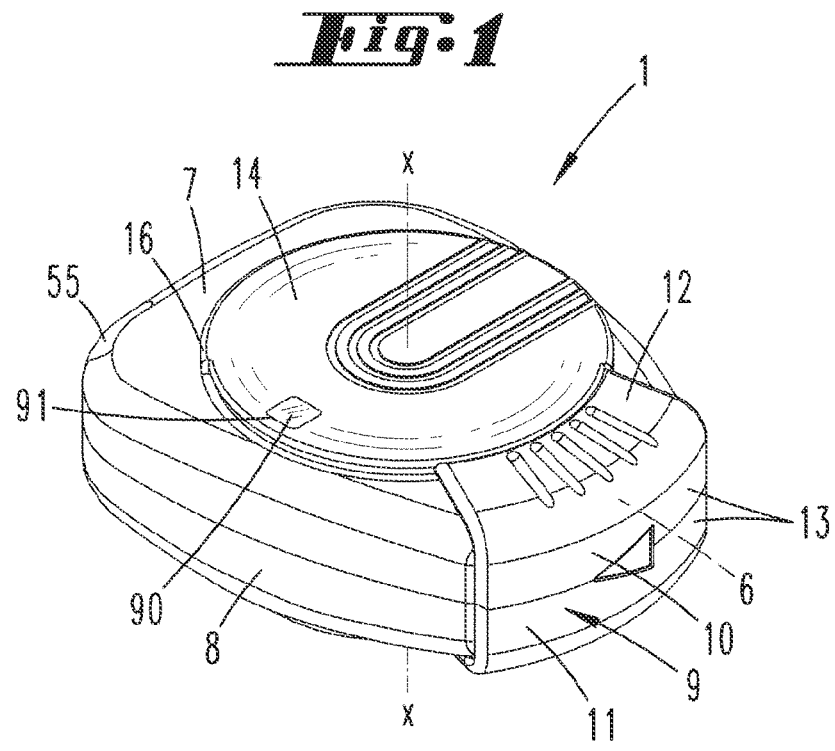
FIG. 1 shows a device for inhaling powder-type substances in perspective illustration, relating to the closed non-use position.
Figure 2:
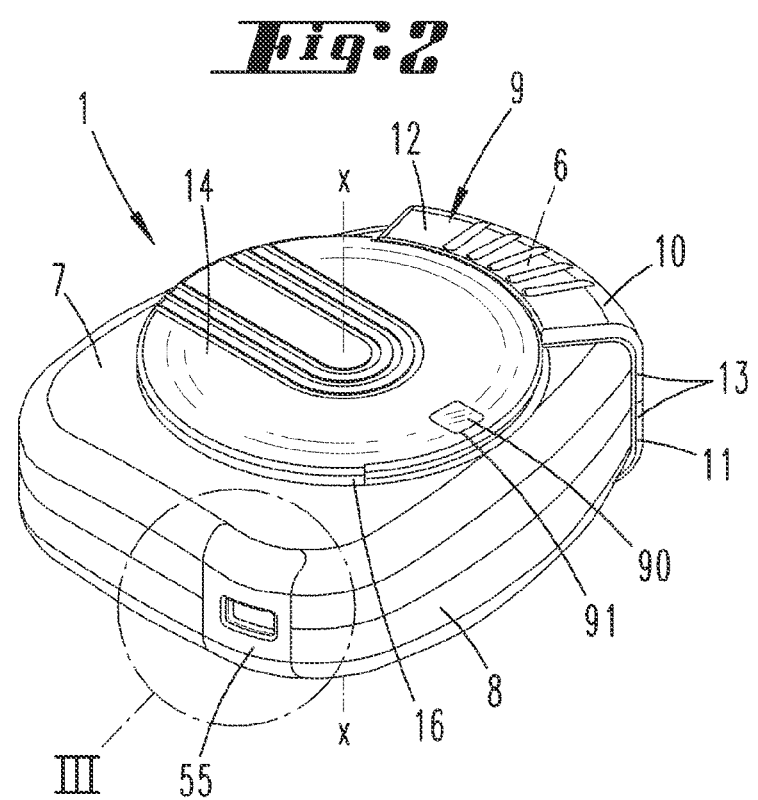
FIG. 2 shows the device according to FIG. 1 in a further perspective illustration.
Figure 11:
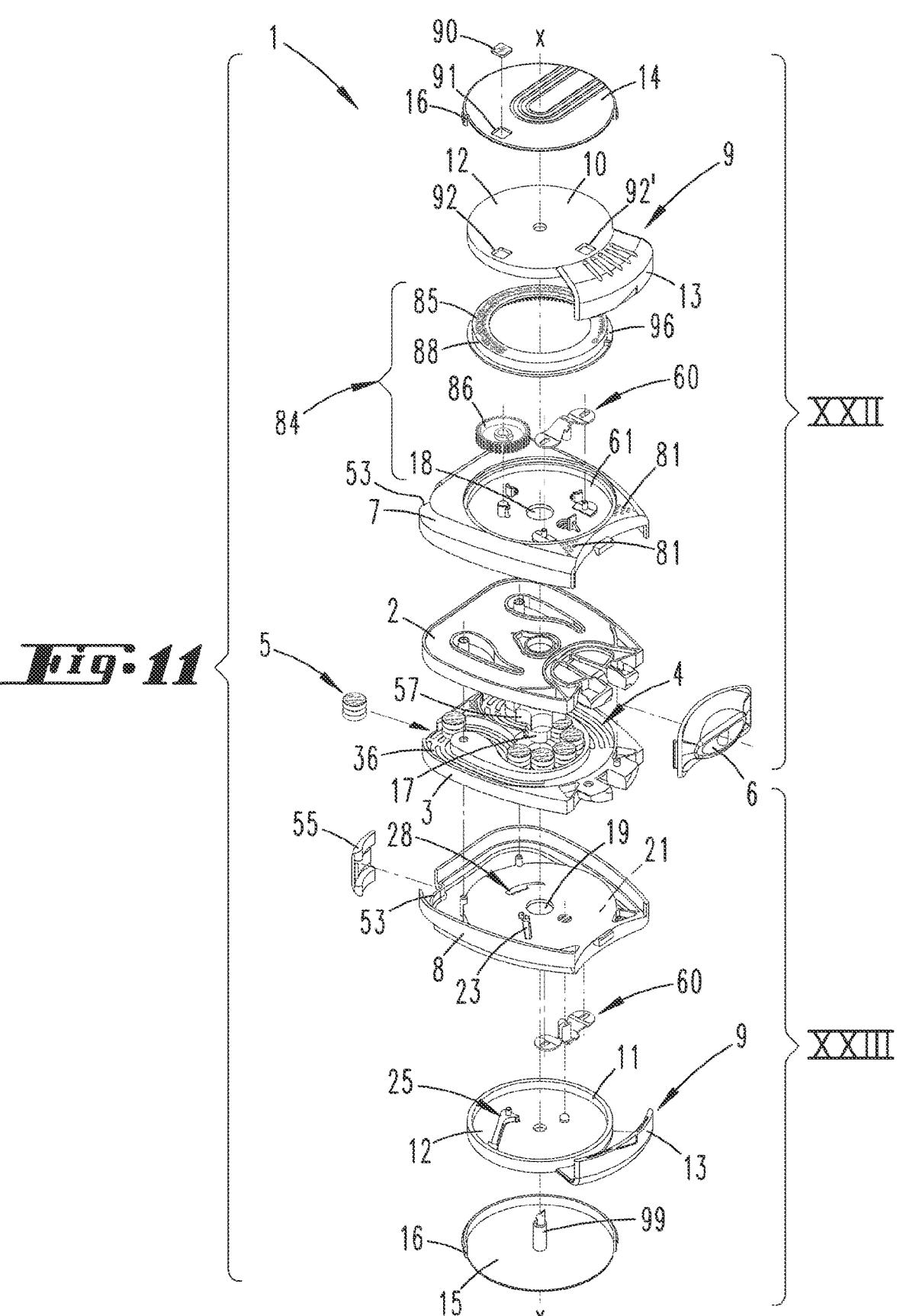
FIG. 11 shows an exploded perspective illustration of the device.
Figure 12:
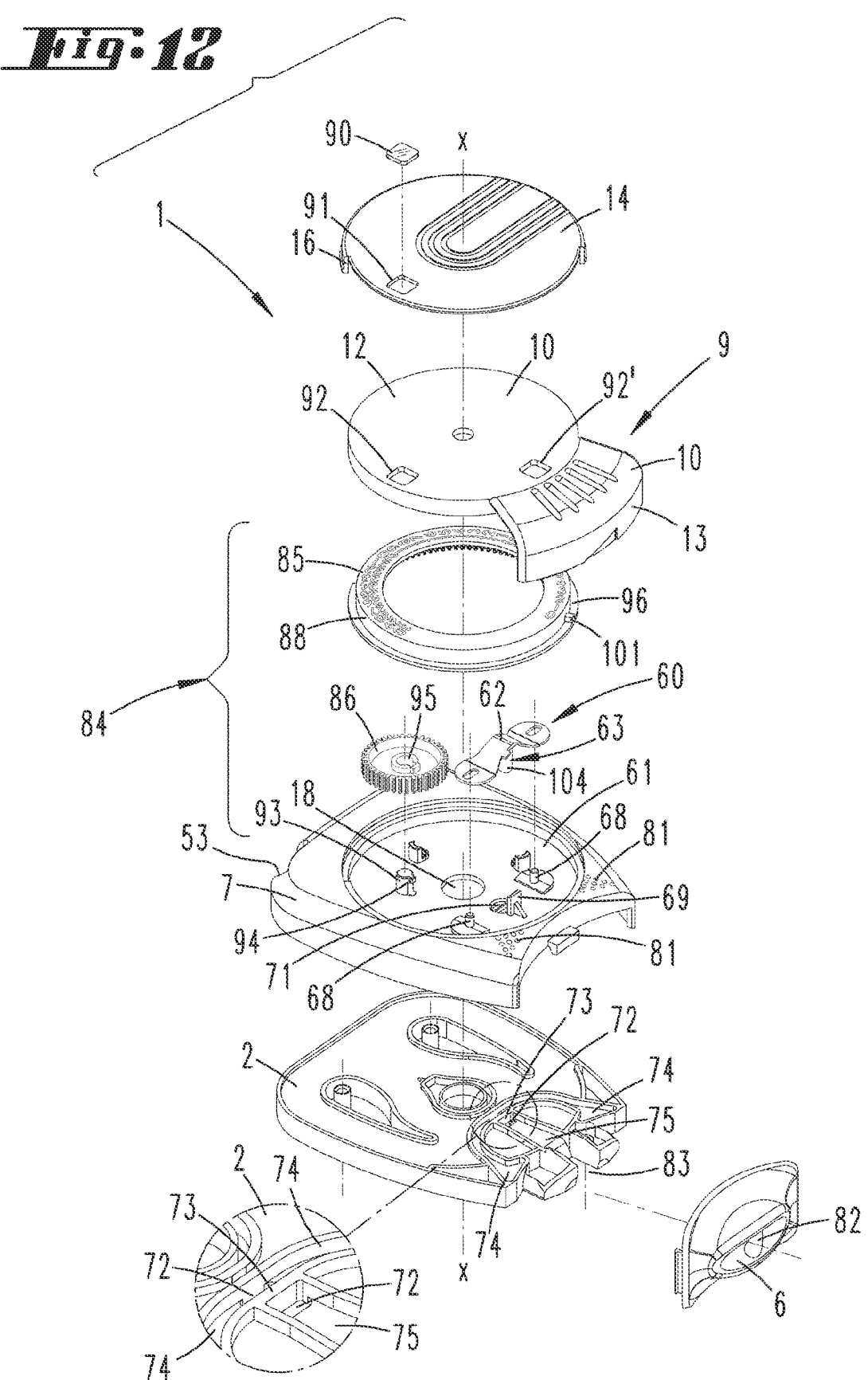
FIG. 12 shows an enlarged exploded perspective illustration of the region XII in FIG. 11.
Figure 13:
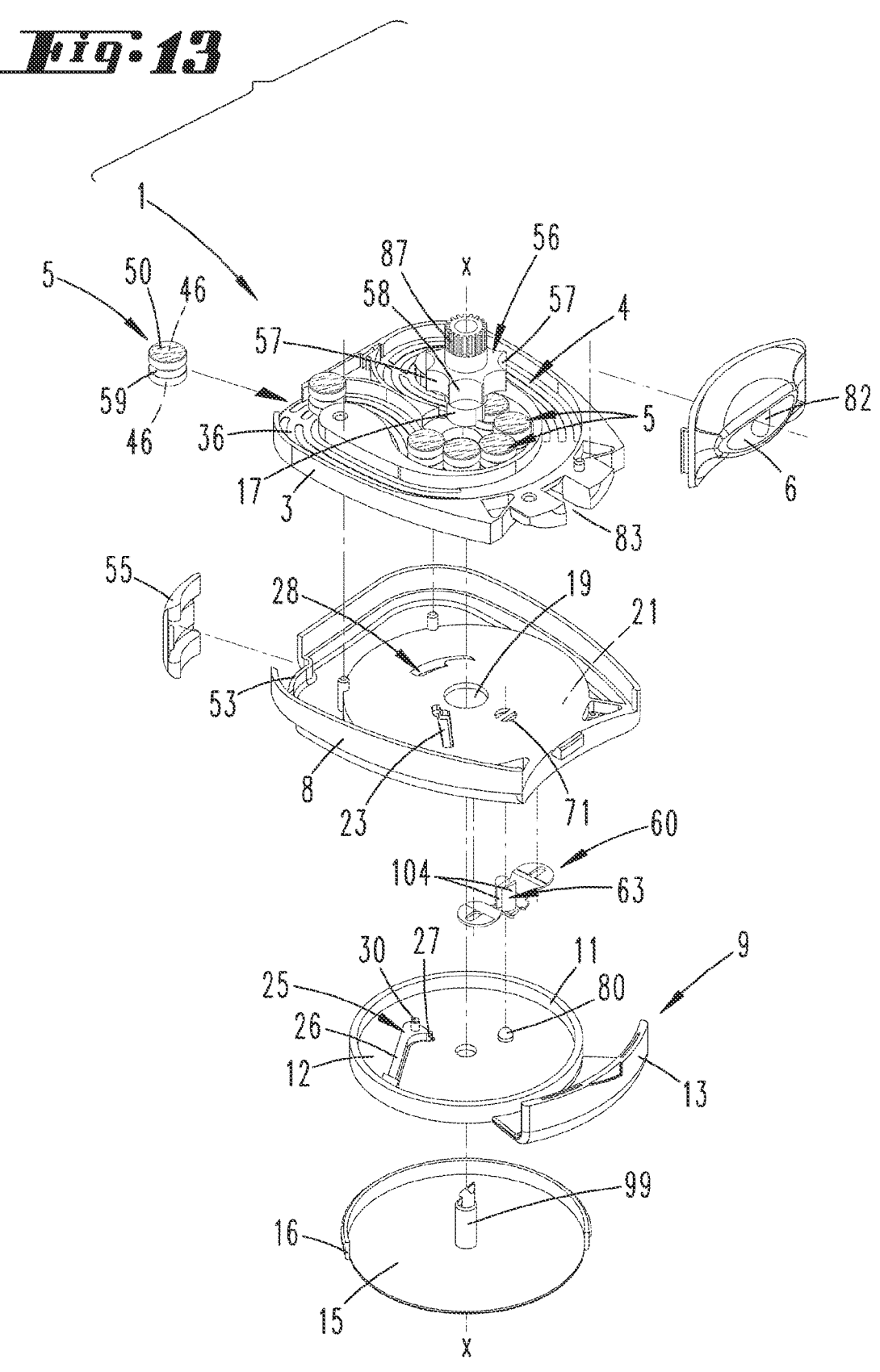
FIG. 13 shows the enlarged exploded perspective illustration of the region XIII in FIG. 11.
Figure 15:
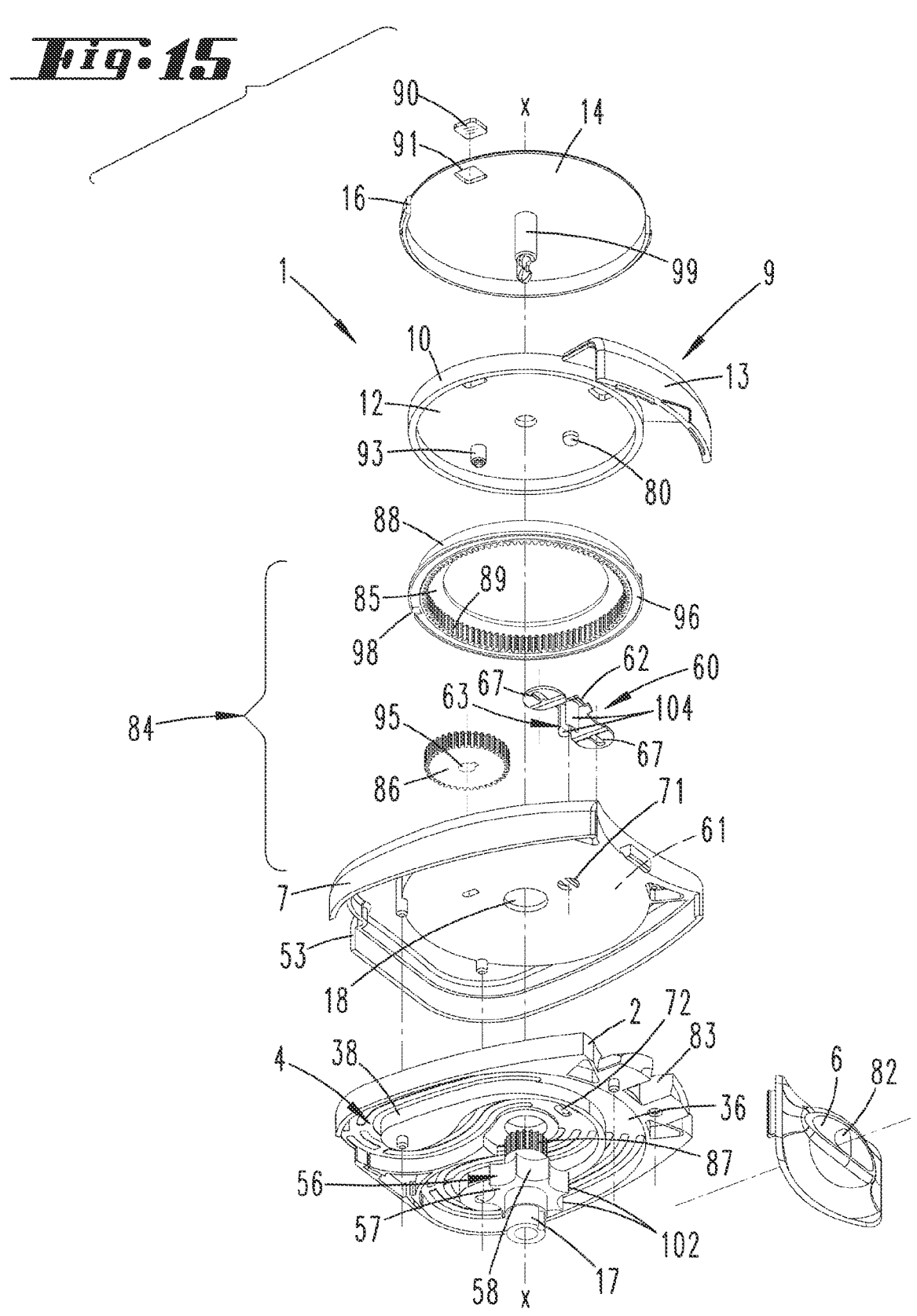
FIG. 15 shows an enlarged exploded perspective illustration of the region XV in FIG. 14.
Figure 16:
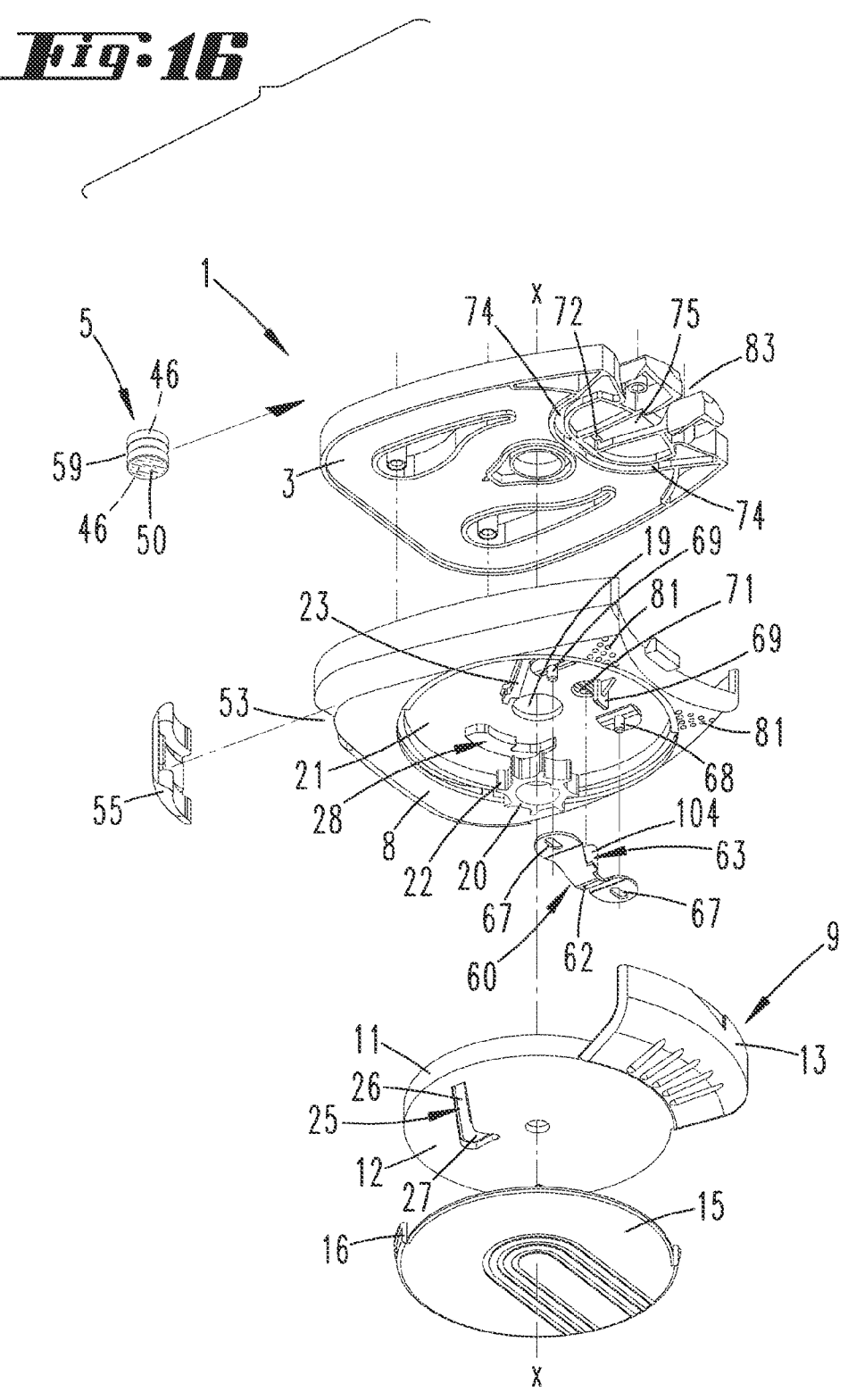
FIG. 16 shows an exploded perspective illustration of the region XVI in FIG. 14.
Figure 19:
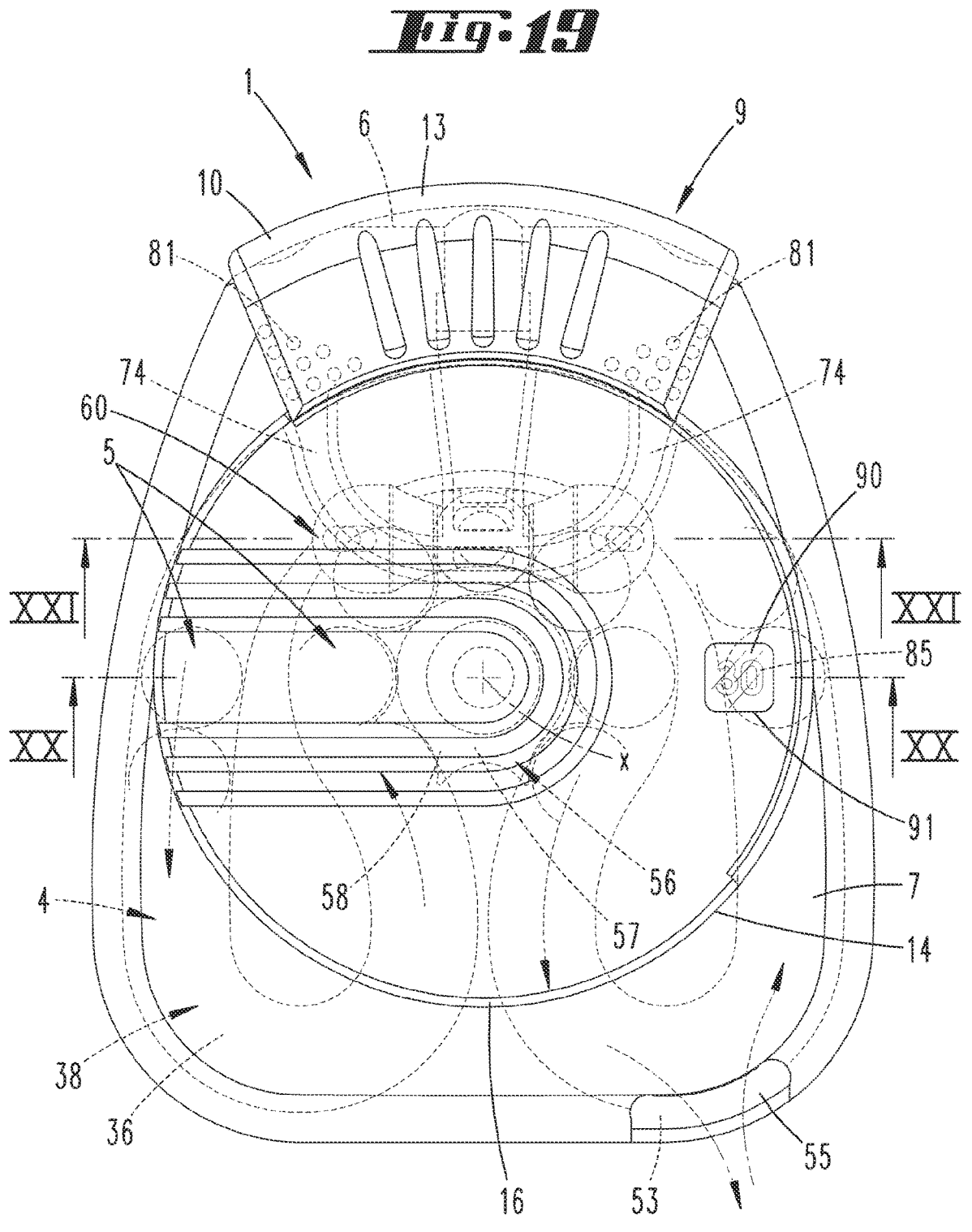
FIG. 19 shows the device in top view, relating to the closed non-use position.

What is illustrated and described, initially with reference to FIGS. 1 and 2 as well as 11, is a device 1 for inhaling powder-type substances 48, 48'. The device 1 preferably has a mouthpiece 6, further an insertion mechanism 60 comprising insertion means 63, for opening a substance container 5, wherein preferably a plurality of substance containers 5 that can be moved successively into an emptying position P are provided, which are accommodated so as not to be connected to one another in direct contact with one another in a guide mechanism 4 attached to the device. A counter 84 is provided for counting and displaying the performed or still remaining inhalation processes.

The essential parts of the device 1 listed below can, and preferably, consist of a plastic, in particular hard plastic, such as polypropylene or polyethylene.

As can in particular be seen from the exploded perspective illustrations in FIGS. 12 to 17, the device 1 can initially essentially consist of a housing inner top part 2 and a housing inner bottom part 3, which, in direct contact with one another, leave the guide mechanism 4 for the substance containers 5 between them.

A mouthpiece 6, via which the inhalation process can be performed as a result of breathing in, is arranged at these housing inner parts 2 and 3.

A housing shell top part 7 as well as a housing shell bottom part 8, which, in direct contact with one another, accommodate the housing inner parts between them, essentially along outer edges facing one another, is further part of the device 1.

Together with the mouthpiece 6, housing shell top part 7 and housing shell bottom part 8 essentially form the outer contour of the device 1.

A closure cap 9 for the mouthpiece 6 is also essentially part of the device 1. The closure cap 9 is essentially formed from two closure cap parts, which are in each case assigned to the housing shell top part 7 and the housing shell bottom part 8, namely a closure cap top part 10 and a closure cap bottom part 11.

Each closure cap part thereby has a plate-like cover section 12 and a cap section 13, which protrudes outwards from this cover section 12 and which is formed in an L-shaped manner in a cross section.

Along the free outer edges of the L-shaped cap sections 13, which face one another, they can be connected to one another, for example as a result of an adhesion or welding, so that a cap with an essentially U-shaped cross section for covering the mouthpiece 6 results as a whole.

The ceiling sections 12 are provided in parallel alignment to one another and can be pivotably displaced around a geometric pivot axis x relative to the housing inner parts and the housing shell parts.

In addition, the closure cap top part 10 can be covered by a plate-like cover part 14, and the closure cap bottom part 11 can be underpinned by a likewise preferably plate-like base part 15.

The terms "top" and "bottom" or "base" or "cover", respectively, used with regard to the above-described housing refer solely to the graphic illustrations for example in FIGS. 12 to 17. In the case of the proposed device 1, a preferred alignment of the device for attaining a correct handling preferably does not result. For example, the top side can thus in fact also form the bottom side of the device 1 during the use.

Base part 15 and cover part 14 can, and as is illustrated, in each case have a collar 16, which partially revolves around the pivot axis x. The free front edges thereof, which point in the circumferential direction, can in each case provide a pivot stop for the closure cap 9 in the closure cap closed position and in the closure cap open position. The pivot angle of the closure cap 9 is therefore limited, thus for example to a pivot angle of approximately 50 to 70 degrees, preferably approximately 60 degrees.

Aligned along the geometric pivot axis x, a drive shaft 17 is provided in the device 1. Said drive shaft can, and also preferably, be pivotably or rotatably displaceable, respectively, relative to the closure cap 9 and the housing 52. The drive shaft 17 can experience a guidance in the region of adapted bores 18, 19 in the housing inner top part 2 and housing inner bottom part 3 or in the housing shell top part 7 and the housing shell bottom part 8, respectively.

The drive shaft 17 can also be accommodated on an axle body 100, which is stationary relative to the drive shaft 17. The axle body 100 can thereby be formed from hollow journals 99, which are in each case centrally molded to the cover part 14 and to the base part 15 and which face one another. The hollow journals 99 can, and preferably, be interlocked in such a way that the housing 52, which is tightly locked thereby as a whole, can preferably no longer be opened without destruction.

The drive shaft 17 can be driven in a ratchet-like manner via the closure cap 9 in such a way that, as a result of a pivoting displacement of the closure cap 9, in particular from a basic position, which closes the mouthpiece 6, into an open position, the drive shaft 17 is rotationally displaced by a specified angular dimension. A return pivoting displacement of the closure cap 9 from the open position into the closed position preferably does not effect a rotary entrainment of the drive shaft 17.

For this purpose, the drive shaft 17 is connected in a rotationally fixed manner to an actuating wheel 20. In the illustrated exemplary embodiment, said actuating wheel sits in a trough-like depression 21 of the housing shell bottom part 8 between this shell bottom part and the closure cap bottom part 11.

The actuating wheel 20 can, and as is illustrated, have essentially radially protruding entrainment protrusions 22. In the illustrated exemplary embodiment, eight such entertainment protrusions 22 are provided so as to be distributed evenly over the circumference, wherein each entrainment protrusion 22, deviating from a strict radial to the geometric pivot axis x, can draw an acute angle of approximately 20 to 30 degrees, so that an imaginary center line in relation to a top view, for example according to FIG. 42, can intersect the actuating wheel 20 in a secant-like manner by means of an entrainment protrusion 22.

In the region of the depression 21, the actuating wheel 20 interacts with a non-return device 23. The latter can, and as is illustrated, be formed as resilient section of the housing shell bottom part 8, integrally with the latter.

The non-return device 23 is provided with a locking lug 24, for interaction with the entrainment protrusions 22 of the actuating wheel 20, wherein the locking lug 24 can further be formed in such a way that it can be overrun by the entrainment protrusions 22 only in the specified direction of rotation a of the actuating wheel 20. In response to such an overrunning, the locking lug 24 rebounds accordingly.

Such an overrunning is not possible against the direction of rotation a. On the contrary, the locking lug 24 of the non-return device 23 blocks a rotation of the actuating wheel 20 in this direction.

The actuating wheel 20 and via the latter, the drive shaft 17, is rotationally movable as a result of the impact of a drive part 25 on one of the entrainment protrusions 22 of the actuating wheel 20. The drive part 25 can, and preferably, be part of the closure cap 9, in particular part of the closure cap bottom part 11.

The drive part 25 can thereby be formed integrally and of the same material as the corresponding closure cap bottom part 11. The drive part 25 can thereby further have a spring arm 26, which is rooted on the cover section 12 and which forms a protrusion-like entrainment lug 27 on the end side. This entrainment lug 27 is suitable for interacting with an entrainment protrusion 22 of the actuating wheel 20.

As a result of the arrangement of the entrainment lug 27 on a spring arm 26, the entrainment lug 27 is designed so as to be resiliently deflectable essentially transversely to the longitudinal extension of the spring arm 26.

Figure 42:
FIG. 42 shows an essentially schematic top view illustration onto the device, relating to the gear-like interaction of the counter and of the drive element for moving a substance container into an emptying position as well as the application of the insertion mechanism as a function of the pivoting displacement of the closure cap, relating to the cap closed position.

In a basic position of the drive part 25, which corresponds to the mouthpiece closed position of the closure cap 9, for example according to FIG. 42, the drive part 25 is inserted in an unstressed manner and preferably without spring deflection in the depression 21. A controlled displacement of the drive part 25 against a restoring force appearing thereby in the region of the spring arm 26 only takes place with the pivoting of the closure cap 9 from the closed position in the direction of the open position.

This control is reached via a slotted guide 28, which is stationary relative to the drive part 25 and the actuating wheel 20. Said slotted guide can, and as is illustrated, be provided on the base side of the depression 21. In addition, the slotted guide 28 can be formed as a rib, which runs essentially concentrically to the pivot axis x and which is stepped in the circumferential direction, wherein said rib initially has a control surface 29 for interacting with a control journal 30, which is molded to the drive part 25 in the region of the entrainment lug 27.

Figure 43:
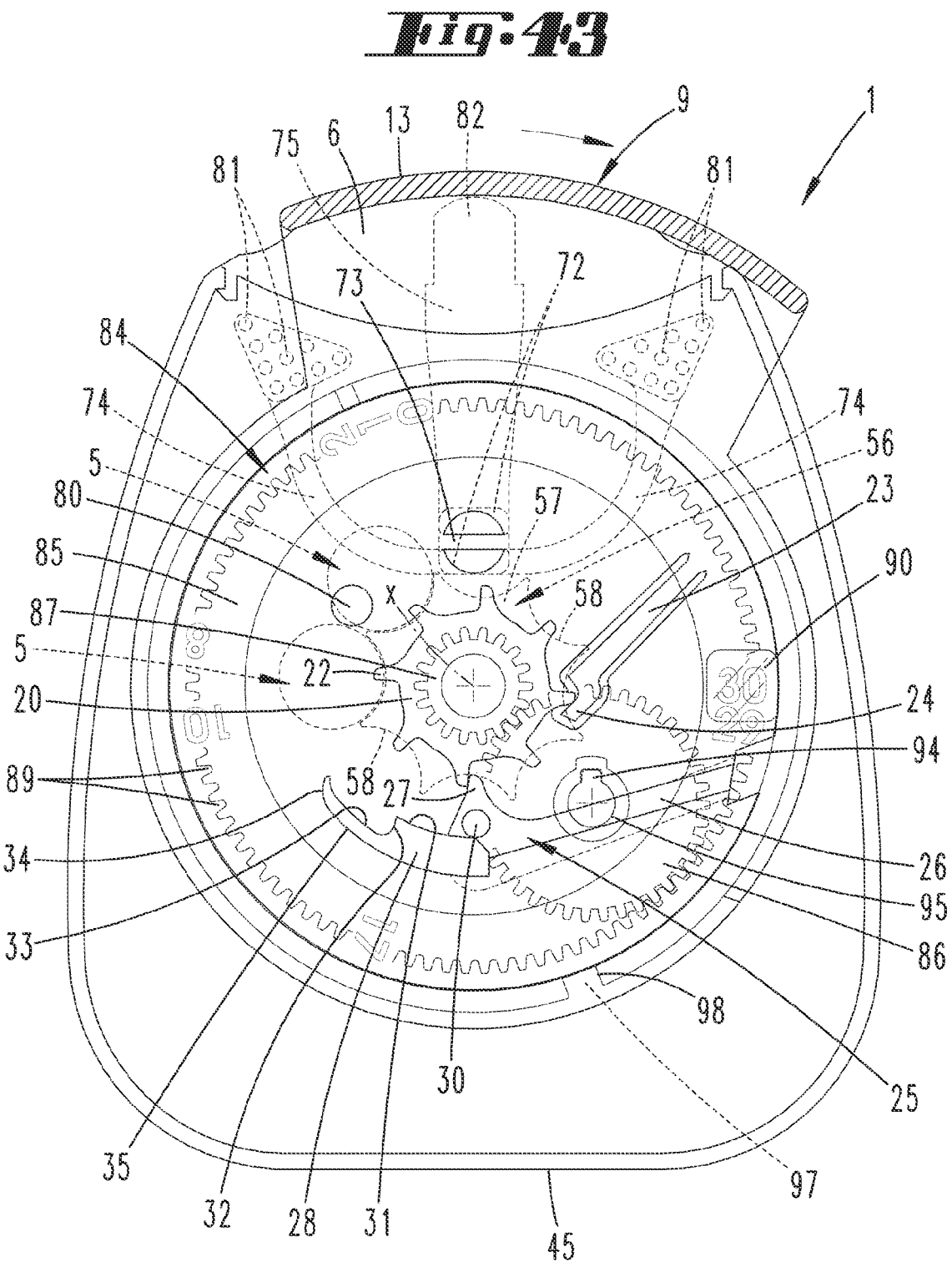
FIG. 43 shows a follow-up illustration for FIG. 42, in the course of the pivoting movement of the closure cap in the direction of the open position.
Figure 44:
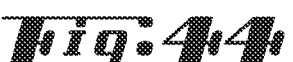
FIG. 44 shows a follow-up illustration for FIG. 43.
Figure 45:
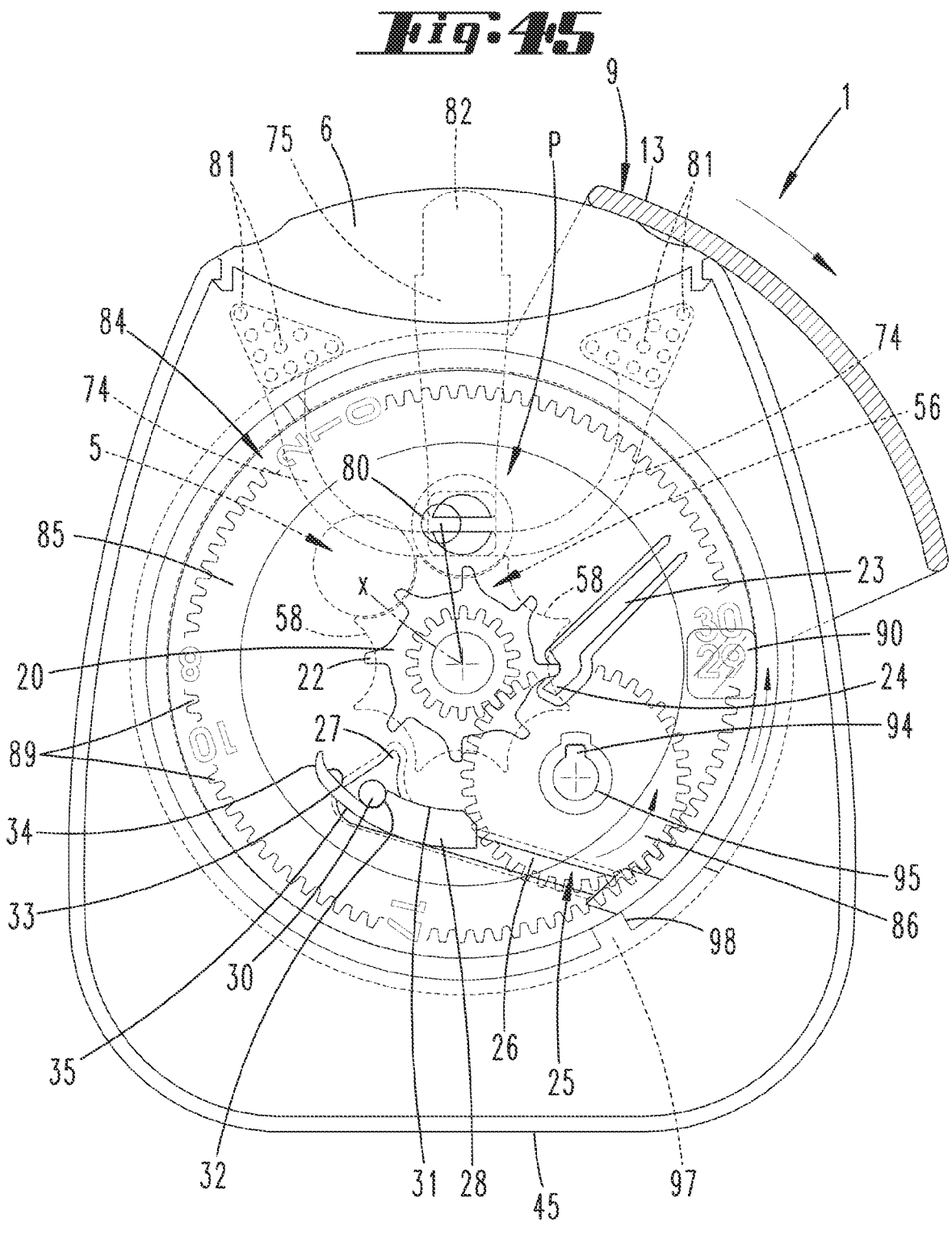
FIG. 45 shows a follow-up illustration for FIG. 44, relating to an intermediate position, in which the substance container has reached the emptying position.

Upon pivoting the closure cap 9 out of the closed position according to FIG. 42, the control journal 30 initially moves against the control surface 29, wherein the control journal 30, and via the latter the entrainment lug 27, is controlled radially to the inside in relation to the pivot axis x under further pivoting displacement of the closure cap 9, by building up a restoring force in the spring arm 26 (see FIG. 43).

The entrainment lug 27 moves into a gap circumferentially between two entrainment protrusions 22 of the actuating wheel 20.

The entrainment lug 27, which, in the course of the further pivoting displacement of the closure cap 9, is guided in the direction of the open position along a first contact surface 31 that runs concentrically to the pivot axis x, in contact with an entertainment protrusion 22, entrains the actuating wheel 20 in the direction of rotation a, via a predetermined angular range, which makes it possible to move a substance container 5 into an emptying position P.

The angle of rotation of the actuating wheel 20 effected via the drive part 25 is preferably smaller than the possible, stop-limited pivot angle of the closure cap 9.

The entrainment lug 27, which is entrained in the course of this further pivoting displacement of the closure cap 9 via the spring arm 26, falls via a step-like recess 32 in the slotted guide 28 onto a second contact surface 33, which is radially offset to the outside relative to the pivot axis x with respect to the first contact surface 31. This drop of the entrainment lug 27 is supported by the restoring force of the spring arm 26. The entrainment lug 27 leaves the interaction region with the entrainment protrusion 22 of the actuating wheel 20, so that the further pivoting displacement of the closure cap 9 does not effect a further rotational influence on the actuating wheel 20.

Figure 47:
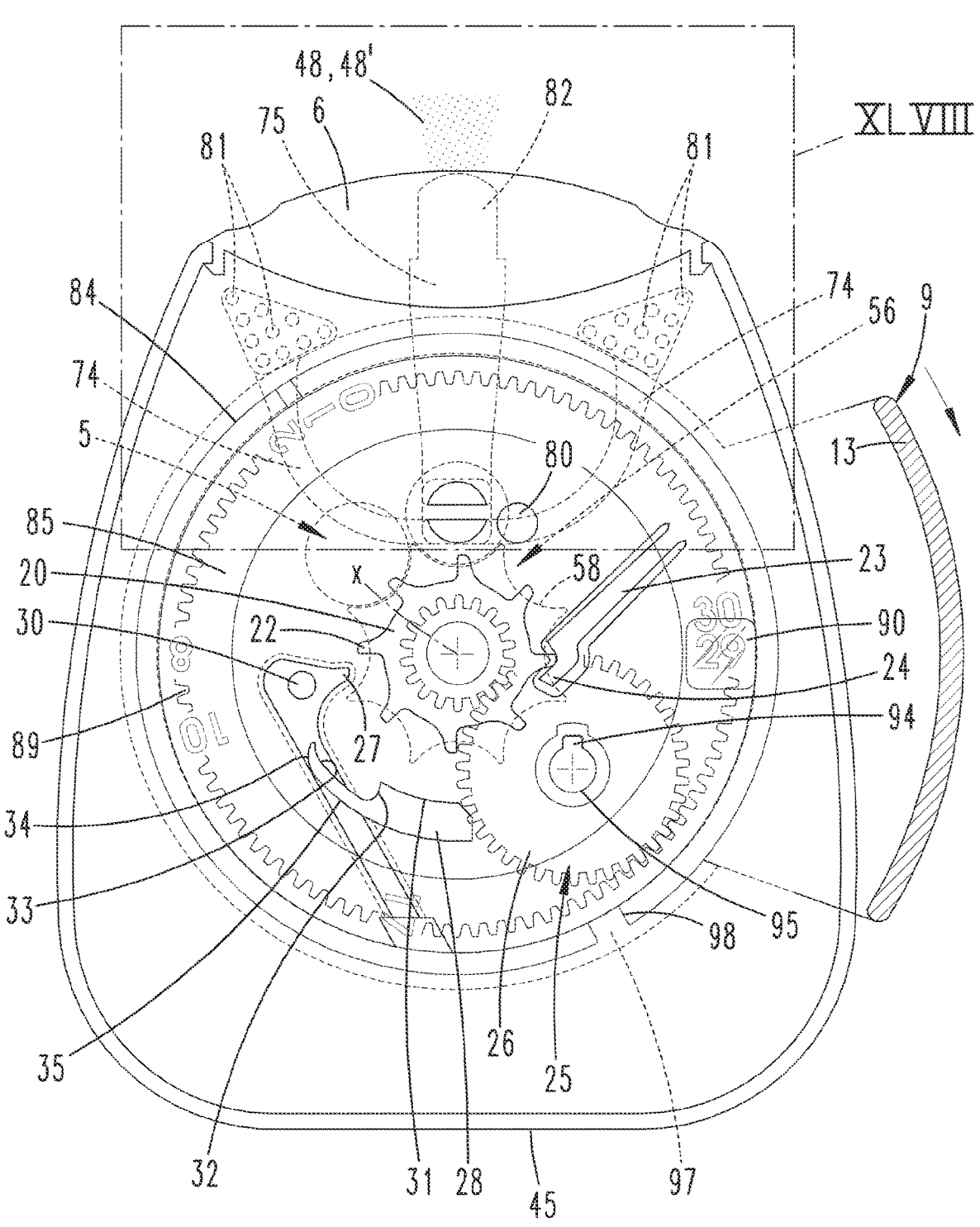
FIG. 47 shows a further follow-up illustration when reaching the closure cap open position.

Upon reaching the closure cap open position according to FIG. 47, the control journal 30 leaves the slotted guide 28, whereafter the drive part 25 can assume a position again, which is relaxed with respect to the spring forces.

The step-like design of the slotted guide 28 further effects that, after a complete rotational displacement of the actuating wheel 20 by the specified angle of rotation, and thus after displacement of a substance container 5 into the emptying position P, the further displacement of the closure cap 9 has to necessarily take place in the direction of the preferably stop-limited open position. A backward displacement of the closure cap 9 can only take place after the slotted guide 28 was left upon reaching the cap open position (according to the position in FIG. 47).

Out of this closure cap open position, the control journal 30 of the drive part 25 is moved—preferably after a previously performed inhalation process—as a result of displacement of the closure cap 9 in the direction of the basic position or in the direction of the mouthpiece closure position according to FIG. 42, respectively, against an end-side further control surface 34, which effects a rebounding displacement of the control journal 30 and thus of the entrainment lug 27 in relation to the pivot axis x radially to the outside, so that, in the course of the further pivoting displacement of the closure cap 9, the control journal 30 is moved in the direction of the mouthpiece closed position along a third contact surface 35, which is radially spaced apart to the outside with respect to the first and the second contact surface 31, 33, once again with respect to the pivot axis x. This results in a spring restoring force, which acts in the opposite direction with respect to the forward displacement of the drive part 25 in the region of the spring arm 26, until the control journal 30 leaves the slotted guide 28 just before reaching the closure cap end position, and assumes the position according to FIG. 42, which is not spring-loaded.

The guide mechanism 4 formed between or through the housing inner top and bottom parts 2, 3, respectively, forms a storage chamber 36 for a plurality of substance containers 5, which are not connected to one another. Housing inner top part 2 and housing inner bottom part 3 each form approximately half of the guide mechanism 4 or the storage chamber 36, respectively, viewed in the direction of extension of the pivot axis x. A U-shaped section can thereby result for each housing inner part in relation to a cross section, in which the pivot axis x presents itself as line, wherein the U-openings point towards one another, and the side walls 37, which limit these U-openings, bear against one another at the front surfaces.

A guideway 38 thus results, which is limited on the top and bottom side as well as laterally by means of the side walls 37 in relation to the pivot axis x, and in the case of which the side walls 37 are spaced apart from one another transversely to the longitudinal extension of the guideway 38, preferably adapted to an outer diameter d of the substance containers 5 to one another.

Figure 22:
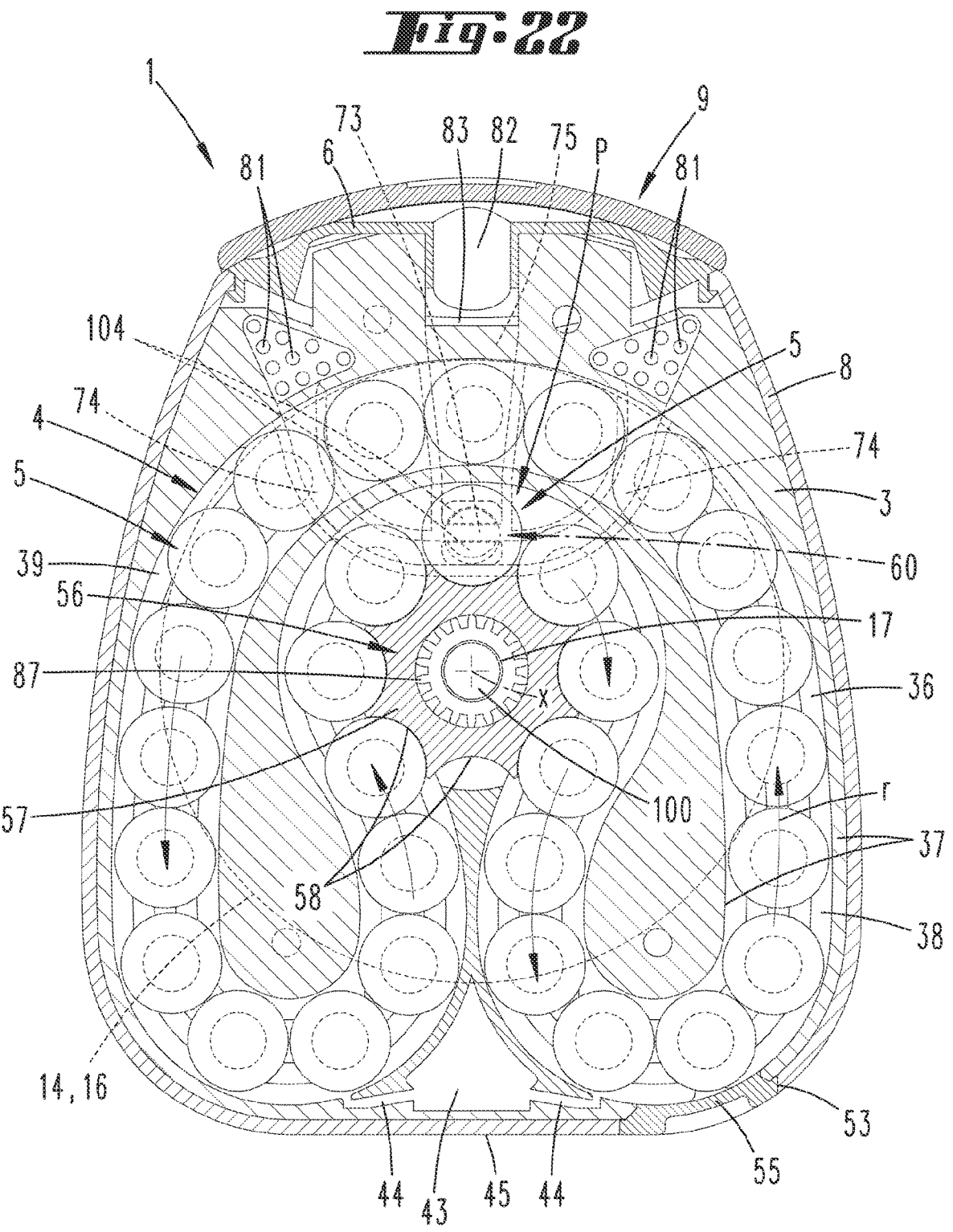
FIG. 22 shows the section according to the line XXII-XXII in FIG. 20.

As can be seen, for example from FIG. 22, the guideway 38 is provided in a meander-shaped manner in the manner of a continuous web in the device 1, thereby forming a loop, which runs concentrically to the pivot axis x, in the region of the pivot axis x.

Starting at this loop, the guideway 38 initially extends on both sides of the loop in the direction of a rear side of the device 1 facing away from the mouthpiece 6, in order to thereafter in each case extend back in the direction of the front region of the device 1 having the mouthpiece 6 over an arc, which is directed to the outside. An arc, which encompasses the loop and which optionally runs concentrically to the pivot axis x, connects the web sections to form a continuous web, which is thus curved, which preferably does not have any sections that run in a stretched-out straight manner.

Longitudinal grooves 41 can, and preferably, be provided over the entire or a majority of the guideway 38 in the region of the web base 39 and/or of the web ceiling 40. For example, two or three longitudinal grooves 41 can thus be provided in this regard, which extend in the longitudinal direction of extension of the guideway 38 and which are thereby spaced apart from one another transversely to the longitudinal extension (see FIG. 23).

These longitudinal grooves 41 can also be connected via transverse grooves 42 in some regions.

Figure 23:
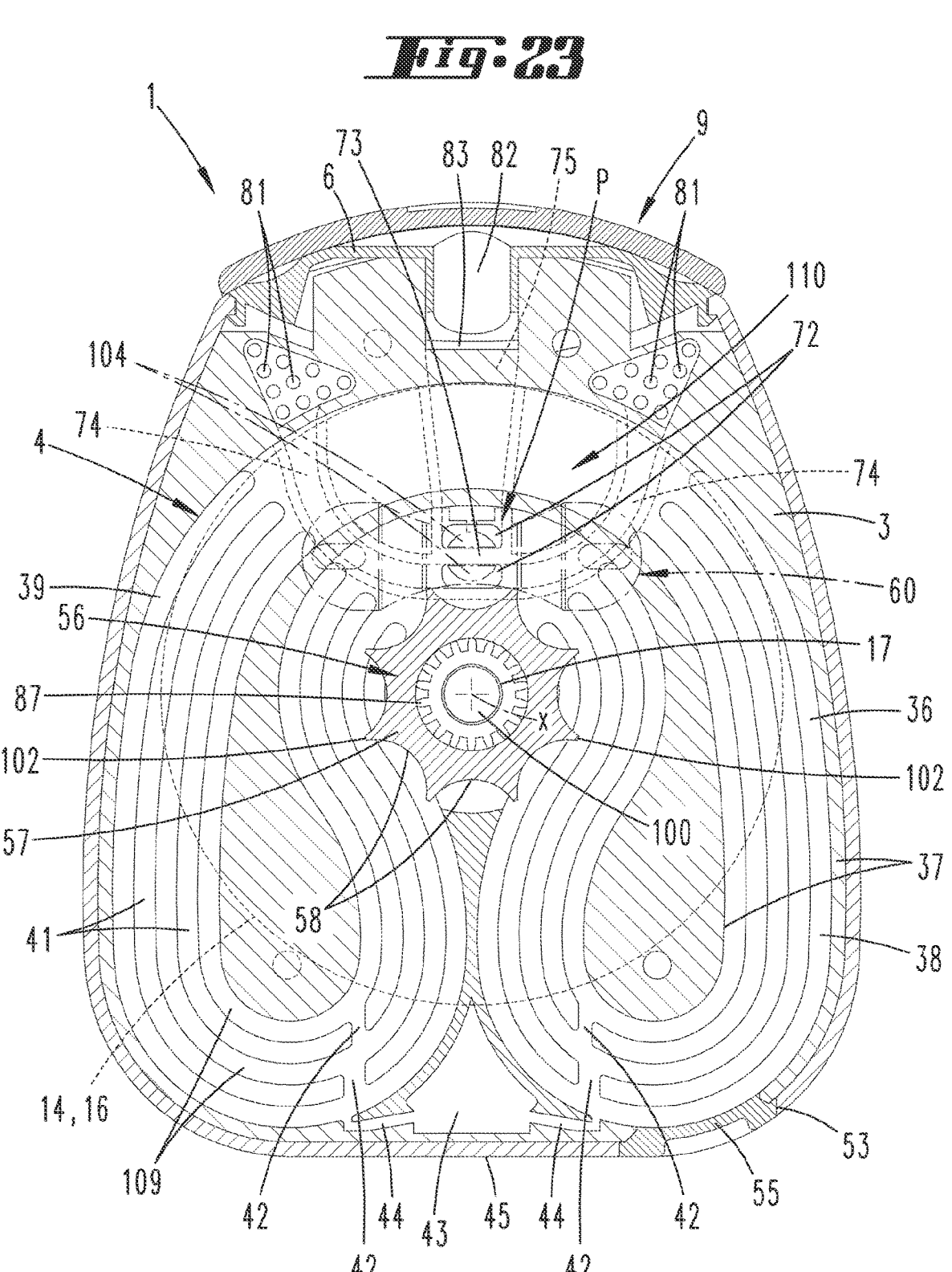
FIG. 23 shows an illustration corresponding to FIG. 22, but without substance containers, which can be accommodated in the device.
Figure 23:
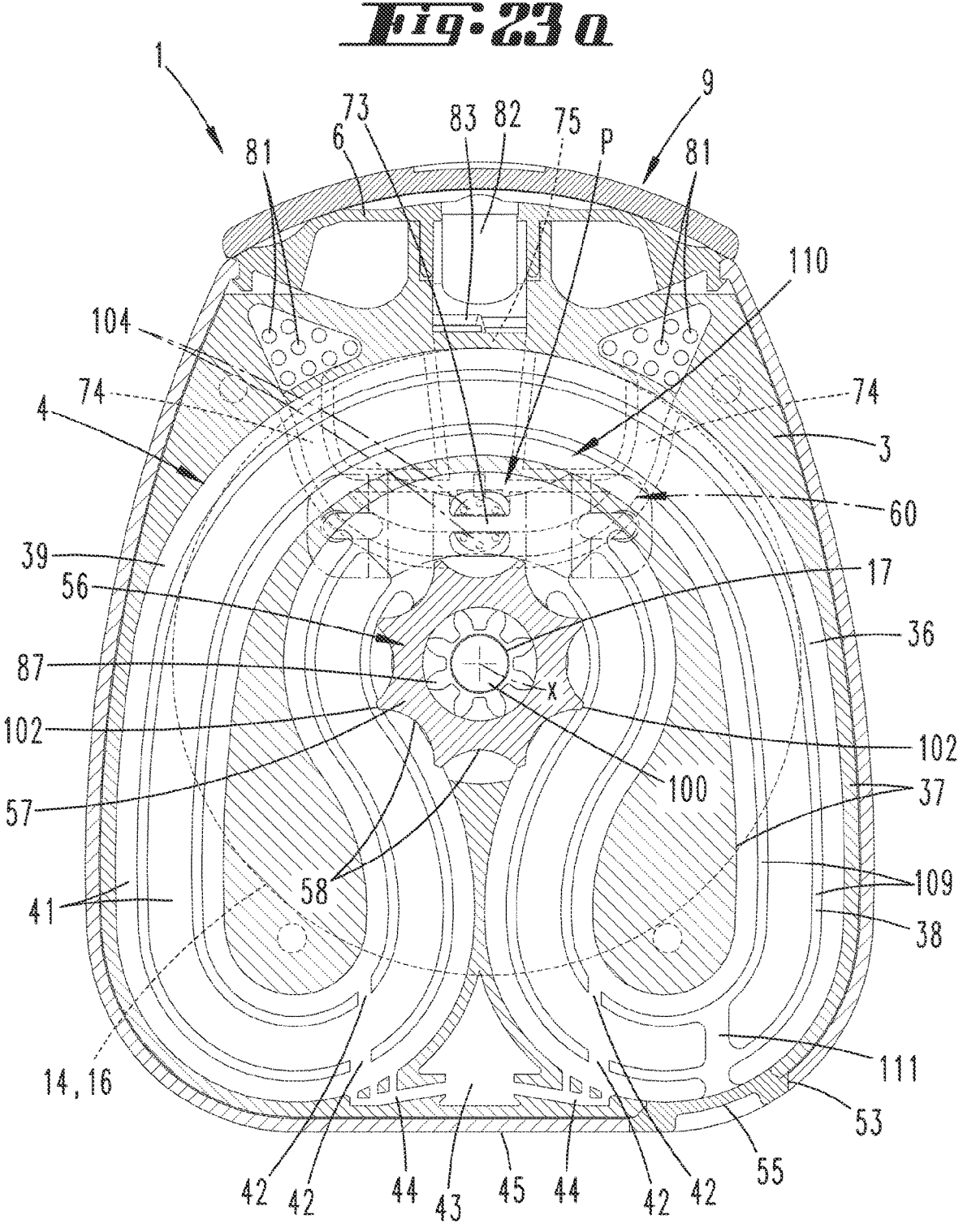

According to the illustration in FIG. 23, for example, longitudinal webs 109, which likewise extend in the longitudinal direction, can separate the longitudinal grooves 41 from one another in the longitudinal direction. In a zenith region 110 of the guide mechanism 4, which is assigned to the mouthpiece 6, the longitudinal webs 109 can be formed so as not to be continuous or so as to taper off beforehand, respectively. In this region, the longitudinal grooves 41 can therefore run freely into the web base 39 over the entire width, viewed transversely to the longitudinal extension of the longitudinal grooves 41. Distinctive longitudinal grooves are thus not present in this region.

In the case of the exemplary embodiment shown in FIG. 23a, in contrast, the zenith region 110 is also permeated with longitudinal webs 109 separating the longitudinal grooves 41.

According to FIG. 23a, the longitudinal webs 109 can also be connected to one another via a bridge section 111, preferably in the region of an insertion or housing opening 53, respectively, in the transverse direction to the longitudinal extension of the webs.

Substance 48, 48', in particular powder-type substance 48, 48', which optionally escapes from a substance container 5, can be guided via this groove structure in the base and/or ceiling region of the guideway 38 in a favorable manner into the intermediate spaces formed by the grooves, and optionally via said intermediate spaces into a collection chamber 43, which is further provided. This collection chamber 43 can result in a gusset region on the rear side in relation to the mouthpiece 6 between the turning regions of the guideway 38.

In this case, the collection chamber 43 is preferably connected via branches 44 to the sections of the guideway 38 facing one another.

The corresponding rear side of the device 1 can provide a floor space 45 for the device 1, so that the collection chamber 43 is arranged in a lowermost region of the device 1 in this case, and the substance, which optionally accumulates in the grooves 41 and 42, reaches in the direction of the collection chamber 43 due to the force of gravity.

The substance container 5, which is in particular illustrated in FIGS. 4 to 10, can initially and essentially be formed in a circular cylindrical manner, having a cylinder axis y, which is aligned in the same direction to the geometric pivot axis y or the axis of rotation of the drive shaft 17, respectively, in the accommodating position of the substance container 5 in the device 1 or in the guide mechanism 4, respectively.

As illustrated, the outer diameter d can be selected to be larger than the height extension of the substance container 5 viewed in the axial direction. The diameter d can thus correspond approximately to 1.2-times to 1.5-times the axial height e (see FIG. 6).

Figure 41:
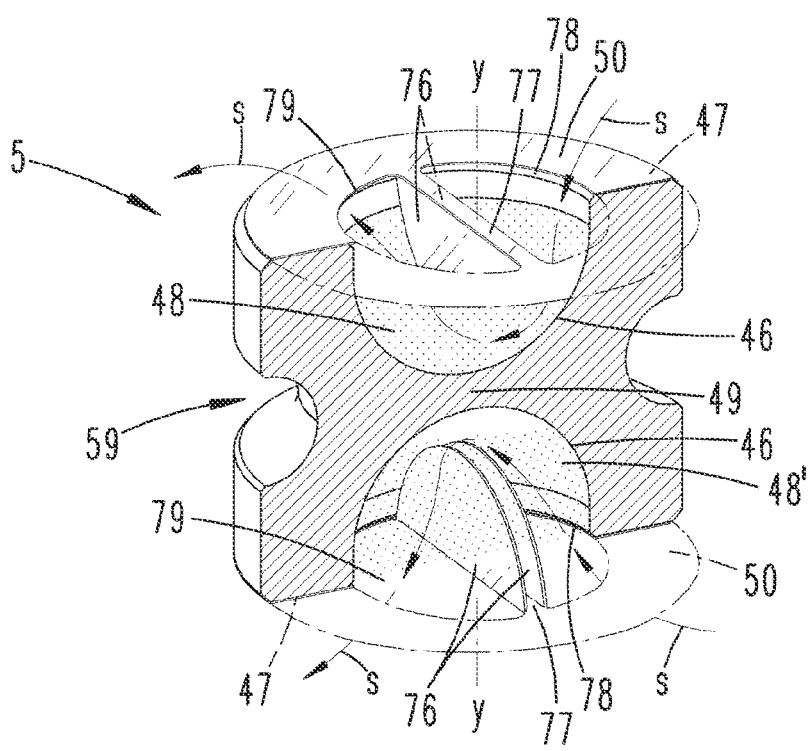
FIG. 41 shows a perspective sectional illustration through a substance container, in the case of covers, which are punctured by means of an insertion mechanism according to FIG. 36.

The substance container 5 is preferably also made of a hard plastic, for example polypropylene or polyethylene. It has two sub-regions 46 or cavities, respectively, which are located opposite one another in the direction of extension of the cylinder axis y and which are aligned concentrically to the cylinder axis y. As illustrated in FIG. 41, for example, they can essentially be formed approximately as hemispherical depressions. The respective opening results in the respective front surface, which is aligned transversely to the axis y. Each cavity can be designed to accommodate an amount of substance of, for example, 2 to 250 µg, further for example 10 to 100 µg.

Figures 38, 38A:
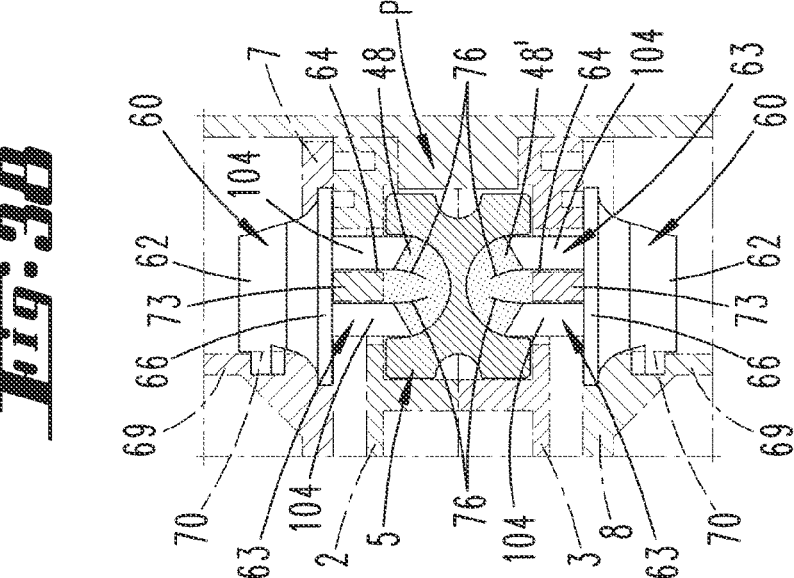
FIG. 38 shows a sectional illustration relating to the arrangement of two insertion mechanisms in the device for puncturing two covers of a substance container.
FIG. 38*a* shows a sectional illustration according to FIG. 38, but relating to the embodiment according to FIG. 36*a;*
Figure 41A:
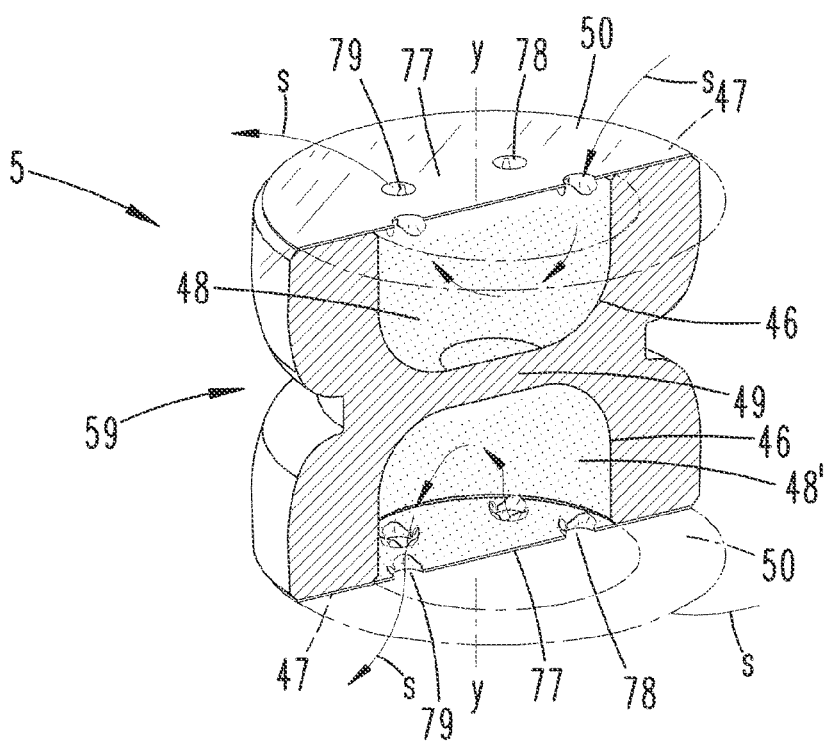
FIG. 41*a* shows an illustration corresponding to FIG. 41, but in the case of covers, which are pierced by an insertion direction according to FIG. 36*a;*

According to the illustrations in FIGS. 38a and 41a, a sub-region 46 of the substance container 5 can also be formed as essentially pot-like depression, comprising a cylindrical pot wall essentially relative to the cylinder axis y, and a pot base running transversely to the axis y. The transition from pot wall into the pot base is rounded. A favorable evacuation of the cavity can also be attained by means of this cross sectional geometry according to FIG. 41a. The pot base has a region, which extends in a planar manner transversely to the axis y or is formed so as to run in a curved manner with a radius, which is much larger compared to the transition from the pot wall into the pot base.

The sub-regions 46 are formed to accommodate a substance 48, 48' each.

Different substances 48, 48' can be accommodated in the sub-regions 46 by means of the separation of the sub-regions 46 from one another by including a base 49, which is preferably positioned in the center in relation to the height e.

The cavities or sub-regions 46, respectively, are in each case covered with an openable or pierceable cover 50, respectively. These covers 50 seal the respective sub-region 46 and the substance 48, 48' accommodated therein.

The cover 50 can, and preferably, be a foil, for example an aluminum foil. This foil is preferably welded to the front edge 47 of the substance container 5.

For this purpose, the front edge 47 can furthermore have ribs 51, which protrude circumferentially in the axial direction and which, after placement of the foil-like cover 50 in the course of the welding process, in particular ultrasonic welding process, melt and generate the adhesion of the cover 50 by equalization in the surface.

A plurality of such substance containers 5, which are preferably identical with respect to the setup and the dimensions, is accommodated in the guide mechanism 4, which is attached to the device. The respective accommodated substance in the substance containers 5, however, can be different, for example with respect to the composition and/or amount and/or dosage.

According to the illustrated exemplary embodiment, 30 such substance containers 5 can be accommodated in the continuous guideway 38, wherein the substance containers 5 come essentially in direct contact with one another, viewed in the longitudinal extension of the guideway 38. The substance containers 5 are thereby in each case guided laterally through the side walls 37 of the guide mechanism 4.

Figure 20:
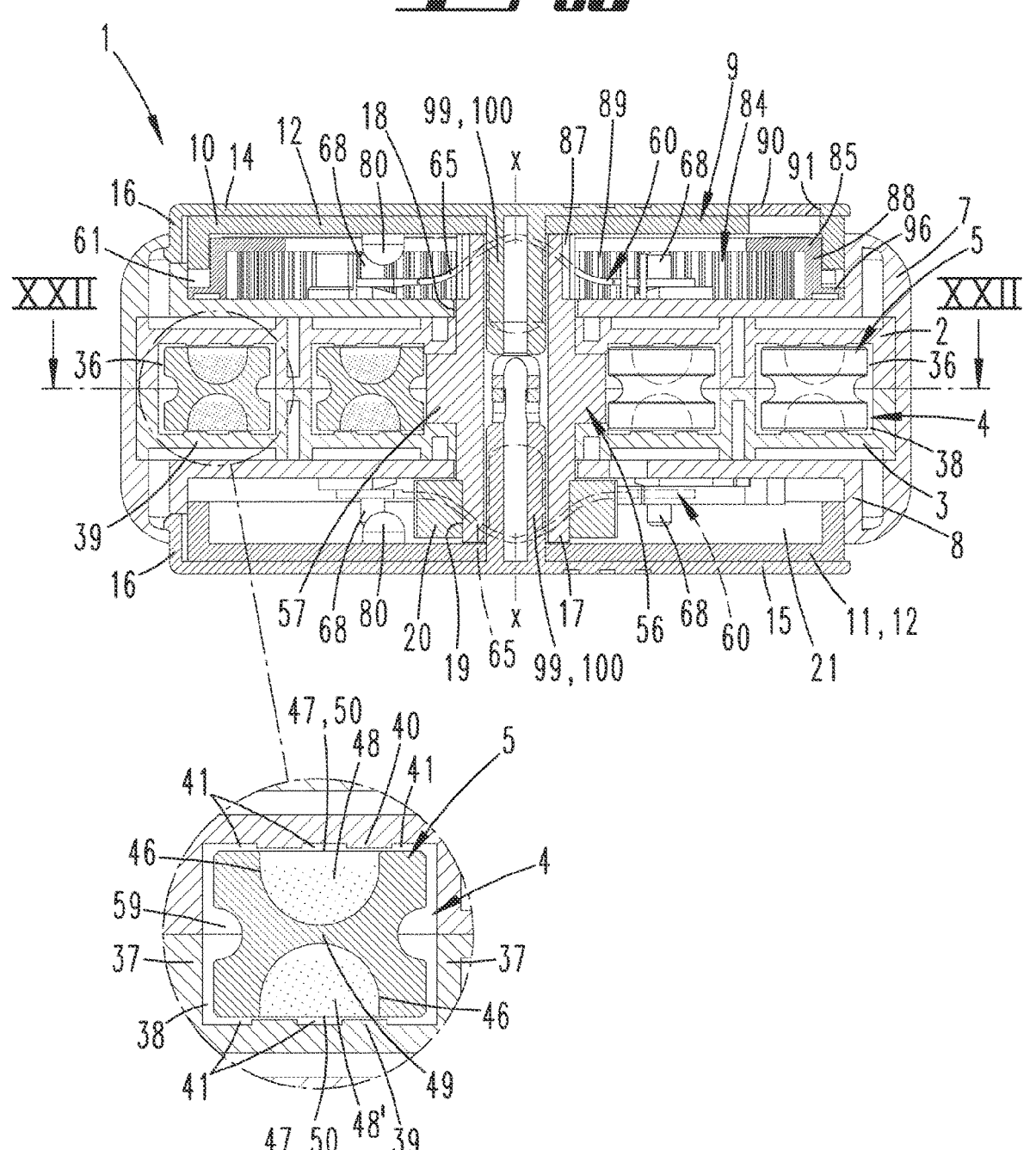
FIG. 20 shows the section according to the line XX-XX in FIG. 19.
Figure 21:
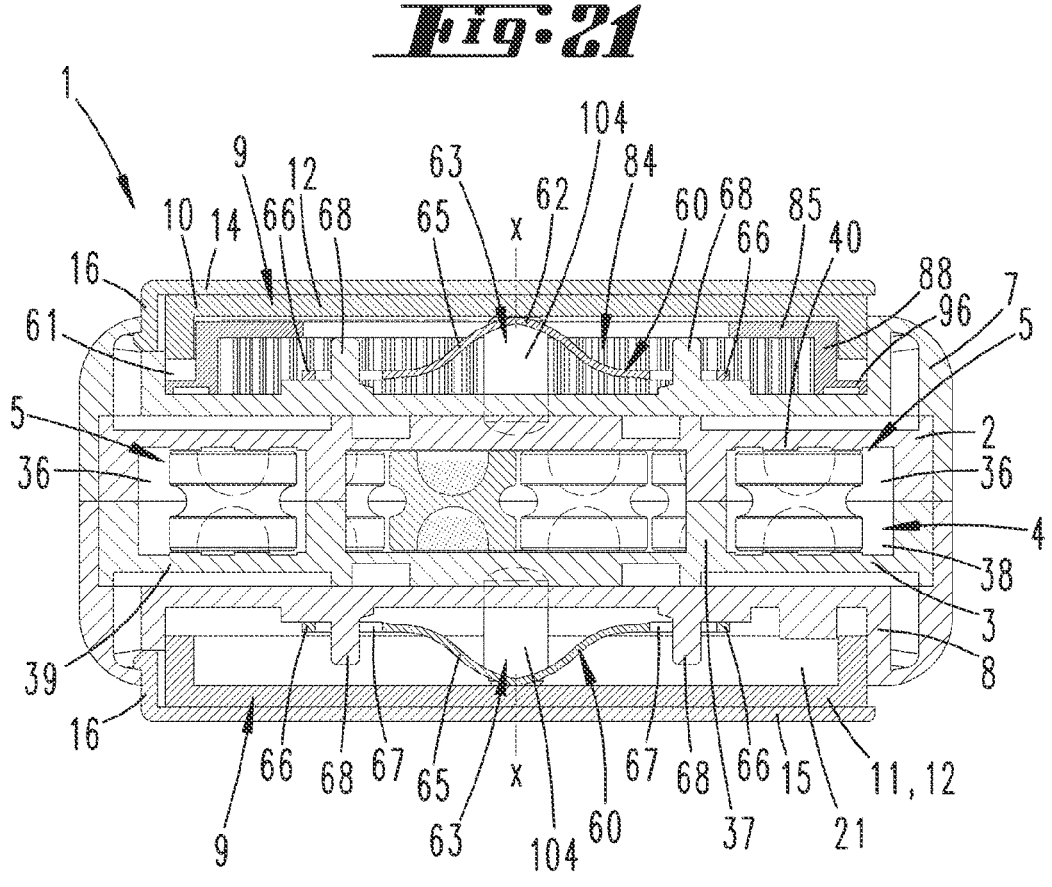
FIG. 21 shows the section according to the line XXI-XXI in FIG. 19.

Via their front edges 47, the substance containers 5 in each case experience a support on the bearing surfaces of web base 39 and web ceiling 40, which are raised with respect to the longitudinal and transverse grooves 41 and 42 (see FIG. 20, in particular the corresponding enlarged illustration).

Figure 24:
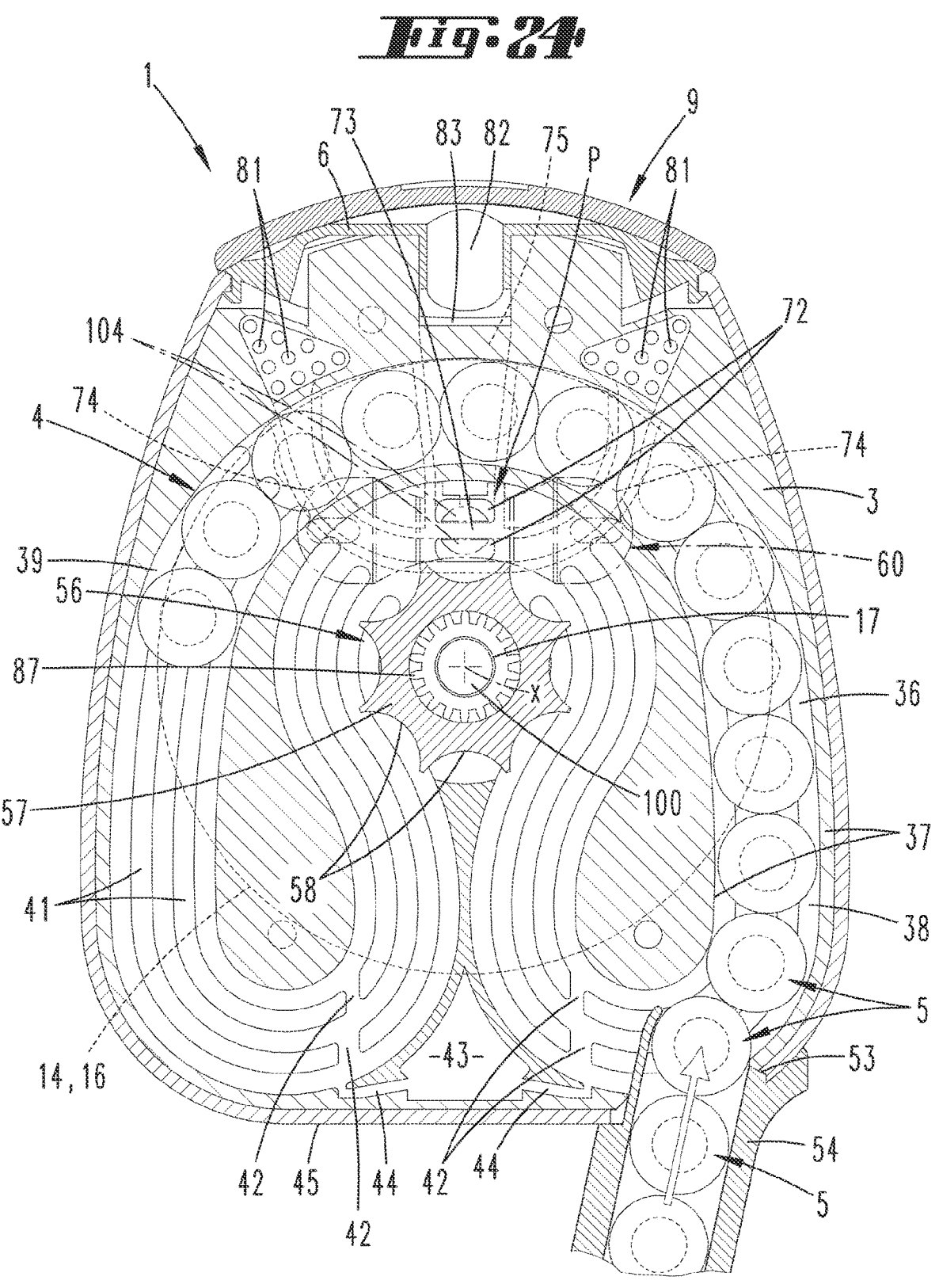
FIG. 24 shows a further illustration corresponding to FIG. 22, relating to a situation in the course of a filling of the device with substance containers.
Figure 25:
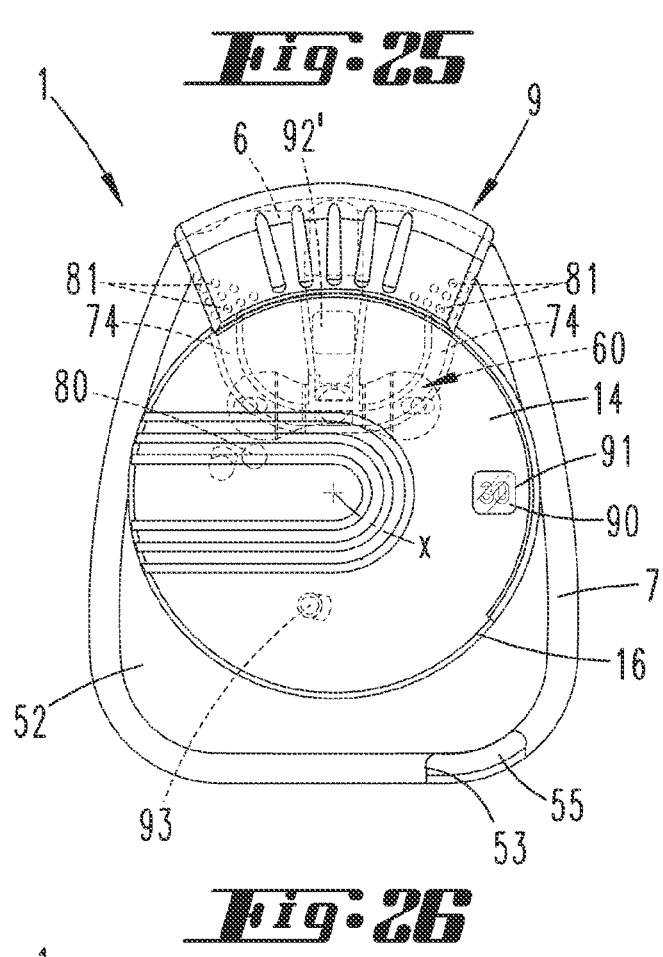
FIG. 25 shows a top view illustration of the device, essentially corresponding to FIG. 19.
Figure 26:
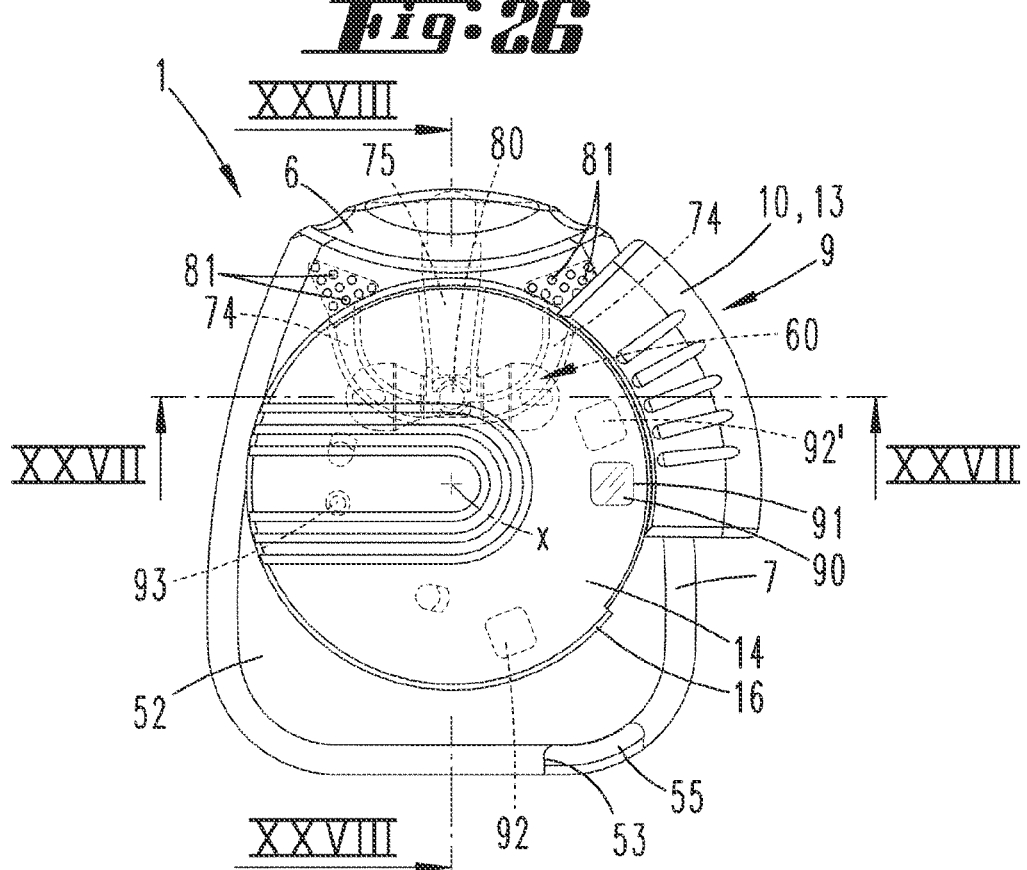
FIG. 26 shows an illustration corresponding to FIG. 25, but in the course of a pivoting movement of a closure cap in the direction of an open position.
Figure 21:
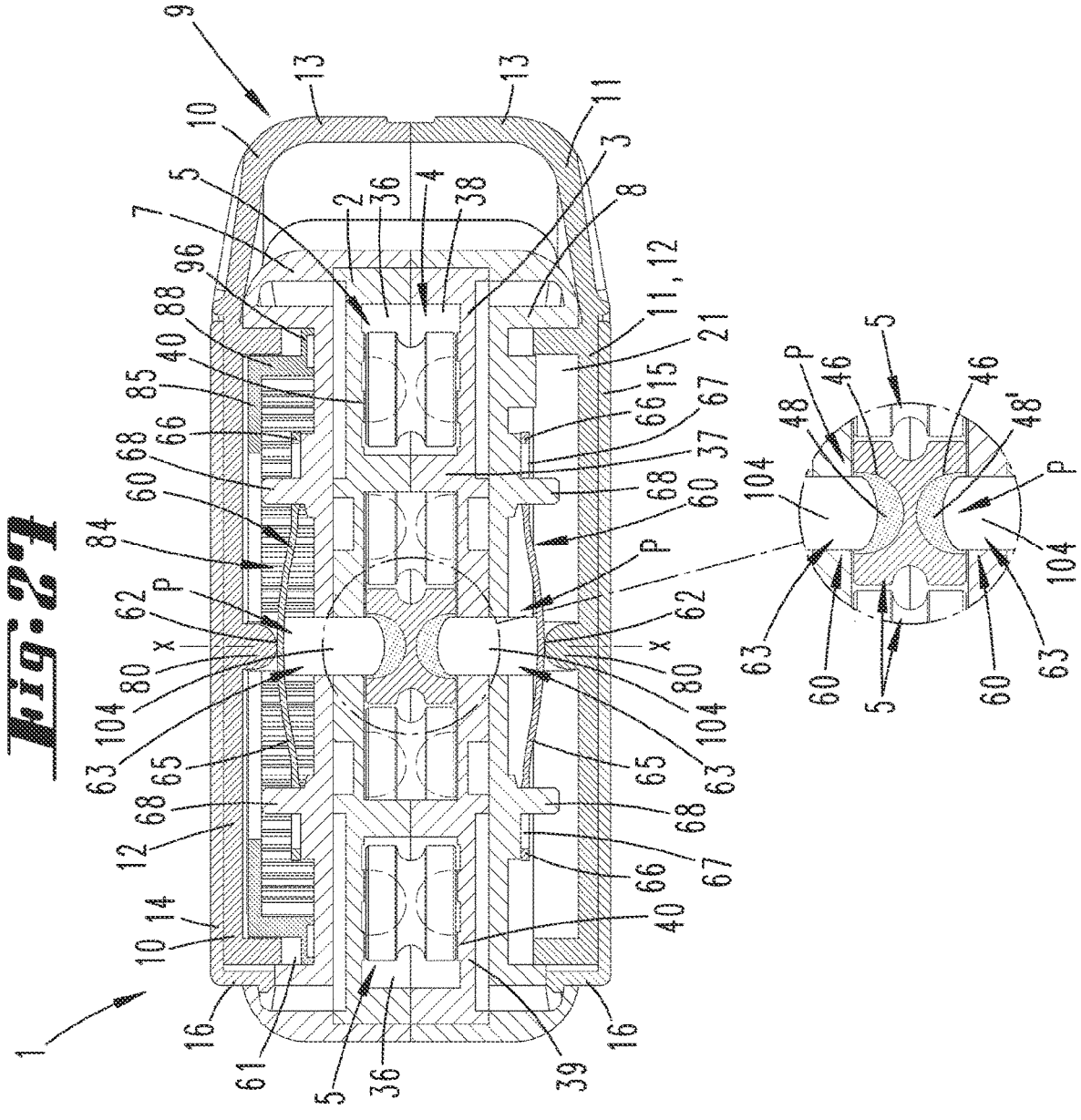
Figure 22:
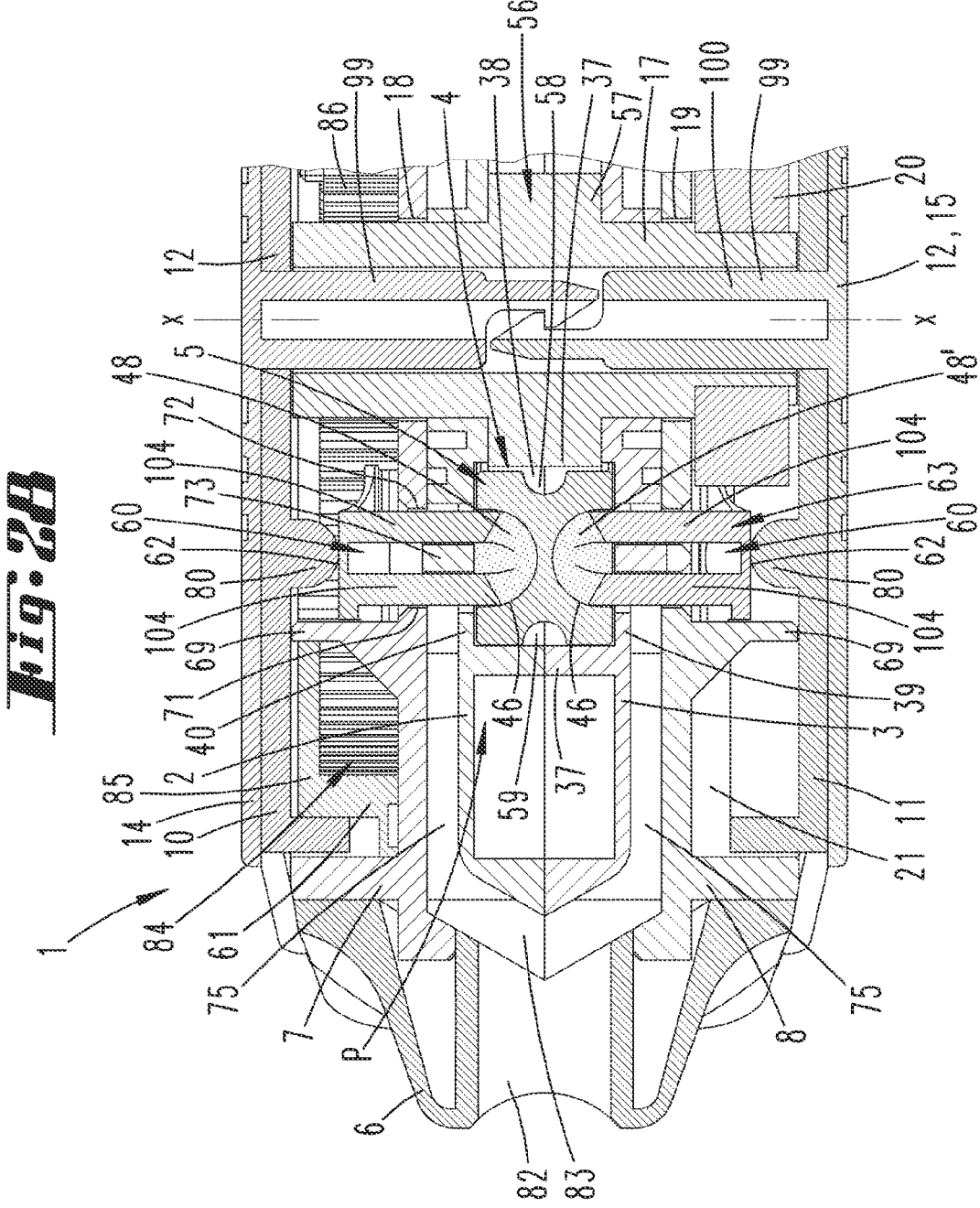
Figure 29:
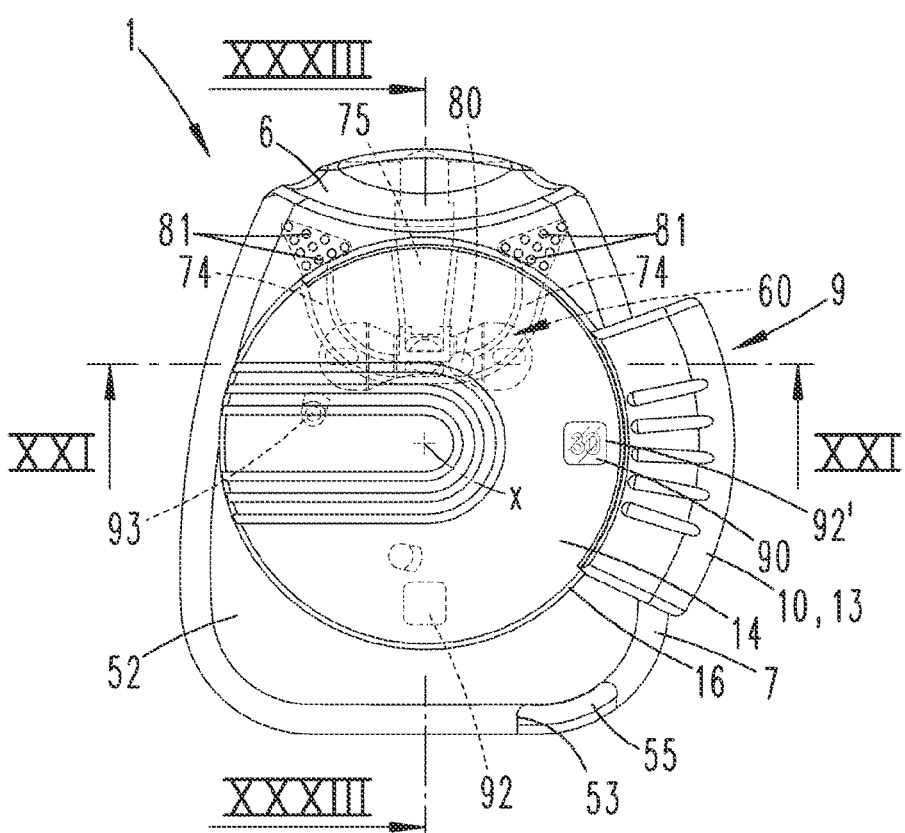
FIG. 29 shows a follow-up illustration for FIG. 26, relating to the closure cap open position.
Figure 30:
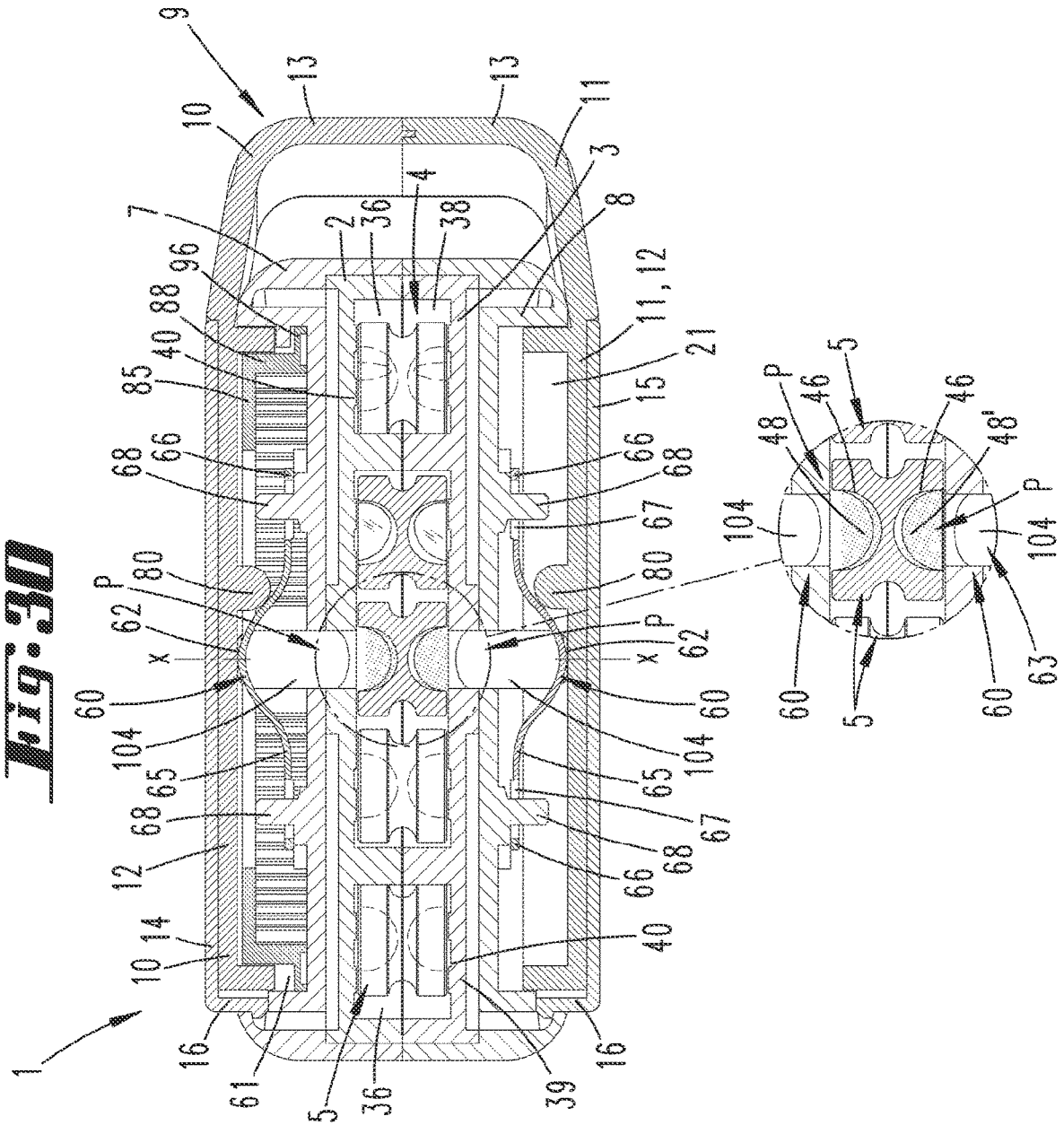
FIG. 30 shows the section according to the line XXX-XXX in FIG. 29.

As can be seen from the illustration in FIG. 24, the substance containers 5 can also be inserted into the guide mechanism 4 or into the guideway 38, respectively, only after essentially complete and operable assembly of the device 1. For this purpose, an insertion or housing opening 53, respectively, is provided at the housing 52 of the device 1, for instance assigned to the floor space 45 and thus more preferably assigned to a rearward turning section of the guideway 38.

An insertion aid, for example in the form of an insertion rail 54, can be attached to this opening 53, via which insertion aid the substance containers 5, which are accommodated in the rail so as to be arranged one behind the other, can be moved into the guideway 38 solely by means of the pressure propagating among the substance containers 5. The number of the substance containers 5 initially accommodated in the insertion rail 54 preferably corresponds to the number of substance containers 5, which can be maximally accommodated in the guideway 38 or the guide mechanism 4, respectively.

A continuous chain of substance containers 5, which is not connected to one another, in the guide mechanism 4 is closed by means of the last inserted substance container 5. The last inserted substance container 5 acts in the manner of a capstone in the continuous chain.

The run-in direction of the substance containers 5 in the course of the equipment of the device 1 by using, for example, such an insertion rail 54 corresponds to the displacement direction r of the substance containers 5 within the device 1 during conventional use of the device 1.

The insertion or housing opening 53, respectively, is final, that is, it is closed by means of a closure part 55 after complete equipment of the device 1 with the specified number of substance containers 5. The closure part 55 can be, for example, adhered or welded to the circumferential housing edge. A locking connection is optionally also possible in this regard. It is essential thereby that the closure part 55 can preferably no longer be removed without destruction after a corresponding closure.

In the closed position, the closure part 55 forms a part of the guideway 38 or of the side wall 37, respectively, on the wall inner side.

The substance containers 5 are moved in the guide mechanism 4 or the guideway 38, respectively, via a drive element 56 in the longitudinal direction of extension of the guideway 38 in such a way that an emptied substance container 5 is displaced out of the emptying position P, and an immediately following substance container 5, which stores substance 48 and 48' in its sub-regions 46, moves up into this emptying position P.

In the illustrated exemplary embodiment, the emptying position P is reached in the zenith of the loop of the guideway 38, which engages around the pivot axis x.

The drive element 56 can, and as is illustrated, be a star wheel-like drive wheel 57, which can be driven in a rotationally fixed manner on the drive shaft 17 via the actuating wheel 20. Only one such drive element 56 or drive wheel 57, respectively, is preferably provided in the device 1.

The drive wheel 57 is provided with radially open accommodating moldings 58, which, viewed over the circumference, are limited on both sides by means of radially protruding drive teeth 102 and which are spaced apart from one another by means of the drive teeth 102. As illustrated in the exemplary embodiment, eight such accommodating moldings 58 can be provided so as to be distributed evenly over the circumference. They are preferably designed identically in the form of concave edge recesses, in particular edge recesses in the shape of the segment of a circle, the radius of which is preferably adapted to the outer diameter d of a substance container 5.

The drive element 56 seizes the substance containers 5 in the region of the guideway loop by means of the accommodating moldings 58. For example seven such substance containers 5 are seized thereby or are guided by means of the drive wheel 57, respectively, and are guided in the guideway 38 as a result of rotational displacement of the drive wheel 57. Due to the contact pressure propagating in the continuous chain among the substance containers 5, all substance containers 5 are thereby moved further in response to corresponding rotation of the drive wheel 57.

The angle of rotation of the drive wheel 57 for changing the substance containers 5 in the emptying position P is a function of the number of accommodation moldings 58, among others. A corresponding angle of rotation of preferably approximately 45 degrees results in the case of eight accommodation moldings 58.

As mentioned, the pivot angle of the closure cap 9, via which pivoting displacement the drive wheel 57 is also influenced via the drive shaft 17, is selected to be larger than the permitted angle of rotation of the drive wheel 57. Due to the above-described slotted guide 28, the drive part 25 becomes disengaged from the actuating wheel 20 after performing a 45 degrees rotation of the drive wheel 57.

It is thus ensured that a displacement of the substance container chain only by one container in the displacement direction r is performed with each opening movement of the closure cap 9.

As can further be seen in particular from the illustrations in FIGS. 6, 7, and 41, the substance container 5 can have an outer circumferential groove 59, which is aligned transversely to the cylinder axis y, approximately in the center, based on the cylinder axis y. With respect to a cross section, in which the cylinder axis y presents itself as line, this groove 59 can have a hemispherical contour, which opens to the outside (see FIG. 7 or 41).

In alternative design, the groove base of the groove 59, which is directed radially to the inside, can be formed as a circular cylindrical wall section, starting at which the groove walls extend radially to the outside, in each case along a curved line, in a cross section according to FIG. 41a in such a way that a funnel-like widening of the groove 59 all the way into the container wall results.

The radial depth of the groove 59 or a corresponding radius of the circumferential hemispherical depression, respectively, can preferably be selected in such a way that as a whole, approximately an equalization of the wall thickness of the substance container 5 results, further in particular with respect to the wall, which revolves concentrically to the cylinder axis y.

So-called incidence phenomena, as they can appear in the case of excessive wall thicknesses in the case of hard plastic products, is counteracted by means of the given tapering of the substance container 5. In addition, material savings and, via the latter, weight savings also results thereby.

The groove 59 can furthermore also be used for guiding the substance containers 5 in the device 1, in particular in the guide mechanism 4, for the purpose of which one or both side walls 37 of the guideway 38 can have, centrally in its height viewed in the direction of extension of the pivot axis x, a rib or the like facing in the direction of the opposite side wall, which engages with the groove 59 of the substance container 5 in a guiding manner. Via this, the guidance of the substance containers 5 in the guide mechanism 4 can thus optionally take place solely via these ribs, which engage with the grooves 59. The front edges 47 of the substance containers 5 can thereby be spaced apart from the web base 39 and/or from the web ceiling 40.

Assigned to the emptying position P of a substance container 5, an insertion mechanism 60 is provided for the controlled systematic opening of the cover 50 on the substance container side.

According to the formation of two sub-regions 46 in the substance container 5, each having substances 48, 48', two insertion mechanisms 60 are preferably also provided. They are located opposite one another in the direction of extension of the pivot axis x.

One mechanism 60 can thereby be arranged in the depression 21 of the housing shell bottom part 8, and the further insertion mechanism 60 can be arranged in such a depression 61 in the housing shell top part 7.

An insertion mechanism 60 is illustrated in an exemplary manner in FIGS. 36 to 39.

Each insertion mechanism 60 initially has a retaining part 62, to which an insertion means 63 is fastened. Assigned to one insertion means 63, two separate insertion regions 104 are preferably provided, which can be designed, for example, in the shape of the segment of a circle in relation to a cross section according to the illustration in FIG. 39.

As can be seen, for example, from FIGS. 36a and 36b, each insertion region 104 can alternatively have two or more—here for example three—insertion tips 105. They can be arranged on the front side on pedestals 108 in the shape of the segment of a circle. The insertion tips 104 preferably protrude freely beyond a front surface of the pedestal 108.

In relation to a longitudinal extension L of an insertion mechanism 60 as a whole, the insertion regions 104 are spaced apart from one another transversely to this longitudinal extension L, wherein the flat sides of the segments of a circle face one another in the case of a formation of the insertion regions 104 in the shape of the segment of a circle. A slit-like free space 64 therefore results between the insertion regions 104, which preferably extends over the entire length of extension of the insertion regions 104, perpendicular to the longitudinal extension L, all the way to the retaining part 62.

The free end regions of the insertion regions 104 facing away from the retaining part 62 can be formed so as to be pointed in a blade-like manner, comprising a blade tip preferably in each case in the zenith region of the segments of a circle.

In case of formation of insertion tips 105, a mandrel-like formation is preferred, comprising a preferably cylindrical region 106, via which the insertion tip 105 is connected to the pedestal 108, and an adjacent tip region 107. Starting at the cylindrical region 106, the tip region 107 can be formed so as to taper conically towards the free end.

Figure 40:
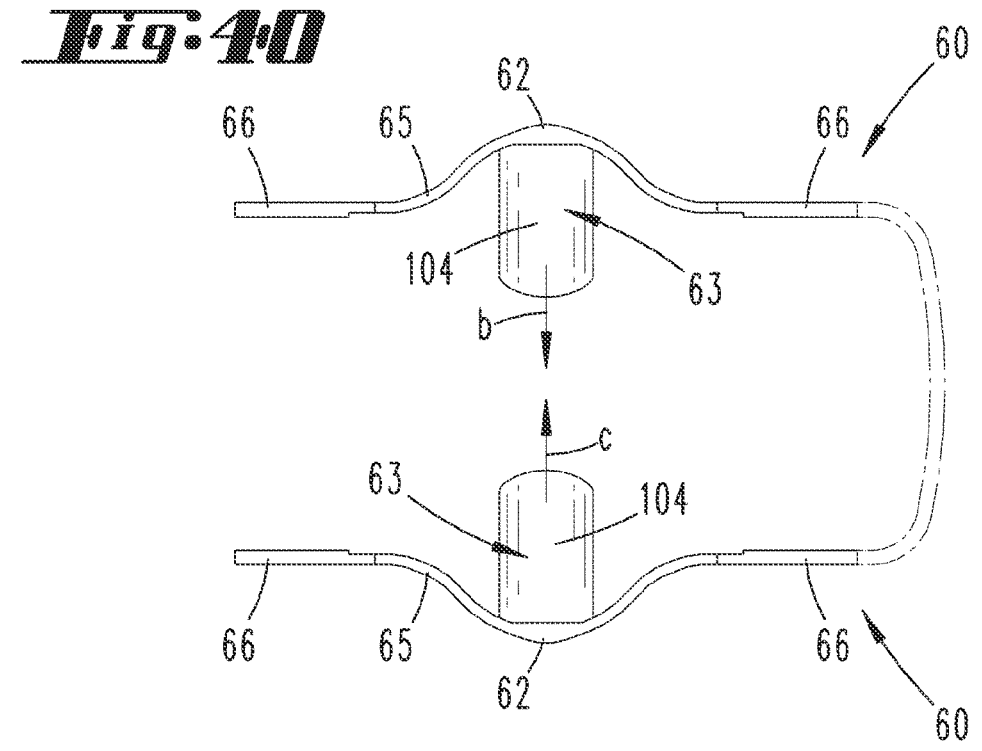
FIG. 40 shows a side view illustration essentially corresponding to FIG. 37, but relating to the arrangement of two insertion mechanisms.

Each insertion mechanism 60 preferably has a separate retaining part 62, As illustrated in an exemplary manner in FIG. 40 on the basis of the dash-dotted line, however, both insertion mechanisms 60 can also have a common retaining part 62.

In addition, the retaining part 62 of an insertion mechanism 60 can, and preferably, be formed in combination with a plastic spring 65. This plastic spring 65 has two spring arms 66, which are directed oppositely in the longitudinal extension L. In the respective end region, the spring arms 66 thereby preferably extend approximately within a common bearing plane E, which is aligned transversely to the direction of extension of the insertion means 63, in relation to the longitudinal extension L. In a side view according to FIG. 37, in which an insertion direction b or c, respectively, presents itself in a line-shaped manner and both spring arms 66 are displayed in their longitudinal extension, the central connecting region of the spring arms 66, viewed in the longitudinal extension L, extends in a concavely curved manner, wherein the retaining part 62 is preferably arranged in the center of the longitudinal extension L between the spring arms 66. The insertion means 63 are preferably arranged on the underside of the arched ceiling, which is provided by means of the concave design in the region of the retaining part 62, and preferably permeate the above-described common bearing plane E of the two spring arms 66 (see FIG. 37).

Starting at their free ends, in each case in the regions, which provide the bearing plane E, the spring arms 66, can have elongated hole-like guide recesses 67, which can in each case interact with the journal 68, which is connected to the housing. A fixing of the insertion mechanism 60 to the respective housing part (housing shell top part 7 or housing shell bottom part 8) can be attained via these journals 68. In addition, a guidance of the retaining part 62 in response to an insertion process can simultaneously also be provided via this.

Such a guidance can also be provided by interaction between a housing-side guide appendage 69 and an edge-side guide notch 70 provided in the region of the retaining part 62.

An exact guidance in particular of the insertion means 63 is in each case provided at least in the insertion direction b or c, respectively, of the respective insertion mechanism 60, so that the insertion direction b, c directed towards one another is preferably directed perpendicular to the bearing plane E over the entire displacement path.

In response to being acted on accordingly against the restoring force of the plastic spring 65, each insertion mechanism 60 is pushed in the direction of the pivot axis x through the respective cover 50 of the substance container 5 for opening the sub-regions 46. For this purpose, guide apertures 71, through which the insertion regions 104 can plunge, are provided in the respective depression base of the housing shell top part 7, which supports the insertion mechanism 60 and of the housing shell bottom part 8.

Corresponding apertures 72 are also formed in the housing inner top part 2 and the housing inner bottom part 3. They are initially provided in a bore-like manner, adapted to the outer diameter of the insertion means 63, thereby having a web 73, which separates the bore into two sub-sections centrally along a diameter line. With regard to its width viewed transversely to the diameter dimension, the web 73 is adapted to the corresponding clearance of the insertion regions 104 in the region of the slit-like guide 64 relative to one another. Such a web can also be provided in the housing shell parts in the region of the guide apertures 71.

The web 73 initially provides for a stabilization and guidance of the insertion regions 104, in particular in the course of the insertion process. In addition, the web 73 simultaneously provides for a separation between suction channels 74 and a discharge channel 75.

Suction channels 74 and a discharge channel 75 are in each case assigned separately to each cavity or each sub-region 46, respectively, of the sustenance container 5, which is in the emptying position P, via the respective webs 73.

As a result of the above-described arrangement and design of the insertion mechanism 60, the insertion means 63 or the insertion regions 104, respectively, preferably act in opposite insertion directions b and c, each directed along the pivot axis x. In response to corresponding stress for breaking through the covers 50, the insertion means 63 preferably act in directions that point towards one another.

Figure 39:
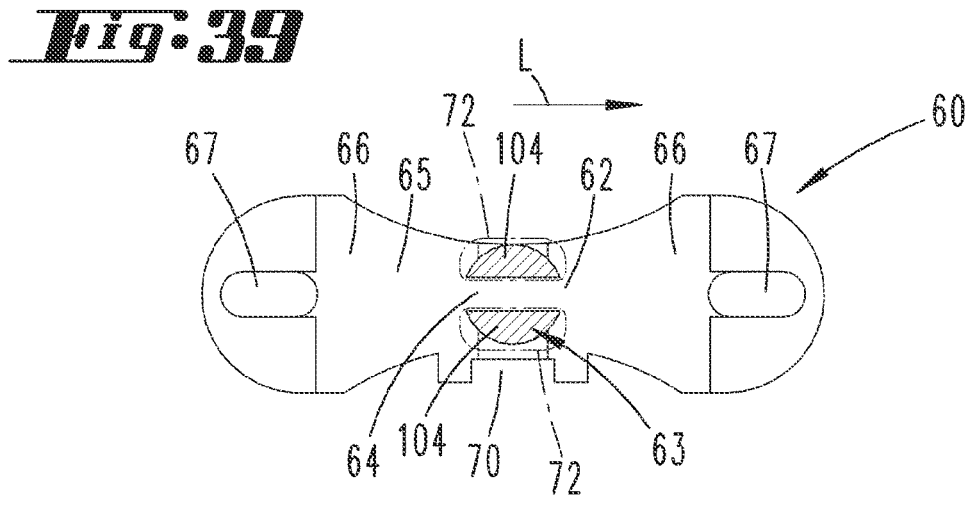
FIG. 39 shows the section according to the line XXXIX-XXXIX in FIG. 37.

Due to the insertion regions 104, two punching sections 76 in the shape of the segment of a circle can result in each cover 50 of the substance container 5, which is in the emptying position P, in the case of a formation of the insertion regions 104, for example according to the illustration in FIG. 36 or 39, which punching sections fold in inwards into the respective sub-region 46, preferably centrally along a diameter line of the substance container 5 or of the cover 50, respectively, over a remaining cover web 77 (see in particular FIG. 41).

As illustrated on the basis of FIGS. 38a and 41a, the insertion tips 105 of the insertion mechanism 60 according to FIG. 36a, for example, effect a hole-like punching of the container-side cover 50. The punched holes (openings 78 and 79), which thus result, can in each case have a diameter dimension, which can be selected to be smaller than, for example, 2 mm, more preferably smaller than 1.5 mm, thus optionally up to 0.5 mm or less. Pin-sized openings 78 and 79 preferably result.

A non-permeated or non-punched, central over web 77, respectively, also results here between two groups of punched holes, which groups consist of openings 78 on the one hand, and of openings 79 on the other hand.

Further assigned to each sub-region 46, an opening 78 for entrance of the air flow s from the suction channels 74, and an opening 79 for escape of the air flow s, which is mixed with substance 48 or 48', respectively, from the sub-region 46, can result thereby.

The web, which separates the suction channels 74 to the discharge channel 75, in the aperture 72 preferably bears on the cover 50 or the cover web 77, respectively, which results after opening the cover 50, so as to form a seal, so that a positive guidance of the air flow s through the opening 78 and through the sub-region 46 is provided.

The molding of the sub-region 46 as optionally hemispherical depression supports the evacuating effect via the air flows. No dead zones appear in terms flow. Due to the punching sections 76, which fold in in the direction of the sub-region base, the air flow s is guided through the sub-region 46 close to the base, which supports the complete evacuation of the sub-region 46.

Both insertion mechanisms 60 are preferably stressed and relieved simultaneously. An optional stressing of the one or of both insertion mechanisms 60 can also be carried out in this respect.

An embodiment, in the case of which the movement of both insertion mechanisms 60 takes place synchronously as a result of pivoting displacement of the closure cap 9, is illustrated in the graphic illustrations.

For this purpose, a cam 80 can be molded on the bottom side of the closure cap top part 10 and of the closure cap bottom part 11, in each case directed in the direction of the respective facing depression 21 or 61, respectively, which cam push down the insertion means 63 against the restoring force of the plastic spring 65 in the insertion direction b and c in the course of the pivoting movement of the closure caps

9, preferably downstream from a forward displacement of the substance container 5 into the emptying position P.

The above-described forward motion of the substance container 5 to reach the emptying position P is already reached, for example, with a pivoting displacement of the closure cap 9 by approximately 45 degrees. By eliminating the entrainment movement between closure cap 9 and actuating wheel 20, the closure cap 9 can then pivot freely further in the direction of the complete open position, wherein the cams 80 run over the retaining parts 62 of the insertion mechanisms 60, by acting on them, in the course of the this pivoting movement. As a result of the forward motion of the substance container 5, it is ensured thereby that a new, non-evacuated substance container 5 is present in the above-described emptying position P. A systematic puncturing of the covers 50 takes place only thereafter.

At the end of the pivoting movement of the closure cap 9, the cams 80 leave the influence region on the insertion mechanisms 60, which move back into their initial position again as a result of the restoring force of the plastic springs 65. The insertion means 63 or insertion regions 104, respectively, thereby move out of the sub-regions 46 of the substance container 5 again, for correspondingly releasing the openings 78 and 79 or for connecting these openings to the suction and discharge channels 74, 75 in terms of flow, respectively.

Two suction channels 74 are assigned to each sub-region 46 of the substance container 5, which is in the emptying position. The suction openings 81 thereof are formed on both sides of the mouthpiece 6 in the respective housing shell top part 7 or the housing shell bottom part 8, respectively, while the suction channels 74 can extend essentially in the housing inner top part 2 or the housing inner bottom part 3, respectively, in a molding manner (see, for example FIGS. 32 and 48).

A total of four suction channels 74 comprising four suction openings 81 thus result in the device 1, which suction openings 81 are positioned on both sides next to the mouthpiece 6 in such a way that they are exposed only after the closure cap 9 pivots upwards in the direction of the open position. In the closed basic position of the device 1, the suction openings 81 lie concealed under the closure cap 9 so as to be protected.

Figure 48:
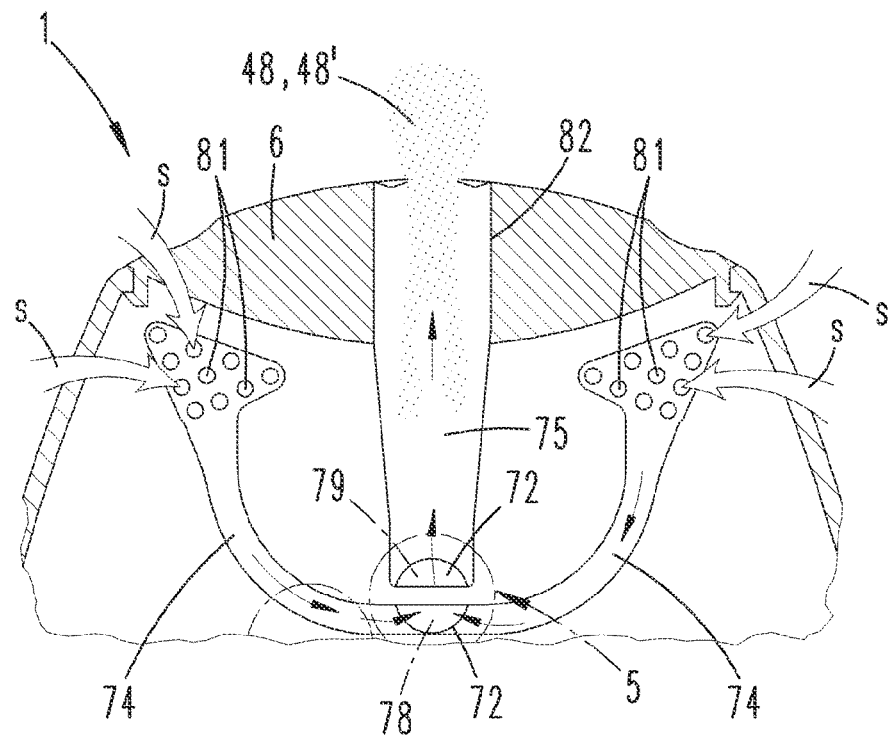
FIG. 48 shows the region of the air channels according to XLVIII in FIG. 47 in schematic illustration.

The two suction channels 74 of a cavity preferably meet directly in the region of the aperture 72, which is separated by means of the web 73 (see also FIG. 48).

Figure 32A:
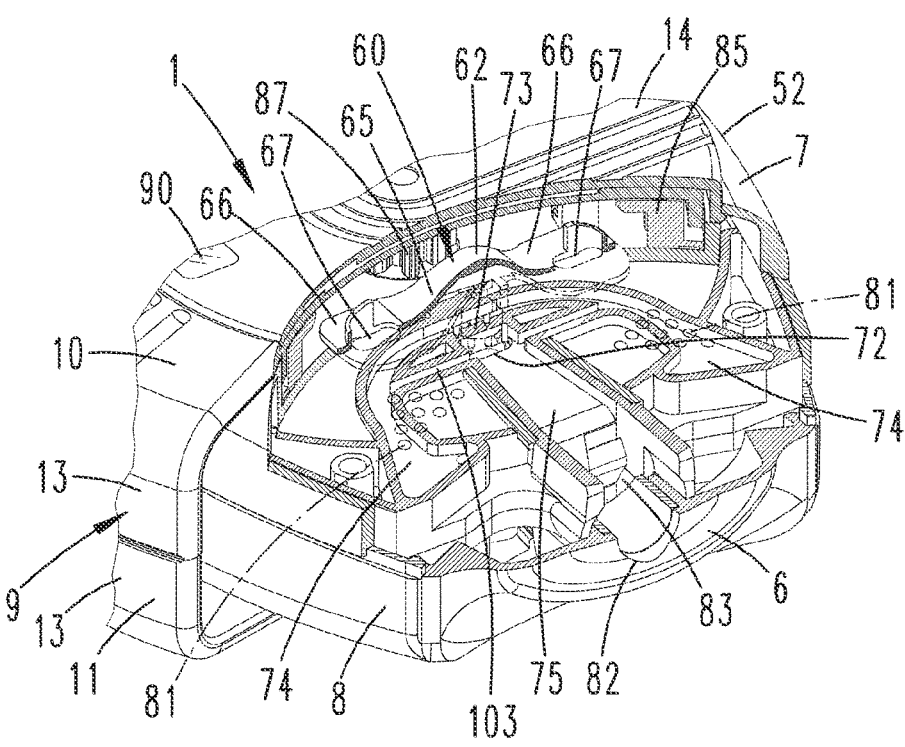
FIG. 32*a* shows an illustration corresponding to FIG. 32, relating to an alternative embodiment.
Figure 39A:
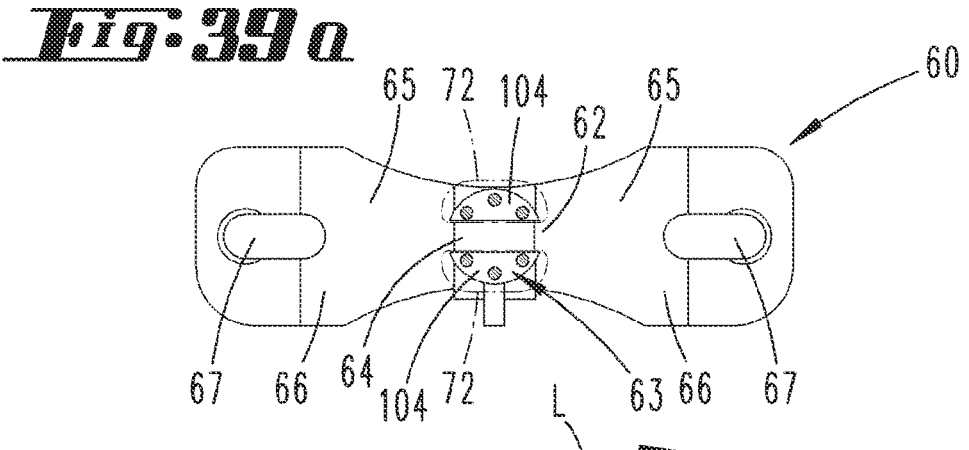
FIG. 39*a* shows the sectional illustration according to FIG. 39, relating to the second embodiment.
Figure 48A:
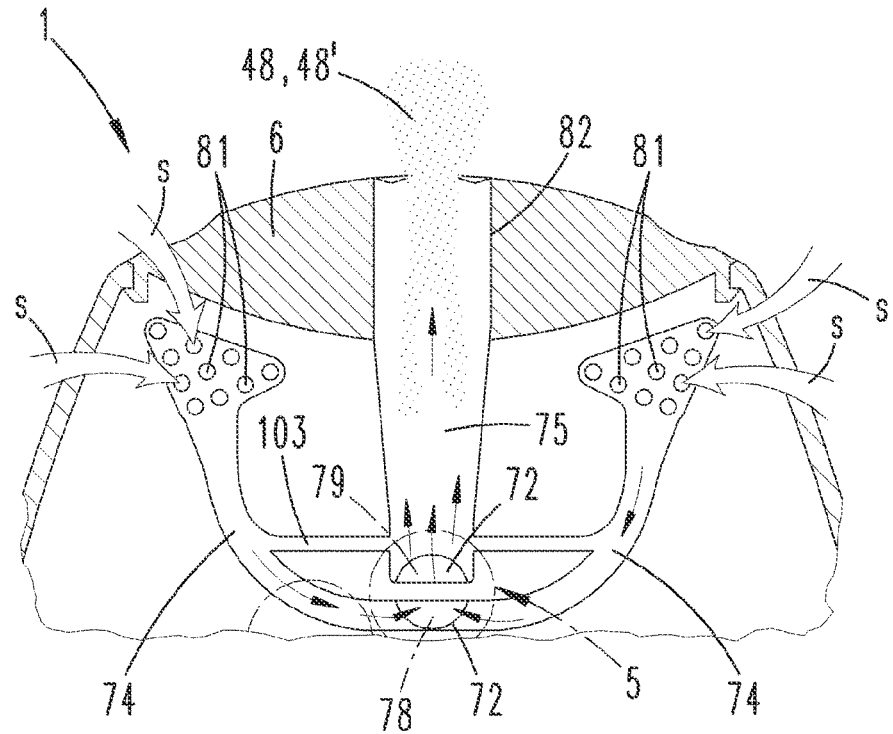
FIG. 48*a* shows an illustration corresponding to FIG. 48, but relating to the embodiment according to FIG. 32*a;*
Figure 49:
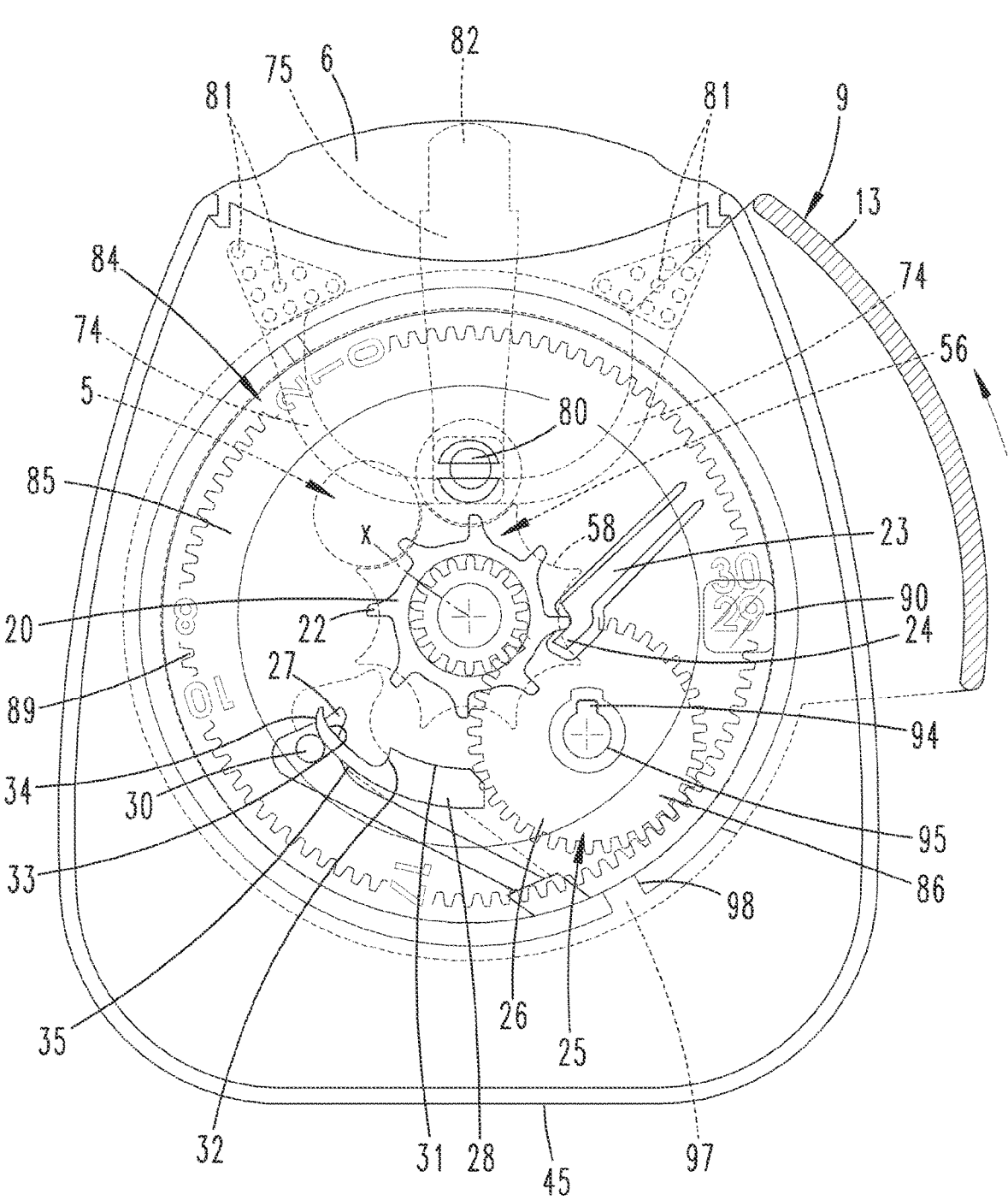
FIG. 49 shows an intermediate position in the course of the pivoting of the closure cap from the open position in the direction of the closed position.
Figure 50:
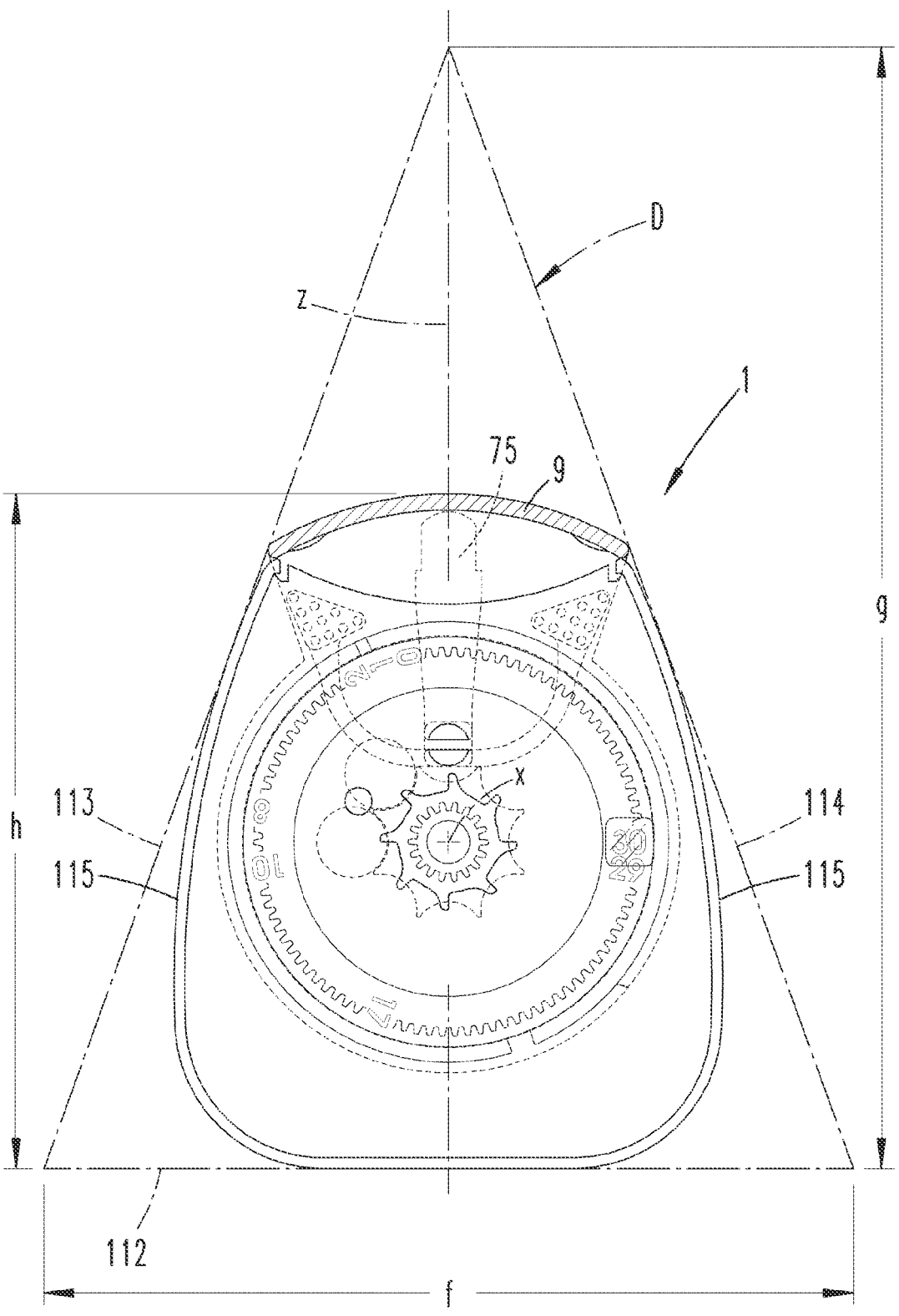
FIG. 50 shows a schematic illustration of the device in top view, for explanation of a geometric basic contour of the device and the dimensions thereof.

In alternative design, in particular and preferably in connection with the use of an insertion mechanism 60 comprising insertion tips 105 according to FIGS. 36a, 36b, and 39a, a bypass 103 can be provided, which connects the suction channels 74 in the air flow direction s upstream of the substance container 5 or upstream of the emptying position P, respectively (see FIGS. 32a and 48a). A portion of the drawn-in air can flow through this transverse channel (bypass 103) directly and without permeating the cavities of the substance container 5 into the discharge channel 75 in the course of an inhalation process. Such a bypass 103 can, and preferably, be assigned to each pair of the suction channels 74.

A discharge channel 75 is further assigned to each cavity or to each sub-region 46, respectively, of a substance container 5, which is in the emptying position. A total of two discharge channels 75 therefore result in the device 1, which, initially starting at the assigned aperture opening, are guided separately from one another in the direction of the mouthpiece 6, in particular in a direction approximately perpendicular to the above-described rearward floor space 45.

Figure 33:
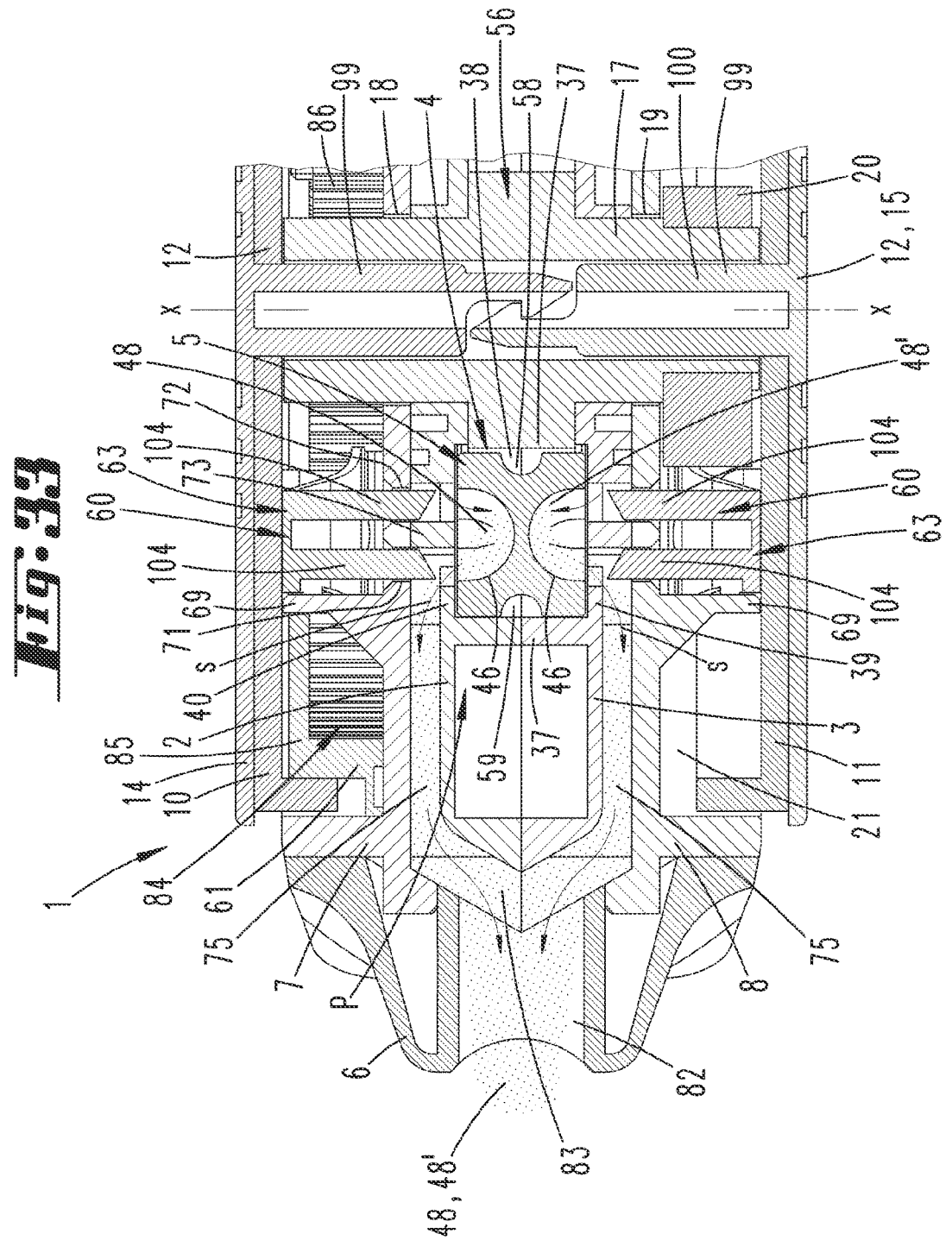
FIG. 33 shows the section according to the line XXXIII-XXXIII in FIG. 29.
Figure 34:
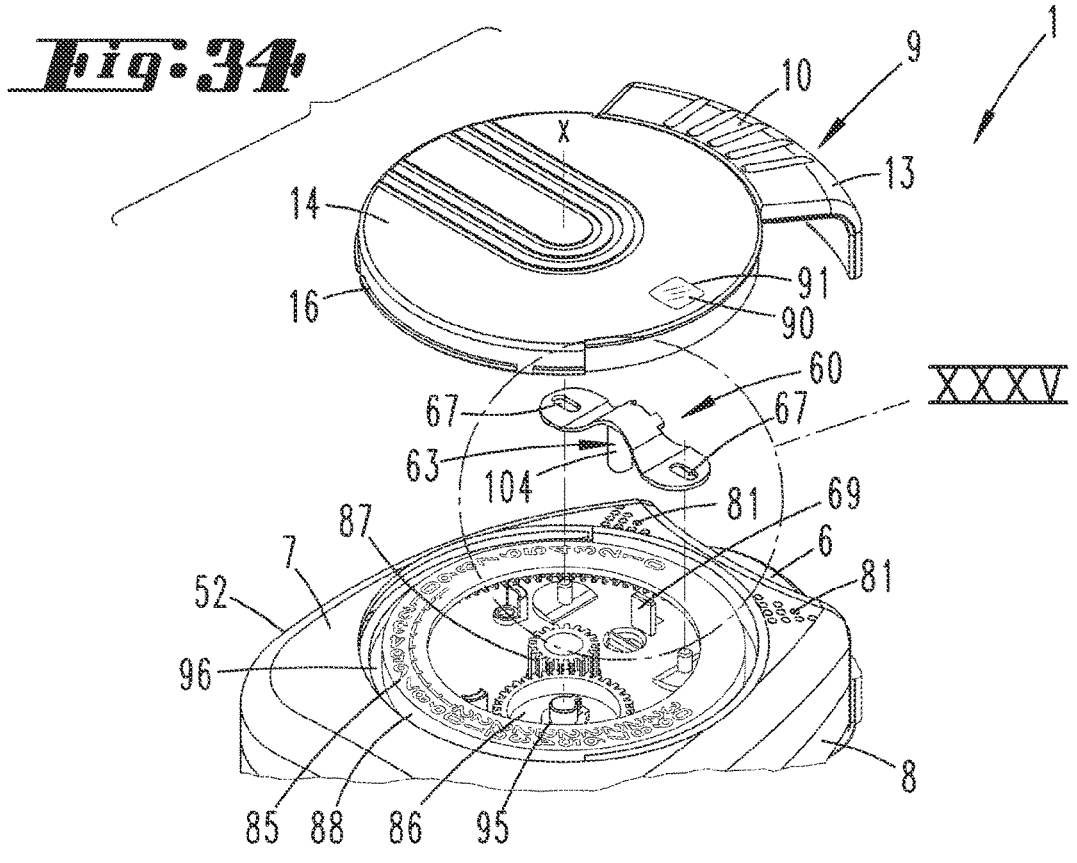
FIG. 34 shows a partially exploded perspective illustration of the device, relating to the region of an insertion mechanism.
Figure 35:
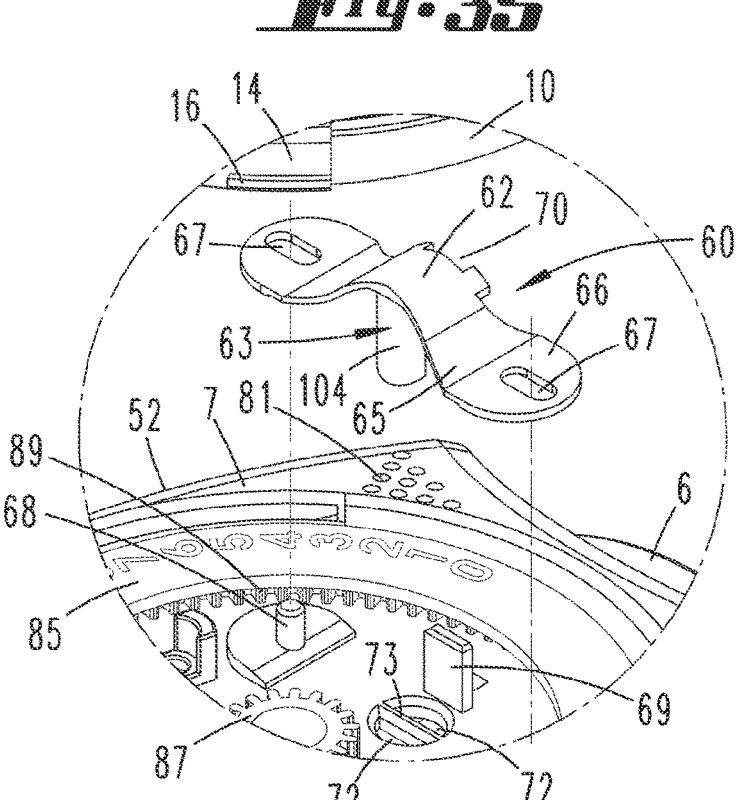
FIG. 35 shows the enlarged illustration of the region XXXV in FIG. 34.

The two discharge channels 75 are merged directly in the transition to the mouthpiece channel 82 (see, for example, FIG. 33). A swirling element or the like can optionally be provided in this merging region 83.

According to the above-described design and separation of the discharge channels 75, the substances 48 and 48' are evacuated separately from the respective sub-regions 46 and are merged only immediately before passing into the breathing region of the user, in particular in the merging region 83 in the root region of the mouthpiece 6, and are mixed or swirled, respectively, in the course of an inhalation process after opening the covers 50 by means of the insertion mechanisms 60 and build-up of an air flow s as a result of aspiration or breathing in, respectively, via the mouthpiece 6.

The device 1 is further designed and formed to count the performed or still remaining emptying processes or inhalation processes, respectively. A counter 84 is provided for this purpose.

The counter 84 essentially has a ring-shaped counting wheel 85, a transfer gear 86, and a drive pinion 87, as can be seen, for example from the detailed illustrations in FIGS. 17 and 18. The drive pinion 87 is arranged in a rotationally fixed manner on the drive shaft 17, and meshes with an external toothing of the transfer gear 86. The external toothing of the transfer gear 86, in turn, meshes with an internal toothing 89, which is formed on the inner side of a circumferential collar 88 of the counting wheel 85.

The gear-like counter 84 formed in this way is essentially arranged between the housing shell top part 7 and the assigned closure cap top part 10.

Symbols, in particular numerals, are applied in the region of a top-side, ring-shaped surface of the counting wheel 85. The number of the numerals preferably corresponds to the number of the substance containers 5, which can be accommodated in the guide mechanism 4 of the device 1. According to the illustrated exemplary embodiment, a numerical sequence of 0 to 30 can thus be provided.

The current rotational orientation of the counting wheel 85 and therefore the current number, which is to be displayed, of unused substance containers 5, which are still present, for example, or, in the alternative, of already used-up substance containers 5, is visible from the outside to the user via a transparent window 90 in the cover part 16. The window 90 closes an adapted aperture 91 in the cover part 16. The closure cap top part 10 also has such an aperture 92, which, in the mouthpiece closed position of the closure cap 9 in relation to the pivot axis x, is located one on top of the other so as to be aligned to the aperture 91 and the window 90 in the cover part 14. In addition, a further aperture 92' can be provided, which is formed in an offset manner in the circumferential direction and through which the display can also be recognized in the closure cap open position.

In the course of the closure cap pivoting movement, the numerals of the counting wheel 85 are no longer visible via the window 90, because the otherwise closed cover section 12 of the closure cap top part 10 moves between counting wheel 85 and window 90. Upon completed pivoting-back movement of the closure cap 9 into the closed position of the mouthpiece 6, the number, which is visible, compared to before the introduction of a pivoting of the closure cap 9 from the closed position into the open position, is increased by 1 or, in the alternative, is reduced by 1.

The closure cap pivoting movement therefore effects a displacement of the substance containers 5 within the guide mechanism 4 by one position, in order to move the next substance container 5 into the emptying position P in this way, as well as the opening of the covers 50 of both sub-regions 46 of the substance container 5, which is in the emptying position P, and additionally a change of the display of the counter 84.

The transfer gear 86 of the counter 84 is guided on an axle journal 93 of the housing shell top part 7. A geometric axis of rotation of the transfer gear 86 thereby extends in the same direction as the pivot axis x.

On the end side, therefore spaced apart from the depression base, in which the axle pin 93 is rooted, the axle journal 93 has a radial protrusion 94. The transfer gear 86 has a correspondingly adapted, key hole-like central aperture, which allows pushing the transfer gear 86 onto the axle journal 93 only in one rotational orientation. In the operating position, the hub of the transfer gear 86 circumvents the radial protrusion 94 of the axle journal 93, so that the transfer gear 86 can be rotated freely.

Along its circumferential collar 88, the counting wheel 85 has a radial collar 86 pointing to the outside. In the operating position, this radial collar 86 is covered by a web, which protrudes radially inwards in the region of a housing wall encompassing the depression 61, and which forms a further alignment molding 97. A recess 98, which is open on the edge, is provided in the region of the radial collar 96 of the counting wheel 85.

As a result of the above-described designs, the counting wheel 85 as well as the transfer gear 86 can be assembled only in a specified angular alignment relative to one another and/or relative to the drive pinion 87.

The installation position in particular of the counting wheel 85 can thereby be such that only after inserting the substance containers 5 into the otherwise operational device 1, the counting wheel 85 is aligned in such a way that for example the maximal number of inhalation, which can then still be performed, or unused substance containers, respectively, can be recognized through the window 90, for instance the numeral 30 according to the shown exemplary embodiment. By means of the substance containers 5, which are inserted successively into the guide mechanism 4, for example via the insertion rail 54, the counting wheel 85, which is inserted in a specified rotational position, is entrained via the above-described gear arrangement and is moved into the exact initial position.

After opening the cavities of the last substance container 5 in the continuous row—and preferably an inhalation performed thereafter—the device 1 can be blocked in order to prepare a presumed next inhalation.

In this position, the counter 84 can thus, and preferably, display zero. The counting wheel 85 rotated accordingly into this position can thereby move against a section, which is attached to the device, for example against the alignment molding 97, in a blocking manner with a stop rib 101, which is molded in the region of the radial collar 96.

A blocking of the gear-like counter 84 and, via the latter, of the drive shaft 17 can be attained thereby, so that when an attempt is made to pivot open the closure cap 9 out of the closed position in the direction of the open position, the drive part 25 moves against the blocked drive shaft 17 or the actuating wheel 20, respectively, which is connected thereto in a rotationally fixed manner.

After emptying all substance containers 5, the device 1 is blocked and can preferably not be used further. By means of the preferred continuous stringing-together of the substance containers 5 in the guide mechanism 4, the first, already emptied substance container would be move into the emptying position P again without such a blocking after the last substance container 5. Such an incorrect operation is counteracted by means of the above-described blocking.

A device, which is characterized in that the drive element 56 is formed as drive wheel 57, comprising radially open accommodating moldings 58, for acting on a respective substance container 5.

A device, which is characterized in that the drive element 56 can be moved in a transport direction r by means of a drive part 25 that can be moved by the user.

A device, which is characterized in that the drive element 56 is arranged so as to be coaxially and rotationally connected to an actuating wheel 20.

Device, which is characterized in that the drive element 56 and the actuating wheel 20 are arranged in a rotationally fixed manner on a drive shaft 17.

A device, which is characterized in that the actuating wheel 20 can be acted on b means of the drive part 25, wherein the actuating wheel 20 further interacts with a non-return device 23 to prevent a reverse rotation.

A device, which is characterized in that the drive part 25 is connected to a closure cap 9, so that a movement of the drive part 25 takes place in the transport direction r in response to movement of the closure cap 9 on a pivoting path into an open position.

A device, which is characterized in that the drive part 25 engages with the actuating wheel 20 only over a sub-region of the pivoting path of the closure cap 9 with the help of a slotted guide 28.

A device, which is characterized in that the drive part 25 is formed so as to be capable of rebounding.

A device, which is characterized in that, in a closed position of the closure cap 9, the drive part 25 is in an initial position, with low or missing spring deflection.

A device, which is characterized in that the guide mechanism 4 has a guideway 38, which communicates with a closable insertion openings 53 for substance containers 5 in the housing 52.

A device, which is characterized in that the insertion opening 53 can be closed by means of a closure part 55, which can only be removed in a destructive manner.

A device, which is characterized in that on the inner side, the closure part 55 forms a portion of the guideway 38.

A device, which is characterized in that, assigned to an insertion mechanism 60 for a substance container 5, the guideway 38 has longitudinal grooves 41, in which substance 48, 48', which may have escaped in the insertion mechanism 60, can collect.

A device, which is characterized in that a collection chamber 43 is formed, in which substance 48, 48' transported in the longitudinal grooves 41 can be collected.

A substance container 5, which is characterized in that the substance container 5 has two sub-regions 46, which, in each case separately, have an amount of substance 48, 48', and that both sub-regions 46 have an openable pierceable cover 50.

A substance container, which is characterized in that the substance container 5 is formed essentially cylindrical.

A substance container, which is characterized in that, based on a cylinder longitudinal axis y, the substance container 5 has an outer circumferential groove 59, which is aligned transversely to the cylinder axis y, approximately in the center.

A substance container, which is characterized in that the substance container 5 consists of a hard plastic.

A substance container, which is characterized in that the cover 50 consists of a foil, for example an aluminum foil.

A substance container, which is characterized in that the foil is welded to a front edge 47 of the substance container 5.

A method, which is characterized in that, in a first method step when the device 1 is already assembled, the substance containers 5 are introduced into a storage chamber 36 of the device 1 through a separate housing opening 53, and that, in a second method step, the separate housing opening 53 is closed by means of a closure part 55, which can no longer be removed without destruction.

A method, which is characterized in that the substance containers 5 are not connected to one another and are moved only under contact pressure propagating among the substance containers 5.

A method, which is characterized in that a guide mechanism 4 for the substance containers 5 in the form of a guideway 38 is formed in the device 1, and that the substance containers 5 in the guideway 38 are inserted in a transport direction r, which is also given during conventional use of the device 1.

All of the disclosed features (alone, but also in combination with one another) are essential for the invention. The disclosure content of the corresponding/enclosed priority documents (copy of the prior application) is hereby also included in its entirety into the disclosure of the application, also for the purpose of adding features of these documents into claims of the present application. With their features, the subclaims, also without the features of a referenced claim, characterize independent inventive further developments of the prior art, in particular to file divisional applications on the basis of these claims. The invention specified in each claim can additionally have one or several of the features specified in the above description, in particular provided with reference numerals and/or specified in the list of reference numerals. The invention also relates to designs, in the case of which individual features, which are mentioned in the above description, are not realized, in particular insofar as they are discernibly expendable for the respective intended purpose or can be replaced by other technically identical means.

LIST OF REFERENCE NUMERALS

1 device
2 housing inner top part
3 housing inner bottom part
4 guide mechanism
5 substance container
6 mouthpiece
7 housing shell top part
8 housing shell bottom part
9 closure cap
10 closure cap top part
11 closure cap bottom part
12 cover section
13 cap section
14 cover part
15 base part
16 collar
17 drive shaft
18 bore
19 bore
20 actuating wheel
21 depression
22 entrainment protrusion
23 non-return device
24 locking lug 25 drive part
26 spring arm
27 entrainment lug
28 slotted guide
29 control surface
30 control journal
31 first contact surface
32 recess
33 second contact surface
34 control surface
35 third contact surface
36 storage chamber
37 side wall
38 guideway
39 web base
40 web ceiling
41 longitudinal groove
42 transverse groove
43 collection chamber
44 branch
45 floor space
46 sub-region
47 front wall
48 substance
48' substance
49 bottom
50 cover
51 rib
52 housing
53 insertion or housing opening, respectively
54 insertion rail
55 closure part
56 drive element
57 drive wheel
58 accommodating molding
59 groove
60 insertion mechanism
61 depression
62 retaining part
63 insertion means
64 slit-like free space
65 plastic spring
66 spring arm
67 guide recess
68 journal
69 guide appendage
70 guide notch
71 guide aperture
72 aperture
73 web
74 suction channel
75 discharge channel
76 punching section
77 cover web
78 opening
79 opening
80 cam
81 suction opening
82 mouthpiece channel
83 merging region
84 counter
85 counting wheel
86 transfer gear
87 drive pinion
88 collar
89 internal toothing
90 window 91 aperture
92 aperture
92' aperture
93 axle journal
94 alignment molding
95 aperture
96 radial collar
97 alignment molding
98 recess
99 hollow journal
100 axle body
101 stop rib
102 drive tooth
103 bypass
104 insertion region
105 insertion tip
106 cylindrical region
107 tip region
108 pedestal
109 longitudinal web
110 zenith region
111 bridge section
112 base line
113 leg
114 leg
115 side wall section
a direction of rotation
b insertion direction
c insertion direction
d outer diameter
e height
f base width
g height
h height
r transport direction
s air flow
x pivot axis
y cylinder axis
z axis of symmetry
D triangle
E bearing plane
L longitudinal extension
P emptying position

The invention claimed is:

1. A device (1) for inhaling powder-type substances (48, 48'), comprising:
a guide mechanism, and
a plurality of substance containers (5) that are configured to be moved successively into an emptying position, wherein the plurality of substance containers (5), which are not connected to one another, are accommodated for direct contact with one another in the guide mechanism (4) attached to the device, and can be moved by contact pressure propagating among the plurality of substance containers (5),
wherein the guide mechanism (4) further has a single drive element (56) configured for moving the plurality of substance containers (5), the drive element (56) being formed by a single drive wheel (57) comprising accommodating moldings (58) separated by drive teeth (102),
wherein one substance container (5) of the plurality of substance containers in an emptying position is located in one of the accommodating moldings (58) of the drive wheel (57), wherein the drive element (56) is configured to be moved in a transport direction (r) by means of a drive part (25) that is configured to be moved by a user, wherein the drive element (56) is arranged so as to be coaxially and rotationally connected to an actuating wheel (20), and wherein the drive part (25) is an elongated protrusion formed in one piece with a closure cap (9) for a mouthpiece, the closure cap being pivotable around a pivot axis, resulting in a coaxial arrangement of the drive element, actuating wheel and closure cap.

2. The device according to claim 1, wherein the plurality of substance containers (5) form a continuous row in the guide mechanism (4).

3. The device according to claim 1, wherein the accommodating moldings comprise radially open accommodating moldings (58), that are configured to act on the plurality of substance containers (5).

4. The device according to claim 1, wherein the drive element (56) and the actuating wheel (20) are arranged in a rotationally fixed manner on a drive shaft (17).

5. The device according to claim 1, wherein the actuating wheel (20) is configured to be acted on by means of the drive part (25), wherein the actuating wheel (20) further interacts with a non-return device (23) to prevent a reverse rotation.

6. The device according to claim 1, wherein the closure cap is configured such that a movement of the drive part (25) takes place in the transport direction (r) in response to movement of the closure cap (9) on a pivoting path into an open position.

7. The device according to claim 6, wherein the drive part (25) engages with the actuating wheel (20) only over a sub-region of the pivoting path of the closure cap (9) with the help of a slotted guide (28).

8. The device according to claim 6, wherein, in a closed position of the closure cap (9), the drive part (25) is in an initial position, with reduced or missing spring deflection.

9. The device according to claim 1, wherein the drive part (25) is formed so as to be capable of rebounding.

10. The device according to claim 1, wherein the guide mechanism (4) has a guideway (38), which communicates with a closable insertion opening (53) for substance containers (5) in a housing (52).

11. A device (1) for inhaling powder-type substances (48, 48'), comprising:

a guide mechanism, and a plurality of substance containers (5) that are configured to be moved successively into an emptying position, wherein the plurality of substance containers (5), which are not connected to one another, are accommodated for direct contact with one another in the guide mechanism (4) attached to the device, and can be moved by contact pressure propagating among the plurality of substance containers (5), wherein the guide mechanism (4) further has a single drive wheel (57) comprising accommodating moldings (58) separated by drive teeth (102), and wherein one substance container of the plurality of substance containers (5) in an emptying position is located in one of the accommodating moldings (58) of the drive wheel (57), wherein the guide mechanism (4) has a guideway (38), which communicates with a closable insertion opening (53) for the plurality of substances containers (5) in a housing (52), and further comprising a closure part configured for closing the insertion opening (53), wherein the closure part can only be removed in a destructive manner.

12. The device according to claim 11, wherein on an inner side, the closure part (55) forms a portion of the guideway (38).

13. A device (1) for inhaling powder-type substances (48, 48'), comprising:

a guide mechanism, and a plurality of substance containers (5) that are configured to be moved successively into an emptying position, wherein the plurality of substance containers (5), which are not connected to one another, are accommodated for direct contact with one another in the guide mechanism (4) attached to the device, and can be moved by contact pressure propagating among the plurality of substance containers (5), wherein the guide mechanism (4) further has a single drive wheel (57) comprising accommodating moldings (58) separated by drive teeth (102), and wherein one substance container of the plurality of substance containers (5) in an emptying position is located in one of the accommodating moldings (58) of the drive wheel (57), wherein the guide mechanism (4) has a guideway (38), which communicates with a closable insertion opening (53) for the plurality of substances containers (5) in a housing (52), and wherein, assigned to an insertion mechanism (60) for a substance container (5), the guideway (38) has longitudinal grooves (41) that are configured for collecting substance (48, 48'), which may have escaped in the insertion mechanism (60).

14. The device according to claim 13, further comprising a collection chamber (43) that is configured for collecting substance (48, 48') transported in the longitudinal grooves (41).

\* \* \* \* \*